United States Patent
Heckel et al.

(10) Patent No.: US 7,262,206 B2
(45) Date of Patent: Aug. 28, 2007

(54) CYCLOALKYL—CONTAINING 5-ACYLINDOLINONES, THE PREPARATION THEREOF AND THEIR USE AS MEDICAMENTS

(75) Inventors: Armin Heckel, Biberach (DE); Gerald Jürgen Roth, Biberach (DE); Jörg Kley, Mittelbiberach (DE); Stefan Hoerer, Ochsenhausen (DE); Ingo Uphues, Ummendorf (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 192 days.

(21) Appl. No.: 11/077,355

(22) Filed: Mar. 10, 2005

(65) Prior Publication Data

US 2005/0203104 A1 Sep. 15, 2005

Related U.S. Application Data

(60) Provisional application No. 60/557,668, filed on Mar. 30, 2004.

(30) Foreign Application Priority Data

Mar. 12, 2004 (DE) .................. 10 2004 012 070

(51) Int. Cl.
*C07D 401/12* (2006.01)
*C07D 401/14* (2006.01)
*C07D 209/14* (2006.01)
*A61K 31/454* (2006.01)
*A61K 31/404* (2006.01)

(52) U.S. Cl. .................. 514/323; 514/326; 514/418; 546/187; 548/486

(58) Field of Classification Search ............. 514/323, 514/326; 546/187; 548/486
See application file for complete search history.

(56) References Cited

U.S. PATENT DOCUMENTS 7,176,231 B2 * 2/2007 Heckel et al. ............. 514/418

FOREIGN PATENT DOCUMENTS

WO WO 01/27080 A 4/2001

OTHER PUBLICATIONS

Bramson, H. N., et al. "Oxindole-based Inhibitors of Cyclin-Dependent Kinase 2 (CDK2): Design, Synthesis, Enzymatic Activities, and X-ray Crystallographic Analysis", Journal of Medicinal Chemistry, vol. 44, p. 4339-4358, 2001 XP002274118.
Embi, et al. "Glycogen Synthase Kinase-3 from Rabbit Skeletal Muscle: Separation from Cyclic-AMP-Dependent Protein Kinase and Phosphorylase Kinase", Eur. J. Bio. Chem. vol. 107, pp. 519-527, 1980.
S. Nikoulina, et al. "Potential Role of Glycogen Synthase kinase-3 in Skeletal Muscle Insulin Resistance of Type 2 Diabetes" Diabetes, vol. 49, pp. 263-271, 2000.
Cohen, et al. Nature Reviews: Molecular Cellular Biology, vol. 2, 1-8, 2001.
Cross, et al. "Selective small-molecule inhibitors of glycogen synthase kinase-3 activity protect primary neurones from death", J. Neurochemistry, vol. 77, pp. 94-102, 2001.
Sato, N., et al. "Maintenance of Pluripotency in human and mouse embryonic stem cells through activation of Wnt signaling by a pharmacological GSK-3-specific inhibitor", Nature Medicine, vol. 10, pp. 55-63, 2004.

* cited by examiner

*Primary Examiner*—Kamal A. Saeed
*Assistant Examiner*—Michael Barker
(74) *Attorney, Agent, or Firm*—Michael Morris; Mary-Ellen M. Devlin; David Dow

(57) ABSTRACT

The present invention relates to cycloalkyl-containing 5-acylindolinones of general formula

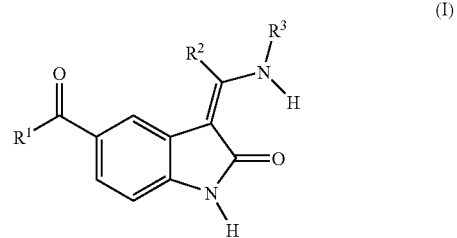

(I)

wherein $R^1$ to $R^3$ are defined as in claims 1 to 6, the tautomers, the enantiomers, the diastereomers, the mixtures thereof and the salts thereof, which have valuable pharmacological properties, particularly an inhibiting effect on protein kinases, particularly an inhibiting effect on the activity of glycogen synthase kinase (GSK-3).

11 Claims, No Drawings

CYCLOALKYL—CONTAINING 5-ACYLINDOLINONES, THE PREPARATION THEREOF AND THEIR USE AS MEDICAMENTS

RELATED APPLICATIONS

This application claims priority benefit under 35 USC 119(e) from U.S. Provisional Application 60/557,668, filed Mar. 30, 2004 and German application number DE102004012070.6 the contents of which are incorporated herein.

DESCRIPTION OF THE INVENTION

The present invention relates to new cycloalkyl-containing 5-acylindolinones of general formula

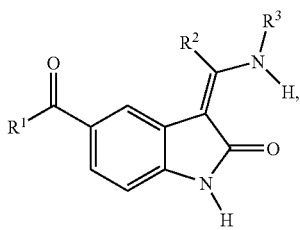

(I)

the tautomers, the enantiomers, the diastereomers, the mixtures thereof and the salts thereof, particularly the physiologically acceptable salts thereof with inorganic or organic acids or bases, which have valuable pharmacological properties, for example an inhibiting effect on protein kinases, particularly an inhibiting effect on the activity of glycogen-synthase-kinase (GSK-3), the preparation thereof, the use thereof for the prevention or treatment of diseases or conditions associated with an altered GSK-3 activity, particularly type I and type II diabetes mellitus, diabetes associated disorders such as diabetic neuropathy, degenerative neurological diseases such as Alz-heimer's disease, stroke, neurotraumatic injuries, bipolar disorders, pharmaceutical compositions containing a compound of general formula (I) or a physiologically acceptable salt thereof and processes for the preparation thereof.

In the above formula I $R^1$ denotes a straight-chain or branched $C_{1-5}$-alkyl group wherein the hydrogen atoms may be wholly or partly replaced by fluorine atoms, or an aryl group optionally substituted by a fluorine, chlorine or bromine atom,
  while by an aryl group is meant a phenyl or naphthyl group, $R^2$ denotes a straight-chain or branched $C_{1-7}$-alkyl or $C_{3-7}$-cycloalkyl group, a 5- or 6-membered heteroaryl group with one to three heteroatoms selected from the group N, S and O, optionally substituted by one or two fluorine, chlorine, bromine or iodine atoms or one or two nitro, cyano, amino, $C_{1-3}$-alkyl or $C_{1-3}$-alkoxy groups, while both the heteroatoms and the substituents may be identical or different, a phenyl group wherein two adjacent carbon atoms are linked together through a methylenedioxy, ethylenedioxy or difluoromethylenedioxy group, a phenyl group, to which another phenyl ring or a 5- or 6-membered heteroaromatic ring with one to three heteroatoms selected from the group N, S and O, wherein the heteroatoms may be identical or different, is anellated, while the bicyclic group may be substituted by one or two fluorine, chlorine, bromine or iodine atoms or one or two nitro, cyano, amino, $C_{1-3}$-alkyl or $C_{1-3}$-alkoxy groups and the substituents may be identical or different, or a phenyl group which may be substituted by one to three fluorine, chlorine, bromine or iodine atoms or by one to three $C_{1-3}$-alkyl, nitro, cyano, amino, di-($C_{1-3}$-alkyl)-amino, $C_{1-3}$-alkyl-carbonylamino, phenylcarbonylamino, $C_{1-3}$-alkylsulphonylamino, arylsulphonylamino, trifluoromethyl, $C_{1-3}$alkylsulphonyl, carboxy, $C_{1-3}$-alkoxy, di-($C_{1-3}$-alkyl)-amino-$C_{1-3}$-alkyloxy, $C_{1-3}$-alkoxy-carbonyl, $C_{1-3}$-alkylaminocarbonyl, hydroxy-carbonyl-$C_{1-3}$-alkyl-aminocarbonyl, $C_{1-3}$-alkoxy-carbonyl-$C_{1-3}$-alkyl-aminocarbonyl, amino-$C_{1-3}$-alkyl-aminocarbonyl, $C_{1-3}$-alkyl-amino-$C_{1-3}$-alkyl-aminocarbonyl, di-($C_{1-3}$-alkyl)-amino-$C_{1-3}$-alkylaminocarbonyl, di-($C_{1-3}$-alkyl)-amino-carbonyl-$C_{1-3}$-alkoxy, $C_{1-3}$-alkyl-amino-carbonyl-$C_{1-3}$-alkoxy, amino-carbonyl-$C_{1-3}$-alkoxy, carboxy-$C_{1-3}$-alkoxy, $C_{1-3}$-alkyloxy-carbonyl-$C_{1-3}$-alkoxy, piperidinylcarbonyl-$C_{1-3}$-alkoxy, piperazinylcarbonyl-$C_{1-3}$-alkoxy, 4-($C_{1-3}$-alkyl)-piperazinylcarbonyl-$C_{1-3}$-alkoxy, carboxy-$C_{1-3}$-alkyl, $C_{1-3}$-alkoxy-carbonyl-$C_{1-3}$-alkyl, amino-$C_{1-3}$-alkyl, di-($C_{1-3}$-alkyl)-amino-$C_{1-3}$-alkyl, $C_{1-3}$-alkyl-carbonylamino-$C_{1-3}$-alkyl, phthalimido, pyrrolyl or mono- or di-($C_{1-3}$-alkyl)-pyrrolyl groups, while the substituents are identical or different, and $R^3$ denotes a $C_{3-8}$-cycloalkyl group, a cyclohexyl, cyclohexenyl, cycloheptyl, cyclooctyl, cyclopentenyl or cyclopentyl group which is substituted by a hydroxy, $C_{1-3}$-alkoxy, $C_{1-3}$-alkyl, amino, $C_{1-3}$-alkyl-amino, di-($C_{1-3}$-alkyl)-amino, $C_{1-4}$-alkyloxy-carbonyl-amino, di-($C_{1-3}$-alkyl)-amino-$C_{1-3}$-alkyl, N-($C_{1-3}$-alkyl)-N-(phenyl-$C_{1-3}$-alkyl)-amino-$C_{1-3}$-alkyl, piperidino-$C_{1-3}$-alkyl, piperazino-$C_{1-3}$-alkyl, 4-($C_{1-3}$-alkyl)-piperazino-$C_{1-3}$-alkyl, pyrrolidino-$C_{1-3}$-alkyl, 2-oxo-pyrrolidino-$C_{1-3}$-alkyl, morpholino-$C_{1-3}$-alkyl, carboxy, $C_{1-4}$-alkoxy-carbonyl, di-($C_{1-3}$-alkyl)-amino-$C_{1-3}$-alkyl-aminocarbonyl, amino-$C_{1-3}$-alkyloxy, $C_{1-3}$-alkyl-amino-$C_{1-3}$-alkyloxy, di-($C_{1-3}$-alkyl)-amino-$C_{1-3}$-alkyloxy or ethylenedioxy group, a cyclopentyl or cyclohexyl group wherein the methylene group in position 3 or 4 is replaced in each case by an oxygen or a sulphur atom, a sulphonyl group or a sulphinyl group, a cyclohexyl group which is substituted by a $C_{1-3}$-alkyl and a hydroxy group, a 5- to 7-membered cycloalkyleneimino group wherein the methylene group in the 4 position may be replaced by an oxygen or a sulphur atom, a sulphonyl group or a sulphinyl group, a piperidin-4-yl, piperidin-3-yl, homopiperidin-4-yl or pyrrolidin-3-yl group which may be substituted at the aminonitrogen atom by a straight-chain or branched $C_{1-5}$-alkyl, benzyl, $C_{1-5}$-alkyl-carbonyl, $C_{1-5}$-alkyl-sulphonyl, phenyl-carbonyl, phenyl-sulphonyl, hydroxycarbonyl-$C_{1-3}$-alkyl, morpholinocarbonyl-$C_{1-3}$-alkyl, $C_{1-4}$-alkoxy-carbonyl-$C_{1-3}$-alkyl, $C_{1-4}$-alkoxy-carbonyl, di-($C_{1-3}$alkyl)-amino-carbonyl, $C_{1-5}$-alkyl-amino-carbonyl, $C_{1-3}$-alkylamino-sulphonyl, $C_{1-4}$-alkoxy-carbonyl-$C_{1-3}$-alkyl, di-($C_{1-3}$alkyl)-amino-carbonyl-$C_{1-3}$-alkyl, $C_{1-3}$-alkyl-amino-carbonyl-$C_{1-3}$-alkyl, amino-carbonyl-$C_{1-3}$-alkyl, di-($C_{1-3}$-alkyl)-amino-$C_{1-3}$-alkyl-carbonyl, $C_{1-3}$-alkyl-amino-$C_{1-3}$-alkyl-carbonyl, amino-$C_{1-3}$-alkyl-carbonyl, di-($C_{1-3}$-alkyl)-amino-$C_{1-3}$-alkyl-aminocarbonyl, $C_{1-4}$-alkyloxy-carbonyl-amino-$C_{1-3}$-alkyl-carbonyl, 4-[di-($C_{1-3}$-alkyl)-amino-$C_{1-3}$-alkyloxy]-phenyl-carbonyl, 4-[di-($C_{1-3}$-alkyl)-amino-$C_{1-3}$-alkyloxy]-phenyl-$C_{1-3}$-alkyl-carbonyl or pyrrolidino-$C_{1-3}$-alkyl-carbonyl group, a piperidin-4-yl group which is substituted in the carbon skeleton by one to four $C_{1-3}$-alkyl groups, such as a 2,2,6,6-tetramethyl-piperidin-4-yl group or a 2,6-dimethyl-piperidin-4-yl group, a piperidin-1-yl group which may be substituted in the carbon skeleton by one to four $C_{1-3}$-alkyl groups, a piperazinyl group which may be substituted in the 4 position by a $C_{1-3}$-alkyl group, while the alkyl group may be substituted from position 2 by a hydroxy group, or a 6-methyl-6-aza-bicyclo[3.1.1]heptanyl or 8-methyl-8-aza-bicyclo[3.2.1.]octanyl group, while the above-mentioned alkyl groups may be straight-chain or branched, the tautomers, enantiomers, diastereomers, the mixtures thereof and the salts thereof.

Unless otherwise stated, by a 5-membered heteroaryl group is preferably meant a furanyl, thiophenyl, pyrrolyl, pyrazolyl, thiazolyl, imidazolyl, oxazolyl, triazolyl or thiadiazolyl group, and by a 6-membered heteroaryl group is meant a pyridinyl, pyrimidinyl, pyridazinyl or pyrazinyl group.

By an aryl group is meant, unless otherwise stated, a phenyl or naphthyl group; the phenyl group is preferred.

Unless otherwise stated, the alkyl groups mentioned may always be straight-chain or branched; thus, by a butyl group is meant both an n-butyl and an iso- or tert-butyl group.

Preferred compounds of general formula I are those wherein $R^2$ and $R^3$ are as hereinbefore defined and $R^1$ denotes a methyl, ethyl, propyl, or phenyl group, the tautomers, enantiomers, diastereomers, the mixtures thereof and the salts thereof.

Particularly preferred are those compounds of general formula I wherein $R^1$ denotes a methyl, ethyl, propyl or phenyl group, $R^2$ denotes a pyridinyl, pyrazinyl or furanyl group, a straight-chain or branched $C_{1-7}$-alkyl group, a phenyl group wherein two adjacent carbon atoms are linked together through a methylenedioxy, ethylenedioxy or difluoromethylenedioxy group, or a phenyl group which may be substituted by one or two fluorine, chlorine, bromine or iodine atoms or by one or two $C_{1-3}$-alkyl, nitro, cyano, amino, $C_{1-3}$-alkyl-carbonylamino, phenylcarbonylamino, $C_{1-3}$-alkylsulphonylamino, trifluoromethyl, carboxy, $C_{1-3}$-alkoxy, di-($C_{1-3}$-alkyl)-amino-$C_{1-3}$-alkyloxy, $C_{1-3}$-alkoxy-carbonyl, $C_{1-3}$-alkylaminocarbonyl, hydroxycarbonyl-$C_{1-3}$-alkyl-aminocarbonyl, $C_{1-3}$-alkoxy-carbonyl-$C_{1-3}$-alkyl-aminocarbonyl, di-($C_{1-3}$-alkyl)-amino-$C_{1-3}$-alkylaminocarbonyl, carboxy-$C_{1-3}$-alkyl, $C_{1-3}$-alkoxy-carbonyl-$C_{1-3}$-alkyl, amino-$C_{1-3}$-alkyl or $C_{1-3}$-alkyl-carbonyl-amino-$C_{1-3}$-alkyl groups, while the substituents are identical or different, and $R^3$ denotes a $C_{3-7}$-cycloalkyl group, a cyclohexyl group which is substituted by a di-($C_{1-3}$-alkyl)-amino, di-($C_{1-3}$-alkyl)-amino-$C_{1-3}$-alkyl, carboxy, di-($C_{1-3}$-alkyl)-amino-$C_{1-3}$-alkyl-aminocarbonyl, amino-$C_{1-3}$-alkyloxy, N-($C_{1-3}$-alkyl)-N-(phenyl-$C_{1-3}$-alkyl)-amino-$C_{1-3}$-alkyl, piperidino-$C_{1-3}$-alkyl, piperazino-$C_{1-3}$-alkyl, 4-($C_{1-3}$-alkyl)-piperazino-$C_{1-3}$-alkyl, pyrrolidino-$C_{1-3}$-alkyl, 2-oxo-pyrrolidino-$C_{1-3}$-alkyl, morpholino-$C_{1-3}$-alkyl or di-($C_{1-3}$-alkyl)-amino-$C_{1-3}$-alkyloxy group, a cyclohexyl group wherein the methylene group in the 4 position is replaced by a sulphur atom, a piperidinyl group which may be substituted at the amino-nitrogen atom by a $C_{1-3}$-alkyl, benzyl, carboxy, hydroxycarbonyl-$C_{1-3}$-alkyl, $C_{1-4}$-alkoxy-carbonyl, di-($C_{1-3}$-alkyl)-amino-$C_{1-3}$-alkyl-carbonyl or di-($C_{1-3}$-alkyl)-amino-$C_{1-3}$-alkyl-aminocarbonyl group, or a 4-($C_{1-3}$-alkyl)-piperazinyl group, while the above-mentioned alkyl groups may be straight-chain or branched, the tautomers, enantiomers, diastereomers, the mixtures thereof and the salts thereof.

Most particularly preferred are those compounds of general formula I, wherein $R^1$ denotes a methyl or ethyl group, $R^2$ denotes a furanyl group, an ethyl, propyl, butyl or pentyl group, a phenyl group wherein two adjacent carbon atoms are linked together through a methylenedioxy or ethylenedioxy group, or a phenyl group which may be substituted by one or two methoxy groups, and $R^3$ denotes a cyclohexyl group which is substituted by a dimethylamino group, a cyclohexyl group wherein the methylene group in the 4 position is replaced by a sulphur atom, or a piperidinyl group which is substituted at the amino-nitrogen atom by a $C_{1-3}$-alkyl group, while the above-mentioned alkyl groups may be straight-chain or branched, the tautomers, enantiomers, diastereomers, the mixtures thereof and the salts thereof;

particular mention should be made of the following compounds of general formula I:

(a) 5-acetyl-3-[benzo[1,3]dioxol-5-yl-(1-methyl-piperidin-4-ylamino)-methylidene]-2-indolinone

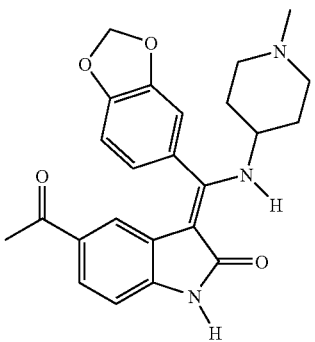

(b) 5-acetyl-3-[phenyl-(1-methyl-piperidin-4-ylamino)-methylidene]-2-indolinone

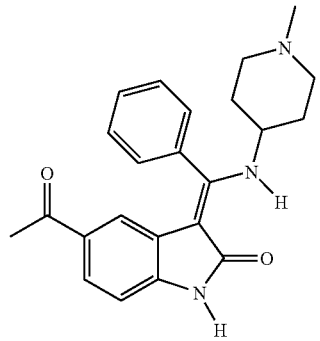

(c) 5-acetyl-3-[phenyl-(1-ethyl-piperidin-4-ylamino)-methylidene]-2-indolinone

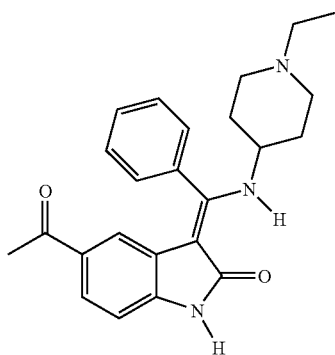

(d) 5-acetyl-3-[phenyl-(1-propyl-piperidin-4-ylamino)-methylidene]-2-indolinone

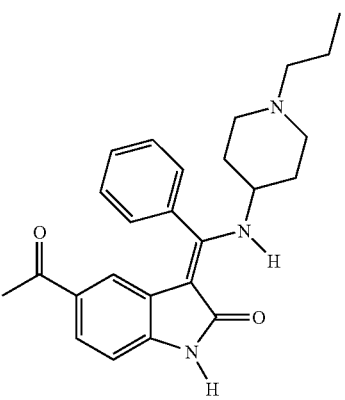

(e) 5-acetyl-3-[(1-methyl-piperidin-4-ylamino)-(2,3-dihydro-benzo[1,4]dioxin-6-yl)-methylidene]-2-indolinone

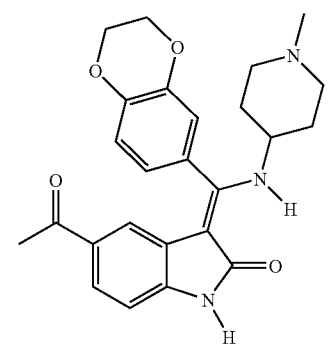

(f) 5-acetyl-3-[benzo[1,3]dioxol-5-yl-(1-ethyl-piperidin-4-ylamino)-methylidene]-2-indolinone

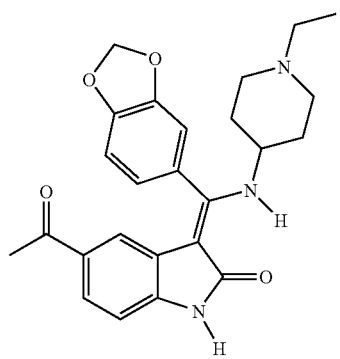

(g) 5-acetyl-3-[4-methoxy-phenyl-(4-trans-dimethylamino-cyclohexylamino)-methylidene]-2-indolinone

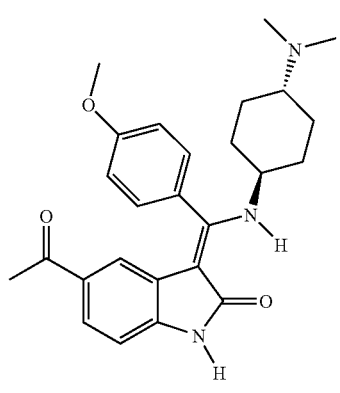

(h) 5-acetyl-3-[4-methoxy-phenyl-(1-methyl-piperidin-4-ylamino)-methylidene]-2-indolinone

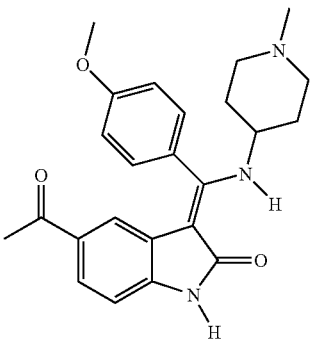

(i) 5-acetyl-3-[3-methoxy-phenyl-(1-methyl-piperidin-4-ylamino)-methylidene]-2-indolinone

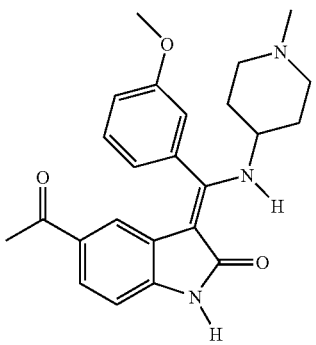

(j) 5-acetyl-3-[3,5-dimethoxy-phenyl-(1-methyl-piperidin-4-ylamino)-methylidene]-2-indolinone

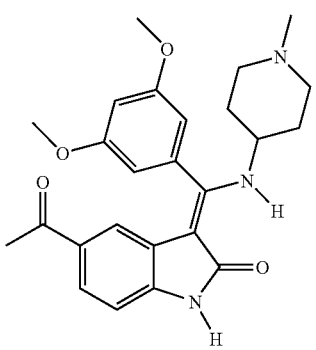

(k) 5-acetyl-3-[phenyl-(tetrahydrothiopyran-4-ylamino)-methylidene]-2-indolinone

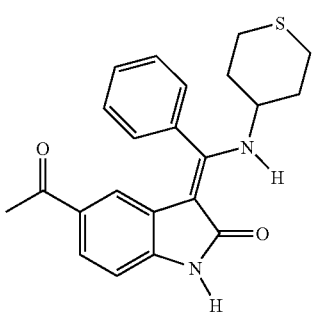

(l) 5-propionyl-3-[benzo[1,3]dioxol-5-yl-(trans-4-dimethylamino-cyclohexylamino)-methylidene]-2-indolinone

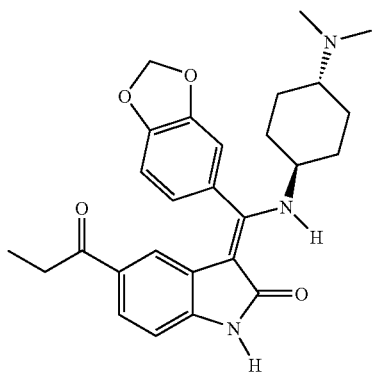

(m) 5-acetyl-3-[furan-3-yl-(1-methyl-piperidin-4-ylamino)-methylidene]-2-indolinone

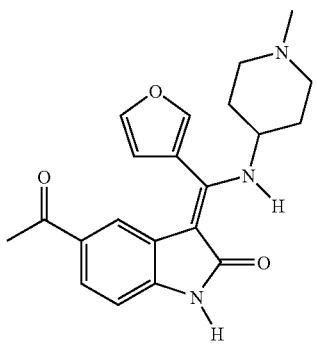

(n) 5-acetyl-3-[1-phenyl-(trans-4-dimethylaminomethyl-cyclohexylamino)-methylidene]-2-indolinone

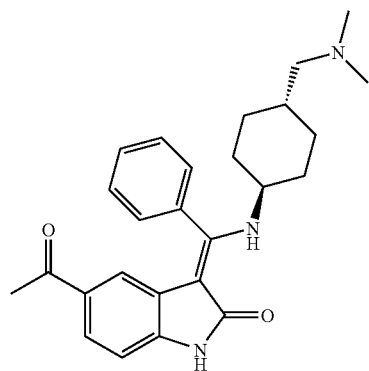

(o) 5-acetyl-3-[(trans-4-dimethylamino-cyclohexylamino)-propylidene]-2-indolinone

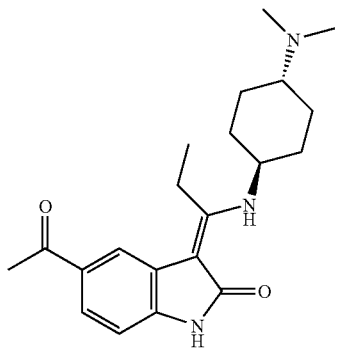

(p) 5-acetyl-3-[1-methyl-piperidin-4-ylamino)-propylidene]-2-indolinone

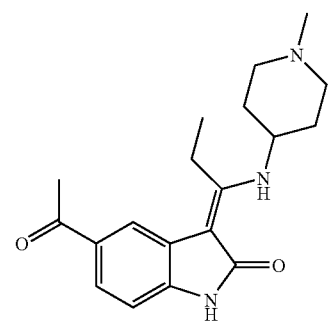

(q) 5-acetyl-3-[4-trifluoromethyl-phenyl-(trans-4-dimethylamino-cyclohexylamino)-methylidene]-2-indolinone

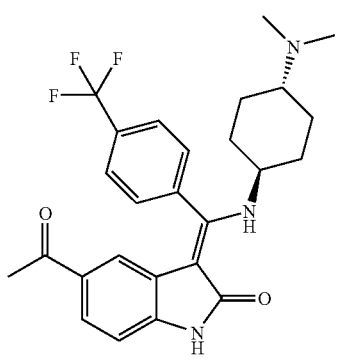

as well as the tautomers, enantiomers, diastereomers, the mixtures thereof and the salts thereof.

According to the invention the compounds of general formula I are obtained by methods known per se, for example by the following methods:

a) reacting a compound of general formula

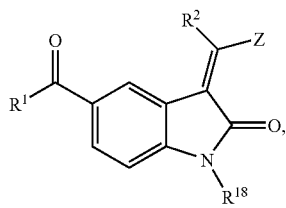

(II)

wherein $R^1$ and $R^2$ are as hereinbefore defined,
$R^{18}$ denotes a hydrogen atom or a protective group for the nitrogen atom of the lactam group and
Z denotes a leaving group such as for example a halogen atom, a hydroxy, alkoxy, alkylsulphonyl, alkyl-arylsulphonyl, trialkylsilyloxy or aryl-alkoxy group, e.g. a chlorine or bromine atom, a methoxy, ethoxy, methanesulphonyl, toluenesulphonyl, trimethylsilyloxy or benzyloxy group,
with an amine of general formula $R^3$—$NH_2$ (III), wherein $R^3$ is as hereinbefore defined,
while any hydroxy, amino or imino groups contained in the groups $R^2$ and/or $R^3$ may be temporarily protected by suitable protective groups;
and if necessary subsequently cleaving any protective group used for the nitrogen atom of the lactam or imino group.

A suitable protective group for the nitrogen atom of the lactam group may be for example an acetyl, benzoyl, ethoxycarbonyl, tert.butyloxycarbonyl or benzyloxycarbonyl group and The reaction is expediently carried out in a solvent such as dimethylformamide, toluene, acetonitrile, tetrahydrofuran, dimethylsulphoxide, methylene chloride or mixtures thereof, optionally in the presence of an inert base such as triethylamine, N-ethyl-diisopropylamine or sodium hydrogen carbonate at temperatures between 20 and 175° C., while any protective group used may simultaneously be cleaved.

If Z in a compound of general formula II denotes a halogen atom, then the reaction is preferably carried out in the presence of an inert base at temperatures between 20 and 120° C.

If Z in a compound of general formula II denotes a hydroxy, alkoxy or arylalkoxy group, then the reaction is preferably carried out at temperatures between 20 and 200° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide or potassium hydroxide at temperatures between 0 and 100° C., preferably at temperatures between 10 and 50° C., or advantageously by transamidation with an organic base such as ammonia, butylamine, dimethylamine or piperidine in a solvent such as methanol, ethanol, dimethylformamide and mixtures thereof or in an excess of the amine used at temperatures between 0 and 100° C., preferably at temperatures between 10 and 50° C.

b) in order to prepare a compound of formula I which contains an aminocarbonyl group: reacting a compound which contains a carboxy group with the corresponding amine to obtain the corresponding aminocarbonyl compound;

c) in order to prepare a compound of formula I which contains a carbonylamino group: reacting a compound which contains an amino group with the corresponding acid chloride to obtain the corresponding carbonylamino compound;

d) in order to prepare a compound of formula I which contains an aminomethyl group: hydrogenation of a compound which contains a cyano group to obtain the corresponding aminomethyl derivative;

e) in order to prepare a compound of formula I which contains an amino group: reduction of a compound which contains a nitro group.

Then any protective groups optionally used during the reaction may be cleaved and/or the compounds of general formula I thus obtained may be resolved into their enantiomers and/or diastereomers and/or the compounds of formula I obtained may be converted into the salts thereof, particularly for pharmaceutical use into the physiologically acceptable salts thereof with inorganic or organic acids or bases.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

The compounds of general formulae II to III used as starting materials are either known from the literature or may be obtained by methods known from the literature (cf. Examples I to XI).

As already mentioned hereinbefore, the compounds according to the invention of general formula I and the physiologically acceptable salts thereof have valuable pharmacological properties, particularly an inhibiting effect on the enzyme GSK-3.

Glycogen synthase kinase-3 (GSK-3) is a serine/threonine kinase which exists in two isoforms, GSK-3α and GSK-3β. GSK-3 phosphorylates and inactivates not only glycogen synthase, a key enzyme of the insulin-dependent regulation of glycogen synthesis (Embi et al., Eur. J. Biochem. 107, 519-527, (1980)), but also a number of other regulatory proteins in vitro. These proteins include the microtubule associated protein Tau, elongation initiation factor 2b (elF2b), β-catenin, axin, ATP-citratelyase, heat-shock-factor 1, c-jun, c-myc, c-myb, CREB and CEBPα. These different substrates imply a role for GSK-3 in numerous fields of cell metabolism, proliferation, differentiation and development.

Type 2 diabetes is characterised by insulin resistance in various tissues such as skeletal muscle, liver and fatty tissue and by altered secretion of insulin from the pancreas. The storage of glycogen in liver and muscle is of great importance for maintaining the glucose equilibrium. In type 2 diabetes the activity of glycogen synthase is reduced and thus the rate of glycogen synthesis is reduced. It has also been shown that GSK-3 is expressed to a greater extent in type 2 diabetic muscle and hence a reduced GSK-3 activity is associated with a reduced rate of glycogen synthesis (Nikoulina et al., diabetes 49, 263-271, (2000)). Inhibition of the GSK-3 activity stimulates glycogen synthase, thus intensifies glycogen synthesis and leads eventually to a reduction in the glucose levels. GSK-3 inhibition is therefore of therapeutic relevance for the treatment of type 1 and type 2 diabetes and also diabetic neuropathy.

Alzheimer's disease is characterised inter alia in that the microtubule-associated protein Tau is present in excessively strongly phosphorylated form (Cohen & Frame, Nature Reviews: Molecular Cell Biology, 2, 1-8, (2001)). GSK-3 phosphorylates many of these phosphorylation sites of Tau in vitro, thereby preventing binding to microtubules. As a result, Tau is available for increased filament assembly, which is at the root of Alzheimer's disease and other neurological diseases of neuronal degeneration. It has been shown that GSK-3 inhibitors such as insulin or lithium bring about partial dephosphorylation of Tau in neuronal cells (Cross et al., J. Neurochem. 77, 94-102 (2001)). GSK-3 inhibition may therefore be of therapeutic relevance for the treatment of degenerative neurological diseases such as Alzheimer's disease.

Inhibitors of GSK-3 activity may thus be of therapeutical and/or preventive benefit for a number of diseases where it is useful to inhibit GSK-3, such as diabetes and diabetes-associated diseases, chronic neurodegenerative diseases and dementias, such as Alzheimer's disease, Parkinson's syndrome, Pick's disease, dementia in subcortical arteriosclerotic encephalopathy (SAE), Huntington's chorea, multiple sclerosis, infectious diseases (meningoencephalitis, syphilis, brain abscess, Creutzfeldt-Jakob disease, AIDS), dementia complex with Lewy bodies, neurotraumatic diseases such as acute stroke, schizophrenia, manic depression, brain haemorrhage, alopecia, obesity, atherosclerotic cardiovaskular diseases, high blood pressure, PCO syndrome, metabolic syndrome, ischaemia, cancer, leuko-penia, Down's syndrome, inflammations, immunodeficiency.

A new study (Sato, N. et al., Nature Medicine 10, 55-63 (2004)) shows that GSK-3 inhibitors may acquire the pluripotence of stem cells, which may open up new possibilities in the field of regenerative therapies using stem cells.

Determining the GSK-3 Activity

The effect of substances on the GSK-3 activity was carried out according to the following test method, based on the phosphorylation of a 26 mer peptide (YR-RAAVPPSPSLSRHSSFHQpSEDEEE) from glycogen synthase, the sequence of which contains the phosphorylation sites for GSK-3 and the prephosphorylation of which is indicated by (pS).

The test substance is dissolved in DMSO/water. GSK3β (University of Dundee, UK) dissolved in 10 mM MOPS (morpholinopropanesulphonic acid), 0.05 mM EDTA, 0.005% Brij, 2.5% glycerol, 0.05% mercaptoethanol, pH 7.0, is combined with 10 μM [$^{33}$P]-ATP, 0.25 μM of 26 mer peptide and incubated with the dissolved substance in 50 mM tris, 10 mM $MgCl_2$, 0.1% mercaptoethanol, pH 7.5, at ambient temperature. The reaction was stopped by the addition of 75 mM phosphoric acid. The reaction mixture was transferred onto Phosphocellulose filter plates (Millipore) and filtered to dryness and washed twice with 75 mM phosphoric acid. The phosphorylation was determined by measuring the radioactivity on the filter in a scintillation counter (Topcount, Packard). The ability of a substance to inhibit GSK-3 is determined by comparing the signal of a reaction mixture containing various concentrations of the substance with the signal of the reaction mixture without any substance. The $IC_{50}$ values are calculated by non-linear regression analysis using GraphPad Prism software.

Typical $IC_{50}$ values for the substances investigated were between 0.0001 μM and 1 μM.

Determining Glycogen Synthesis

This test serves to investigate the effect of test substances on glycogen synthesis in cells.

C3A hepatoma cells (ATCC) are seeded at a density of 100000 cells/ml in 96-well plates and grown to confluence as a monolayer in the medium. The medium is removed and the cells are washed several times with PBS and then incubated in KRBH buffer (134 mM NaCl, 3.5 mM KCl, 1.2 mM $KH_2PO_4$, 0.5 mM $MgSO_4$, 1.5 mM $CaCl_2$, 5 mM $NaHCO_3$, 10 mM HEPES, pH 7.4) with 0.1% BSA and 0.5 mM glucose for 60 min at 37° C. Test substance and 0.2 μCi D-[U$^{14}$C]glucose (Amersham) are added and the cells are incubated for a further 60 min under the same conditions. After the removal of the incubation buffer the cells are washed several times with cold PBS and then lysed for 10 min at 37° C. and 10 min at ambient temperature with 1 M NaOH. The cell lysates are transferred onto filter plates and the glycogen is precipitated by incubating for 2 h with cold ethanol (70%) on ice. The precipitates are washed several times with ethanol and filtered to dryness. The glycogen synthesised is determined by measuring the radioactivity (14C-glucose incorporated) on the filter plates in a scintillation counter (Topcount, Packard).

The ability of a substance to stimulate glycogen synthesis is determined by comparing the signal of a reaction mixture containing various concentrations of the substance with the signal of the reaction mixture without any substance.

Oral Glucose Tolerance Test

Fasted db/db mice 7 to 9 weeks old (Janvier, France) are weighed and blood is taken from the tip of the tail. This blood is used for the first measurement of glucose on the basis of which the animals are randomised and divided into groups. The test substance to be tested may be given either orally or i.p. as a suspension in 0.5% Natrosol. 30 minutes after the administration of the substance the animals are given orally 2 g/kg glucose in a volume of 0.1 ml/100 g body weight dissolved in NaCl solution. Subsequently, the glucose values are determined from the tail blood using a glucometer (Ultra OneTouch, Lifescan) at specific time intervals [30, 60, 120 and 180 minutes after oral administration of the glucose].

For example, compound 1 exhibits a significant activity in the oral glucose tolerance-test.

The compounds prepared according to the invention are well tolerated as, for example, after oral administration of 10 mg/kg of the compound of Example 1 to rats no changes were observed in the animals' behaviour.

The compounds according to the invention may also be used in combination with other active substances. Therapeutic agents which are suitable for such a combination include, for example, antidiabetic agents such as metformin, sulphonylureas (e.g. glibenclamid, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPP-IV inhibitors, alpha2-antagonists, insulin and insulin analogues, GLP-1 and GLP-1 analogues (e.g. exendin-4) or amylin. The list also includes SGLT2-inhibitors such as T-1095, inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

In addition, combinations with drugs for influencing high blood pressure such as e.g. A-II antagonists or ACE inhibitors, diuretics, β-blockers, Ca-antagonists and others or combinations thereof are suitable.

Generally speaking, GSK-3 inhibitors may be administered in various ways: by oral, transdermal, intranasal or parenteral route or, in special cases, by intrarectal route. The preferred method of administration is by oral route daily, possibly several times a day. GSK-3 inhibitors are effective over wide dosage range. Thus, the dosage may be between 0.001 and 100 mg/kg, for example.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples that follow are intended to illustrate the invention:

Preparation of the starting compounds:

EXAMPLE I 5-acetyl-2-indolinone

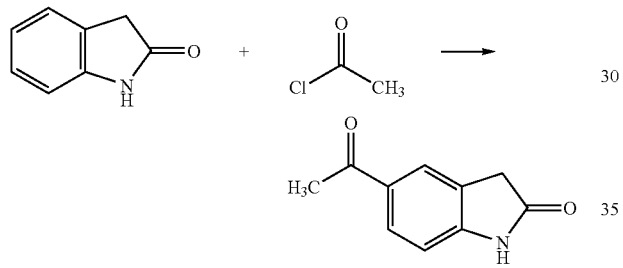

171 g (1.28 mol) of aluminium chloride are cooled in 500 ml of 1,2-dichloroethane in the ice bath. Then 78 g (1.1 mol) acetyl chloride are added dropwise, so that the temperature does not exceed 10° C. After 1 h 71.3 g (0.53 mol) 2-indolinone (1,3-dihydro-indol-2-one) are added in 4 batches and the temperature is kept at 10-12° C. The reaction mixture is allowed to come up to ambient temperature slowly overnight. Then the solution is slowly added to 1 kg of ice with vigorous stirring. The slurry is with diluted 1 l water and stirred for another 30 min. Then the precipitate is suction filtered.

Yield: 80.9 g (86.3% of theory)
$R_f$=0.36 (silica gel, ethyl acetate/cyclohexane/methanol 9:9:2)
$C_{10}H_9NO_2$ (MG=175.19)
Mass spectrum: m/z=174 (M–H)$^-$ The following compounds are prepared analogously to Example I:

(1) 5-propionyl-2-indolinone
Prepared from 2-indolinone and propionyl chloride
Yield: 72% of theory
$R_f$=0.44 (silica gel, methylene chloride/methanol 9:1)
$C_{11}H_{11}NO_2$ (MW=189.22)
Mass spectrum: m/z=188 (M–H)$^-$ (2) 5-butyryl-2-indolinone
Prepared from 2-indolinone and butyric acid chloride (butyryl chloride)
Yield: 68% of theory
$C_{12}H_{13}NO_2$ (MW=203.24)
Mass spectrum: m/z=202 (M–H)$^-$ (3) 5-isobutyryl-2-indolinone
Prepared from 2-indolinone and isobutyryl chloride
Yield: 13% of theory
$C_{12}H_{13}NO_2$ (MW=203.24)
Mass spectrum: m/z=202 (M–H)$^-$ (4) 5-hexanoyl-2-indolinone
Prepared from 2-indolinone and hexanoic acid chloride
Yield: 88% of theory
$R_f$=0.51 (silica gel, ethyl acetate/cyclohexane/methanol 9:9:2)
$C_{14}H_{17}NO_2$ (MW=231.30)
Mass spectrum: m/z=230 (M–H)$^-$ (5) 5-benzoyl-2-indolinone
Prepared from 2-indolinone and benzoic acid chloride
Yield: 80% of theory
$R_f$=0.46 (silica gel, methylene chloride/methanol 9:1)
$C_{15}H_{11}NO_2$ (MW=237.26)
Mass spectrum: m/z=236 (M–H)$^-$

EXAMPLE II 1,5-diacetyl-2-indolinone 48.9 g (0.279 mol) 5-acetyl-2-indolinone are stirred for 2 h in 400 ml acetic anhydride in an oil bath at 140° C. The starting material dissolves.

Then the reaction mixture is left to cool, evaporated down, the precipitate is removed by suction filtering, washed with diethylether and the product is dried.

Yield: 56.0 g (92.4% of theory)
$R_f$=0.41 (silica gel, methylene chloride/methanol 50:1)
$C_{12}H_{11}NO_3$ (MW=217.223)
Mass spectrum: m/z=216 (M–H)$^-$ The following compounds are prepared analogously to Example II:

(1) 1-acetyl-5-propionyl-2-indolinone
Prepared from 5-propionyl-2-indolinone and acetic anhydride
Yield: 79% of theory
$R_f$=0.68 (silica gel, methylene chloride/methanol 9:1)
$C_{13}H_{13}NO_3$ (MW=231.25)
Mass spectrum: m/z=232 (M+H)$^+$ (2) 1-acetyl-5-benzoyl-2-indolinone Prepared from 5-benzoyl-2-indolinone and acetic anhydride Yield: 89% of theory $R_f$=0.60 (silica gel, methylene chloride/methanol 30:1)

$C_{17}H_{13}NO_3$ (MW=279.294)

Mass spectrum: m/z=278 (M–H)⁻

(3) 1-acetyl-5-hexanoyl-2-indolinone

Prepared from 5-hexanoyl-2-indolinone and acetic anhydride $R_f$=0.74 (silica gel, methylene chloride/methanol 30:1)

$C_{16}H_{19}NO_3$ (MW=273.33)

Mass spectrum: m/z=272 (M–H)⁻

EXAMPLE III 1,5-diacetyl-3-(ethoxy-phenyl-methylidene)-2-indolinone

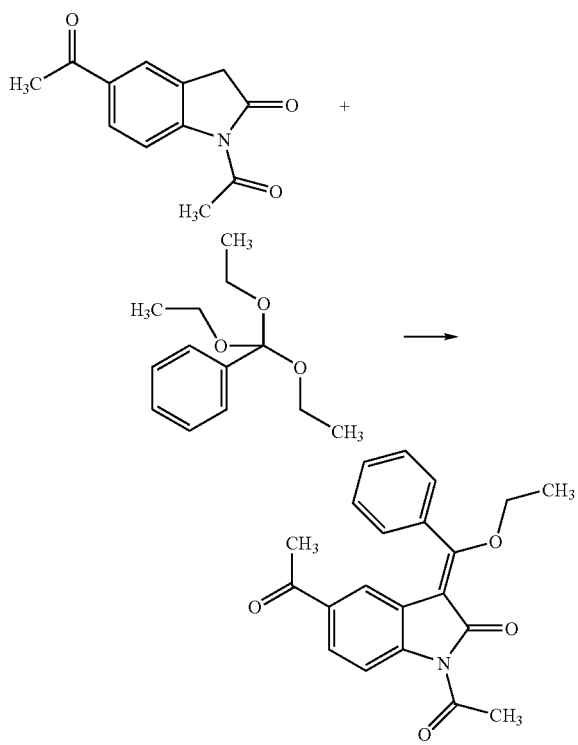

32.6 g (150 mmol) of 1,5-diacetyl-2-indolinone are suspended in 100 ml triethyl orthobenzoate and stirred overnight at 110° C. with 150 ml acetic anhydride. Then a further 50 ml of triethyl orthobenzoate are added and the mixture is stirred for a further 24 h. Then it is evaporated down and the resulting precipitate is suction filtered, washed and dried.

Yield: 38 g (72.5% of theory)

$R_f$=0.60 (silica gel, methylene chloride/methanol 30:1)

$C_{21}H_{19}NO_4$ (MW=349.384)

Mass spectrum: m/z=350 (M+H)⁺

The following compounds are prepared analogously to Example III:

(1) 1-acetyl-5-hexanoyl-3-(ethoxy-phenyl-methylidene)-2-indolinone

Prepared from 1-acetyl-5-hexanoyl-2-indolinone and triethyl orthobenzoate

Yield: 29% of theory $R_f$=0.72 (silica gel, methylene chloride/methanol 30:1)

$C_{25}H_{27}NO_4$ (MW=405.491)

Mass spectrum: m/z=428 (M+Na)⁺

(2) 1-acetyl-5-benzoyl-3-(ethoxy-phenyl-methylidene)-2-indolinone

Prepared from 1-acetyl-5-benzoyl-2-indolinone and triethyl orthobenzoate

Yield: 65% of theory $R_f$=0.72 (silica gel, methylene chloride/methanol 30:1)

$C_{26}H_{21}NO_4$ (MW=411.455)

Mass spectrum: m/z=412 (M+H)⁺

(3) 1,5-diacetyl-3-(1-methoxy-propylidene)-2-indolinone

Prepared from 1,5-diacetyl-2-indolinone and trimethyl orthopropionate

Yield: 80% of theory $R_f$=0.50 (silica gel, methylene chloride/methanol 50:1)

$C_{16}H_{17}NO_4$ (MW=287.311)

Mass spectrum: m/z=288 (M+H)⁺

(4) 1,5-diacetyl-3-(1-methoxy-butylidene)-2-indolinone

Prepared from 1,5-diacetyl-2-indolinone and trimethyl orthobutyrate

Yield: 71% of theory $R_f$=0.53 (silica gel, methylene chloride/methanol 50:1)

$C_{17}H_{19}NO_4$ (MW=301.337)

Mass spectrum: m/z=302 (M+H)⁺

(5) 1,5-diacetyl-3-(1-methoxy-pentylidene)-2-indolinone

Prepared from 1,5-diacetyl-2-indolinone and trimethyl orthovalerate

Yield: 66% of theory $R_f$=0.60 (silica gel, methylene chloride/methanol 50:1)

$C_{18}H_{21}NO_4$ (MW=315.364)

Mass spectrum: m/z=316 (M+H)⁺

(6) 1,5-diacetyl-3-(1-methoxy-2-methyl-propylidene)-2-indolinone

Prepared from 1,5-diacetyl-2-indolinone and 1,1,1-trimethoxy-2-methylpropane

Yield: 40% of theory $R_f$=0.71 (silica gel, ethyl acetate:cyclohexane:methanol 9:9:2)

$C_{17}H_{19}NO_4$ (MW=301.337)

Mass spectrum: m/z=302 (M+H)⁺

(7) 1-acetyl-5-propionyl-3-(1-methoxy-propylidene)-2-indolinone

Prepared from 1-acetyl-5-propionyl-2-indolinone and trimethyl orthopropionate (8) 1-acetyl-5-hexanonyl-3-(1-methoxy-propylidene)-2-indolinone Prepared from 1-acetyl-5-hexanoyl-2-indolinone and trimethyl orthopropionate

EXAMPLE IV 1-acetyl-5-butyryl-3-(ethoxy-phenyl-methylidene)-2-indolinone

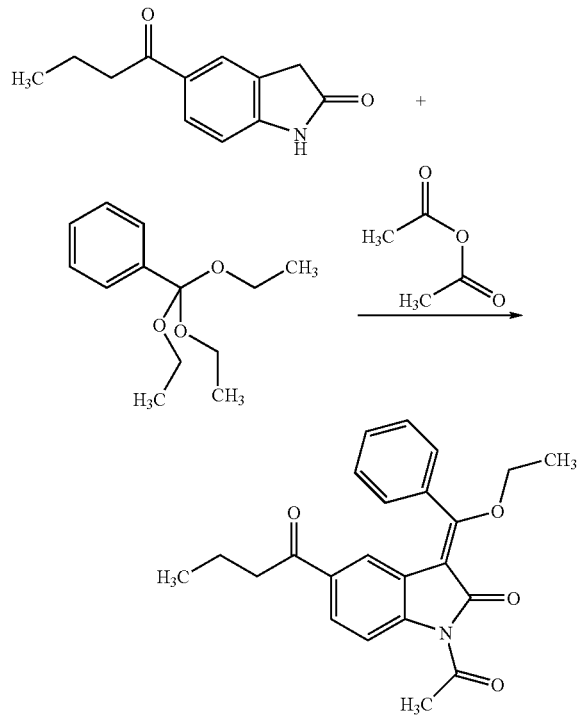

10 g (49 mmol) 5-butyryl-2-indolinone (Ex. 1.2) are stirred for 5 h at 130° C. in 200 m acetic anhydride. Then 35 ml triethyl orthobenzoate are added and the mixture is stirred for a further 4 h at 100° C. Then it is evaporated down and the resulting precipitate is suction filtered, washed and dried.

Yield: 11.5 g (62% of theory)

$R_f$=0.79 (silica gel, ethyl acetate/cyclohexane/methanol 9:9:2)

$C_{23}H_{23}NO_4$ (MW=377.438)

Mass spectrum: m/z=378 (M+H)$^+$

The following compounds are prepared analogously to Example IV:

(1) 1-acetyl-5-isobutyryl-3-(ethoxy-phenyl-methylidene)-2-indolinone

Prepared from 5-isobutyryl-2-indolinone, acetic anhydride and triethyl orthobenzoate $R_f$=0.55 (silica gel, ethyl acetate/cyclohexane/methanol 9:9:2)

(2) 1,5-diacetyl-3-[1-methoxy-ethylidene]-2-indolinone

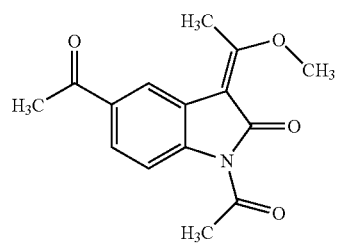

Prepared from 5-acetyl-2-indolinone, acetic anhydride and trimethyl orthoacetate $R_f$=0.40 (silica gel, methylene chloride/methanol 50:1)

(3) 1-acetyl-5-propionyl-3-(ethoxy-phenyl-methylidene)-2-indolinone

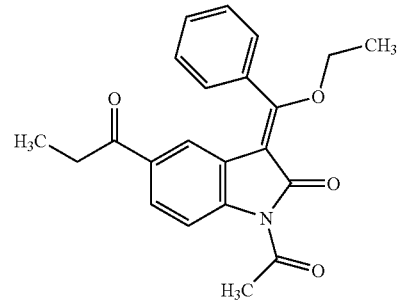

Prepared from 5-propionyl-2-indolinone, acetic anhydride and triethyl orthobenzoate $R_f$=0.79 (silica gel, ethyl acetate/cyclohexane/methanol 9:9:2)

(4) 1-acetyl-5-hexanoyl-3-(ethoxy-phenyl-methylidene)-2-indolinone

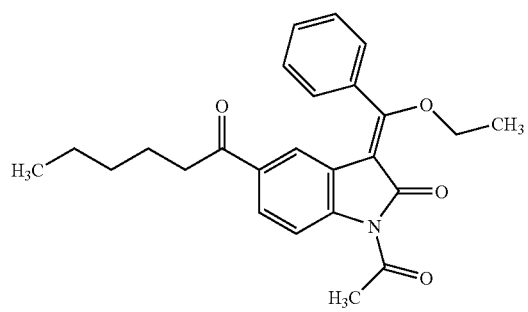

Prepared from 5-hexanoyl-2-indolinone, acetic anhydride and triethyl orthobenzoate $R_f$=0.72 (methylene chloride/methanol 30:1)

(5) 1-acetyl-5-butyryl-3-(ethoxy-phenyl-methylidene)-2-indolinone

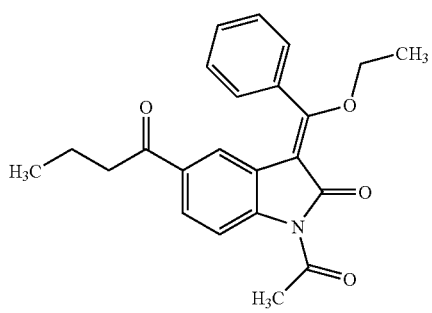

Prepared from 5-butyryl-2-indolinone, acetic anhydride and triethyl orthobenzoate $R_f$=0.79 (silica gel, ethyl acetate/cyclohexane/methanol 9:9:2)

EXAMPLE V 1,5-diacetyl-3-[(3,4-dimethoxy-Phenyl)-hydroxy-methylidene]-2-indolinone

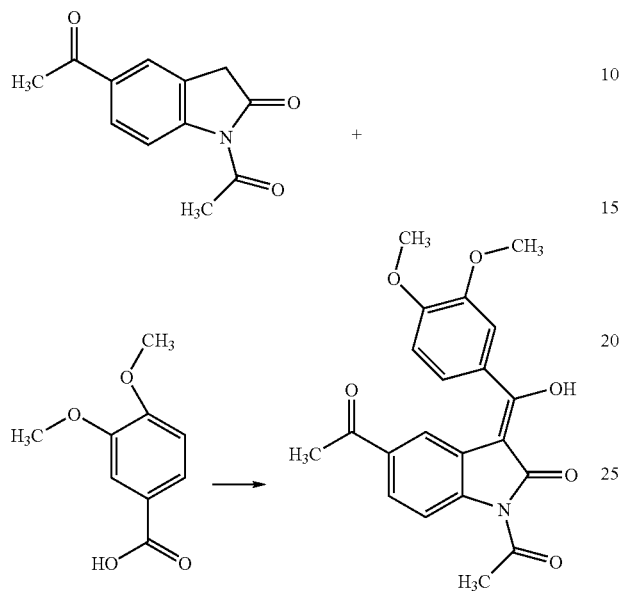

4.3 g (20 mmol) 1,5-diacetyl-2-indolinone (Ex. II) are stirred overnight together with 4 g of 3,4-dimethoxybenzoic acid, 7.1 g TBTU (O-benzotriazol-1-yl-N,N,N',N'-tetramethyluronium tetrafluoroborate) and 14 ml triethylamine in 80 ml DMF (dimethylformamide) at ambient temperature. Then the mixture is poured onto 300 ml ice water with 10 ml of conc. hydrochloric acid and the precipitate formed is suction filtered. The residue is washed with a little methanol and then with ether.

Yield: 6.2 g (81.3% of theory)
$R_f$=0.85 (silica gel, methylene chloride/methanol 9:1)
$C_{21}H_{19}NO_6$ (MW=381.382)
Mass spectrum: m/z=381 (M)$^+$ The following compounds are prepared analogously to Example V:

(1) 1,5-diacetyl-3-[(benzo[1,3]dioxol-5-yl)-hydroxy-methylidene]-2-indolinone

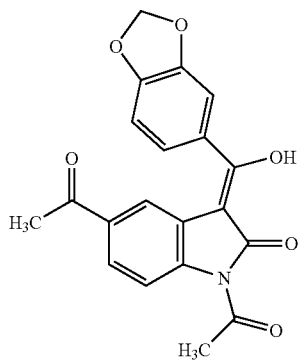

Prepared from 1,5-diacetyl-2-indolinone and piperonylic acid (benzo[1,3]dioxol-5-carboxylic acid)
Yield: 60% of theory
$R_f$=0.70 (silica gel, methylene chloride/methanol 9:1)
$C_{20}H_{15}NO_6$ (MW=365.339)
Mass spectrum: m/z=366 (M+H)$^+$ (2) 1,5-diacetyl-3-[(4-nitro-phenyl)-hydroxy-methylidene]-2-indolinone

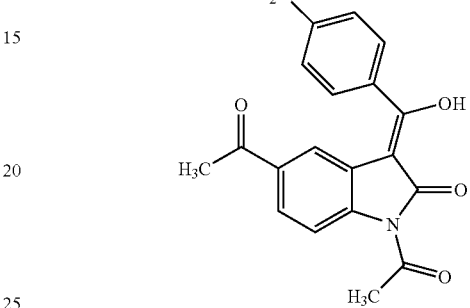

Prepared from 1,5-diacetyl-2-indolinone and 4-nitrobenzoic acid
Yield: 82% of theory
$R_f$=0.38 (silica gel, methylene chloride/methanol 9:1)
$C_{19}H_{14}N_2O_6$ (MW=366.328)
Mass spectrum: m/z=367 (M+H)$^+$ (3) 1,5-diacetyl-3-[(3-nitro-phenyl)-hydroxy-methylidene]-2-indolinone

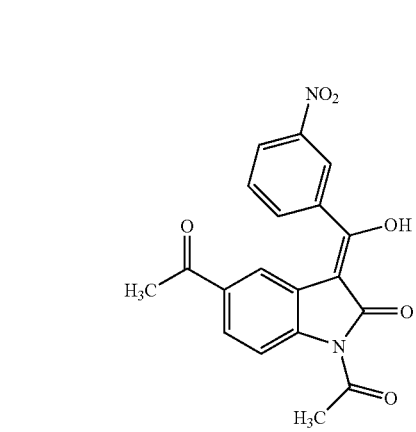

Prepared from 1,5-diacetyl-2-indolinone and 3-nitrobenzoic acid
Yield: 75% of theory
$R_f$=0.38 (silica gel, methylene chloride/methanol 9:1)
$C_{19}H_{14}N_2O_6$ (MW=366.328)
Mass spectrum: m/z=367 (M+H)$^+$ (4) 1,5-diacetyl-3-[(4-methyloxycarbonyl-phenyl)-hydroxy-methylidene]-2-indolinone

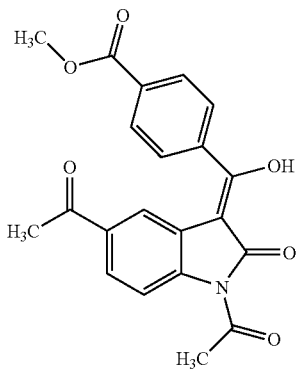

Prepared from 1,5-diacetyl-2-indolinone and monomethyl terephthalate
Yield: 71% of theory
$R_f$=0.41 (silica gel, methylene chloride/methanol 30:1)
$C_{21}H_{17}NO_6$ (MW=379.366)
Mass spectrum: m/z=380 (M+H)$^+$ (5) 1,5-diacetyl-3-[(4-chloro-phenyl)-hydroxy-methylidene]-2-indolinone

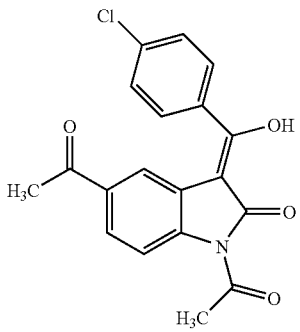

Prepared from 1,5-diacetyl-2-indolinone and 4-chlorobenzoic acid
Yield: 87% of theory
$C_{19}H_{14}ClNO_4$ (MW=355.776)
Mass spectrum: m/z=356/358 (M+H)$^+$ (6) 1,5-diacetyl-3-[(3,4-dichloro-phenyl)-hydroxy-methylidene]-2-indolinone

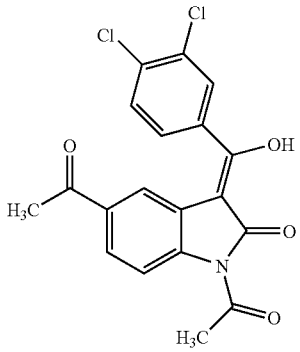

Prepared from 1,5-diacetyl-2-indolinone and 3,4-dichlorobenzoic acid
Yield: 83% of theory
$C_{19}H_{13}Cl_2NO_4$ (MW=390.221)
Mass spectrum: m/z=390/392/394 (M+H)$^+$ (7) 1,5-diacetyl-3-[(4-cyano-phenyl)-hydroxy-methylidene]-2-indolinone

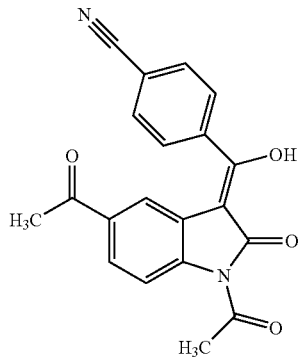

Prepared from 1,5-diacetyl-2-indolinone and 4-cyanobenzoic acid
Yield: 71% of theory
$R_f$=0.32 (silica gel, methylene chloride/methanol 9:1)
$C_{20}H_{14}N_2O_4$ (MW=346.341)
Mass spectrum: m/z=347 (M+H)$^+$ (8) 1,5-diacetyl-3-[(4-trifluoromethyl-phenyl)-hydroxy-methylidene]-2-indolinone

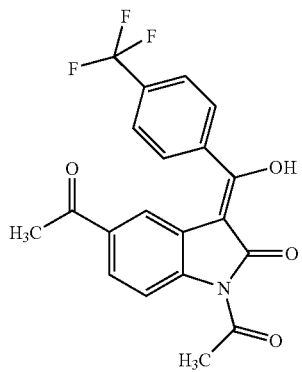

Prepared from 1,5-diacetyl-2-indolinone and 4-trifluoromethyl-benzoic acid
Yield: 83% of theory
$C_{20}H_{14}F_3NO_4$ (MW=389.328)
Mass spectrum: m/z=390 (M+H)$^+$ (9) 1,5-diacetyl-3-[(2,3-dihydro-benzo-[1,4]dioxin-6-yl)-hydroxy-methylidene]-2-indolinone

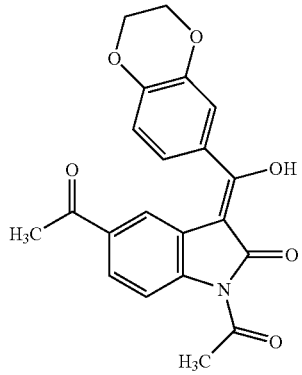

Prepared from 1,5-diacetyl-2-indolinone and 2,3-dihydro-1,4-benzodioxine-6-carboxylic acid
Yield: 90% of theory
$R_f$=0.75 (silica gel, methylene chloride/methanol 9:1)
$C_{21}H_{17}NO_6$ (MW=379.366)
Mass spectrum: m/z=380 (M+H)$^+$

(10) 1,5-diacetyl-3-[(3-methoxy-phenyl)-hydroxy-methylidene]-2-indolinone

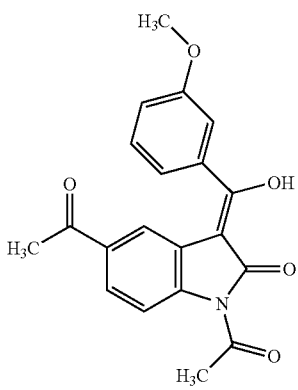

Prepared from 1,5-diacetyl-2-indolinone and 3-methoxybenzoic acid
Yield: 70% of theory
$R_f$=0.67 (silica gel, methylene chloride/methanol 9:1)

(11) 1,5-diacetyl-3-[(4-methoxy-phenyl)-hydroxy-methylidene]-2-indolinone

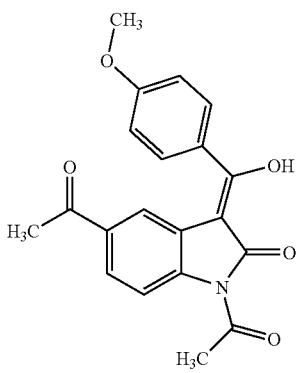

Prepared from 1,5-diacetyl-2-indolinone and 4-methoxybenzoic acid
Yield: 59% of theory
$R_f$=0.39 (silica gel, methylene chloride/methanol 9:1)
$C_{20}H_{17}NO_5$ (MW=351.356)
Mass spectrum: m/z=350 (M–H)$^-$

(12) 1-acetyl-5-propionyl-3-[(benzo[1,3]dioxol-5-yl)-hydroxy-methylidene]-2-indolinone

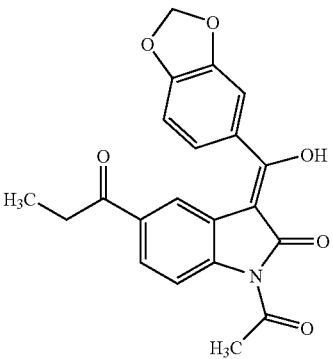

Prepared from 1-acetyl-5-propionyl-2-indolinone and piperonylic acid (benzo[1,3]-dioxol-5-carboxylic acid)
Yield: 67% of theory
$R_f$=0.49 (silica gel, methylene chloride/methanol 30:1)

$C_{21}H_{17}NO_6$ (MW=379.366)
Mass spectrum: m/z=380 (M+H)$^+$

(13) 1,5-diacetyl-3-[(4-bromophenyl)-hydroxy-methylidene]-2-indolinone

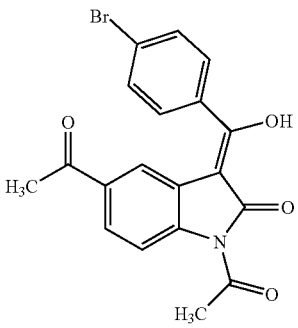

Prepared from 1,5-diacetyl-2-indolinone and 4-bromobenzoic acid
Yield: 89% of theory
$C_{19}H_{14}BrNO_4$ (MW=400.227)
Mass spectrum: m/z=400/402 (M+H)$^+$

(14) 1,5-diacetyl-3-[(3,5-dichloro-phenyl)-hydroxy-methylidene]-2-indolinone

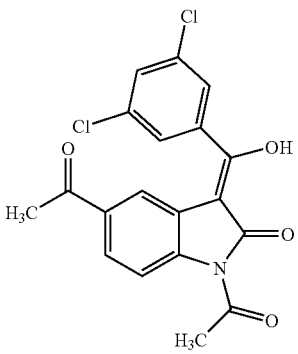

Prepared from 1,5-diacetyl-2-indolinone and 3,5-dichlorobenzoic acid
Yield: 79% of theory
$R_f$=0.26 (silica gel, methylene chloride/methanol 30:1)
$C_{19}H_{13}Cl_2NO_4$ (MW=390.221)
Mass spectrum: m/z=390/392/394 (M+H)$^+$

(15) 1,5-diacetyl-3-[(3,5-dimethoxyphenyl)-hydroxy-methylidene]-2-indolinone

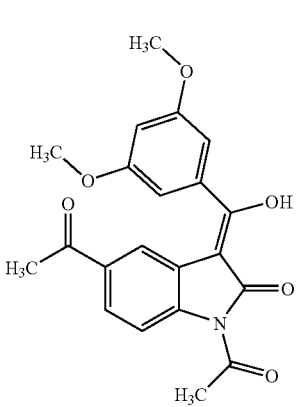

Prepared from 1,5-diacetyl-2-indolinone and 3,5-dimethoxybenzoic acid

Yield: 83% of theory
R_f=0.37 (silica gel, methylene chloride/methanol 30:1)
$C_{21}H_{19}NO_6$ (MW=381.382)
Mass spectrum: m/z=382 (M+H)$^+$

(16) 1,5-diacetyl-3-[(2-chloro-phenyl)-hydroxy-methylidene]-2-indolinone

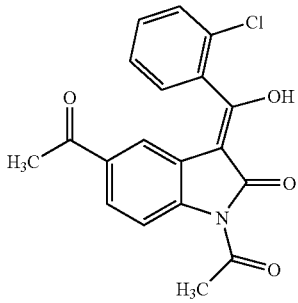

Prepared from 1,5-diacetyl-2-indolinone and 2-chlorobenzoic acid
Yield: 96% of theory
$C_{19}H_{14}ClNO_4$ (MW=355.776)
Mass spectrum: m/z=356/358 (M+H)$^+$

(17) 1,5-diacetyl-3-[(2-methoxy-phenyl)-hydroxy-methylidene]-2-indolinone

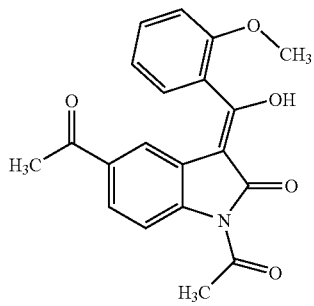

Prepared from 1,5-diacetyl-2-indolinone and 2-methoxybenzoic acid
Yield: 27% of theory
$C_{20}H_{17}NO_5$ (MW=351.356)
Mass spectrum: m/z=352 (M+H)$^+$

(18) 1,5-diacetyl-3-[(2,6-difluoro-phenyl)-hydroxy-methylidene]-2-indolinone

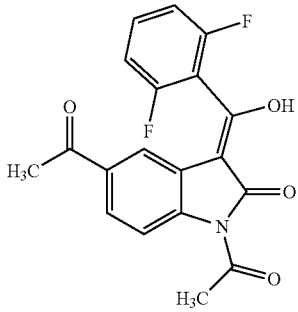

Prepared from 1,5-diacetyl-2-indolinone and 2,6-difluorobenzoic acid
Yield: 52% of theory
$C_{19}H_{13}F_2NO_4$ (MW=357.311)
Mass spectrum: m/z=358 (M+H)$^+$

(19) 1,5-diacetyl-3-[(4-fluorophenyl)-hydroxy-methylidene]-2-indolinone

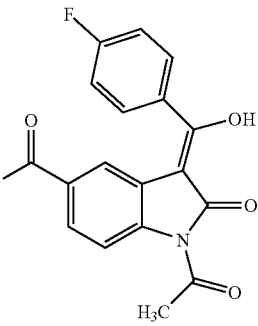

Prepared from 1,5-diacetyl-2-indolinone and 4-fluorobenzoic acid
Yield: 77% of theory
$C_{19}H_{14}FNO_4$ (MW=339.321)
Mass spectrum: m/z=338 (M–H)$^-$

(20) 1,5-diacetyl-3-[(3,4-difluoro-phenyl)-hydroxy-methylidene]-2-indolinone

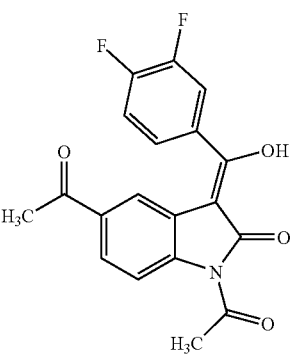

Prepared from 1,5-diacetyl-2-indolinone and 3,4-difluorobenzoic acid
Yield: 91% of theory

(21) 1,5-diacetyl-3-[(2,2-difluoro-benzo[1,3]dioxol-5-yl)-hydroxy-methylidene]-2-indolinone

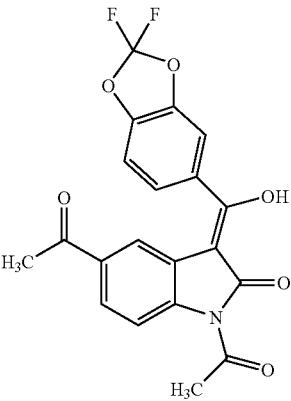

Prepared from 1,5-diacetyl-2-indolinone and 2,2-difluoro-benzo[1,3]dioxol-5-carboxylic acid
Yield: 69% of theory
$C_{20}H_{13}F_2NO_6$ (MW=401.32)
Mass spectrum: m/z=402 (M+H)$^+$

(22) 1,5-diacetyl-3-[(4-(2-methoxycarbonyl-ethyl)-phenyl)-hydroxy-methylidene]-2-indolinone

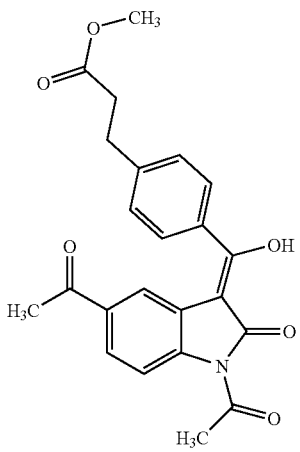

Prepared from 1,5-diacetyl-2-indolinone and 4-(2-methoxycarbonyl-ethyl)-benzoic acid
Yield: 23% of theory
$C_{23}H_{21}NO_6$ (MW=407.42)
Mass spectrum: m/z=408 (M+H)$^+$

(23) 1,5-diacetyl-3-[(pyrazin-2-yl)-hydroxy-methylidene]-2-indolinone

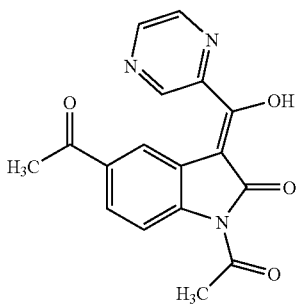

Prepared from 1,5-diacetyl-2-indolinone and pyrazine-2-carboxylic acid
Yield: 57% of theory
$C_{17}H_{13}N_3O_4$ (MW=323.311)
Mass spectrum: m/z=324 (M+H)$^+$

(24) 1,5-diacetyl-3-[(pyridin-4-yl)-hydroxy-methylidene]-2-indolinone

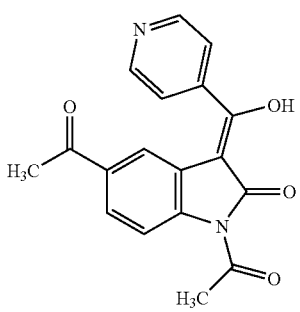

Prepared from 1,5-diacetyl-2-indolinone and isonicotinic acid (pyridine-4-carboxylic acid)
Yield: 87% of theory
$C_{18}H_{14}N_2O_4$ (MW=322.323)
Mass spectrum: m/z=323 (M+H)$^+$

(25) 1,5-diacetyl-3-[(furan-3-yl)-hydroxy-methylidene]-2-indolinone

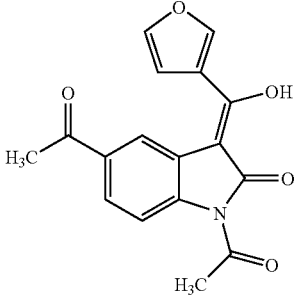

Prepared from 1,5-diacetyl-2-indolinone and furan-3-carboxylic acid
Yield: 73% of theory
$C_{17}H_{13}NO_5$ (MW=311.297)
Mass spectrum: m/z=312 (M+H)$^+$

(26) 1,5-diacetyl-3-[(4-diethylaminomethyl-phenyl)-hydroxy-methylidene]-2-indolinone

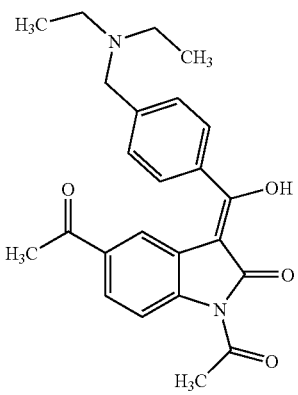

Prepared from 1,5-diacetyl-2-indolinone and 4-diethylaminomethyl-benzoic acid
Yield: 10% of theory
$C_{24}H_{26}N_2O_4$ (MW=406.486)
Mass spectrum: m/z=407 (M+H)$^+$

(27) 1,5-diacetyl-3-[(4-methoxycarbonylmethoxy-phenyl)-hydroxy-methylidene]-2-indolinone

Prepared from 1,5-diacetyl-2-indolinone and 4-methoxycarbonyl-methoxy-benzoic acid
Yield: 43% of theory
$C_{22}H_{19}NO_7$ (MW=409.39)
Mass spectrum: m/z=410 (M+H)$^+$

(28) 1,5-diacetyl-3-[(4-methylsulphonyl-phenyl)-hydroxy-methylidene]-2-indolinone

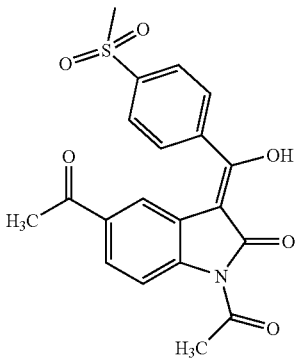

Prepared from 1,5-diacetyl-2-indolinone and 4-methyl-sulphonyl-benzoic acid
Yield: 25% of theory
$C_{20}H_{17}NO_6S$ (MW=399.418)
Mass spectrum: m/z=400 (M+H)$^+$

(29) 1,5-diacetyl-3-[(4-(2-diethylamino-ethoxy)-phenyl)-hydroxy-methylidene]-2-indolinone

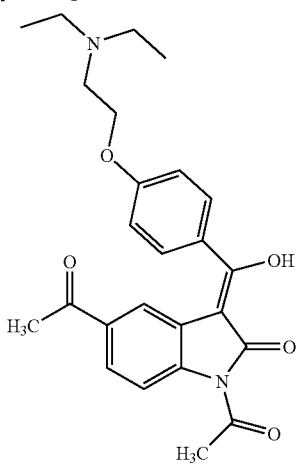

Prepared from 1,5-diacetyl-2-indolinone and 4-diethylamino-ethoxy-benzoic acid
Yield: 27% of theory
$C_{25}H_{28}N_2O_5$ (MW=436.500)
Mass spectrum: m/z=437 (M+H)$^+$

(30) 1,5-diacetyl-3-[(3-(2-diethylamino-ethoxy)-phenyl)-hydroxy-methylidene]-2-indolinone

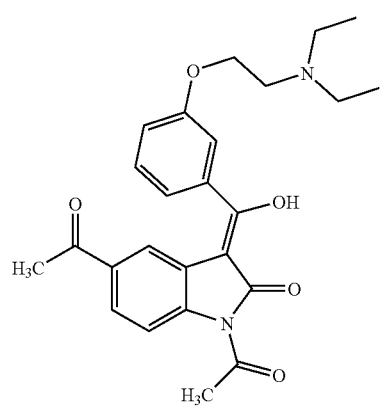

Prepared from 1,5-diacetyl-2-indolinone and 3-diethylamino-ethoxy-benzoic acid
Yield: 43% of theory
$C_{25}H_{28}N_2O_5$ (MW=436.500)
Mass spectrum: m/z=437 (M+H)$^+$

(31) 1,5-diacetyl-3-(1-hydroxy-heptylidene)-2-indolinone

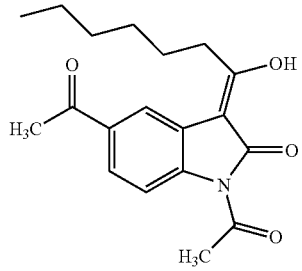

Prepared from 1,5-diacetyl-2-indolinone and heptanoic acid

(32) 1,5-diacetyl-3-(1-hydroxy-hexylidene)-2-indolinone

Prepared from 1,5-diacetyl-2-indolinone and hexanoic acid

(33) 1,5-diacetyl-3-(1-hydroxy-3-methyl-butylidene)-2-indolinone

Prepared from 1,5-diacetyl-2-indolinone and isovaleric acid

EXAMPLE VI 1,5-diacetyl-3-[(3,4-dimethoxy-phenyl)-methoxy-methylidene]-2-indolinone

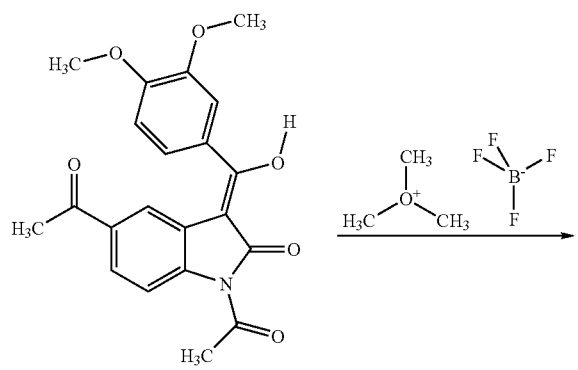

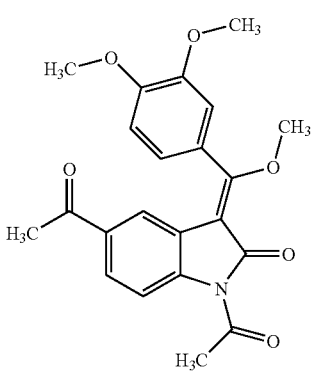

4.0 g (10.5 mmol) 1,5-diacetyl-3-[(3,4-dimethoxy-phenyl)-hydroxy-methylidene]-2-indolinone (Ex. V) are suspended in 100 ml methylene chloride and combined with 3.1 g (21 mmol) trimethyloxonium tetrafluoroborate as well as 7.2 ml Hünig base (ethyldiisopropylamine) at ambient temperature. The solution is stirred for 3 h, then another 1.55 g of trimethyloxonium tetrafluoroborate and 3.5 ml of Hünig base are added and the mixture is stirred overnight. After the same amount of reagent has been added again and the mixture has been stirred for a further 5 h, the reaction mixture is washed three times with water, the organic phase is dried over sodium sulphate, filtered and concentrated by rotary evaporation. The residue is chromatographed through a silica gel column with methylene chloride/methanol 9:1, the corresponding fractions are combined and concentrated by rotary evaporation.

Yield: 1.6 g (37% of theory)
$R_f$=0.78 (silica gel, methylene chloride/methanol 50:1)
$C_{22}H_{21}NO_6$ (MW=395.409)
Mass spectrum: m/z=396 (M+H)$^+$ The following compounds are prepared analogously to Example VI:

(1) 1,5-diacetyl-3-[(benzo[1,3]dioxol-5-yl)-methoxy-methylidene]-2-indolinone

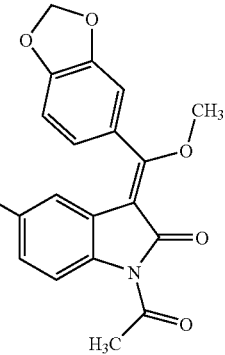

Prepared from 1,5-diacetyl-3-[(benzo[1,3]dioxol-5-yl)-hydroxy-methylidene]-2-indolinone (Ex. V.1)
Yield: 85% of theory
$R_f$=0.55 (silica gel, methylene chloride/methanol 30:1)
$C_{21}H_{17}NO_6$ (MW=379.366)
Mass spectrum: m/z=380 (M+H)$^+$ (2) 1,5-diacetyl-3-[(4-nitro-phenyl)-methoxy-methylidene]-2-indolinone

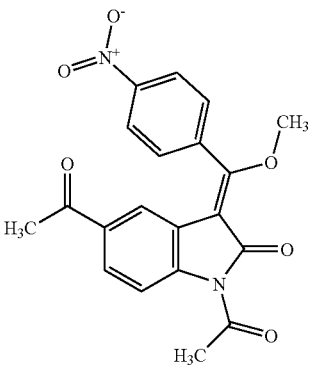

Prepared from 1,5-diacetyl-3-[(4-nitro-phenyl)-hydroxy-methylidene]-2-indolinone (Ex. V.2)
Yield: 82% of theory
$R_f$=0.55 (silica gel, methylene chloride/methanol 30:1)
$C_{20}H_{16}N_2O_6$ (MW=380.354)
Mass spectrum: m/z=381 (M+H)$^+$ (3) 1,5-diacetyl-3-[(3-nitro-phenyl)-methoxy-methylidene]-2-indolinone

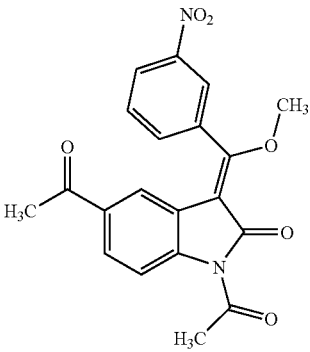

Prepared from 1,5-diacetyl-3-[(3-nitro-phenyl)-hydroxy-methylidene]-2-indolinone (Ex. V.3)
Yield: 43% of theory
$R_f$=0.44 (silica gel, methylene chloride/methanol 9:1)
$C_{20}H_{16}N_2O_6$ (MW=380.354)
Mass spectrum: m/z=381 (M+H)$^+$ (4) 1,5-diacetyl-3-[(4-methyloxycarbonyl-phenyl)-methoxy-methylidene]-2-indolinone

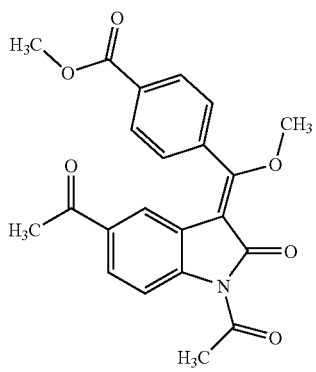

Prepared from 1,5-diacetyl-3-[(4-methyloxycarbonyl-phenyl)-hydroxy-methylidene]-2-indolinone (Ex. V.4)
Yield: 52% of theory
$R_f$=0.56 (silica gel, methylene chloride/methanol 30:1)
$C_{22}H_{19}NO_6$ (MW=393.393)
Mass spectrum: m/z=394 (M+H)$^+$ (5) 1,5-diacetyl-3-[(4-chloro-phenyl)-methoxy-methylidene]-2-indolinone

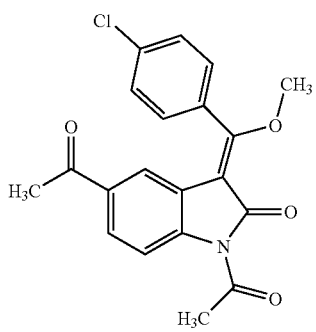

Prepared from 1,5-diacetyl-3-[(4-chloro-phenyl)-hydroxy-methylidene]-2-indolinone (Ex. V.5)
Yield: 65% of theory
$C_{20}H_{16}ClNO_4$ (MW=369.802)
Mass spectrum: m/z=370/372 (M+H)$^+$ (6) 1,5-diacetyl-3-[(3,4-dichloro-phenyl)-methoxy-methylidene]-2-indolinone

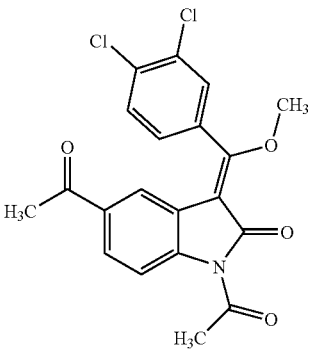

Prepared from 1,5-diacetyl-3-[(3,4-dichloro-phenyl)-hydroxy-methylidene]-2-indolinone (Ex. V.6)
Yield: 72% of theory
$C_{20}H_{15}Cl_2NO_4$ (MW=404.247)
Mass spectrum: m/z=404/406/408 (M+H)$^+$ (7) 1,5-diacetyl-3-[(4-cyano-phenyl)-methoxy-methylidene]-2-indolinone

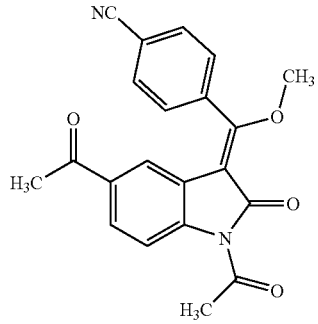

Prepared from 1,5-diacetyl-3-[(4-cyano-phenyl)-hydroxy-methylidene]-2-indolinone (Ex. V.7)
Yield: 53% of theory
$C_{21}H_{16}N_2O_4$ (MW=360.367)
Mass spectrum: m/z=361 (M+H)$^+$ (8) 1,5-diacetyl-3-[(4-trifluoromethyl-phenyl)-methoxy-methylidene]-2-indolinone

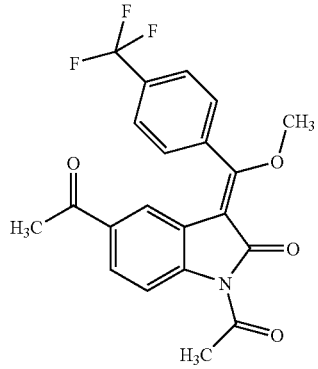

Prepared from 1,5-diacetyl-3-[(4-trifluoromethyl-phenyl)-hydroxy-methylidene]-2-indolinone (Ex. V.8)
Yield: 37% of theory
$C_{21}H_{16}F_3NO_4$ (MW=403.354)
Mass spectrum: m/z=404 (M+H)$^+$ (9) 1,5-diacetyl-3-[(2,3-dihydro-benzo-[1,4]dioxin-6-yl)-methoxy-methylidene]-2-indolinone

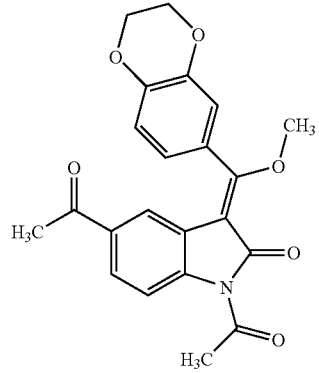

Prepared from 11,5-diacetyl-3-[(2,3-dihydro-benzo-[1,4]dioxin-6-yl)-hydroxy-methylidene]-2-indolinone (Ex. V.9)
Yield: 52% of theory
$R_f$=0.82 (silica gel, methylene chloride/methanol 9:1)
$C_{22}H_{19}NO_6$ (MW=393.393)
Mass spectrum: m/z=394 (M+H)$^+$

(10) 1,5-diacetyl-3-[(3-methoxy-phenyl)-methoxy-methylidene]-2-indolinone

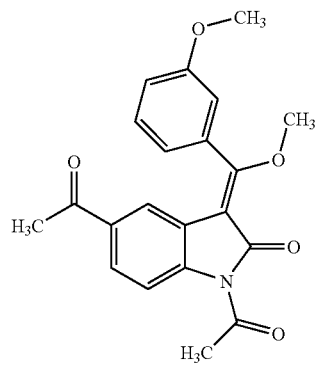

Prepared from 1,5-diacetyl-3-[(3-methoxy-phenyl)-hydroxy-methylidene]-2-indolinone (Ex. V.10)
Yield: 48% of theory
$R_f$=0.40 (silica gel, methylene chloride/methanol 9:1)

$C_{21}H_{19}NO_5$ (MW=365.383)
Mass spectrum: m/z=366 (M+H)$^+$

(11) 1,5-diacetyl-3-[(4-methoxy-phenyl)-methoxy-methylidene]-2-indolinone

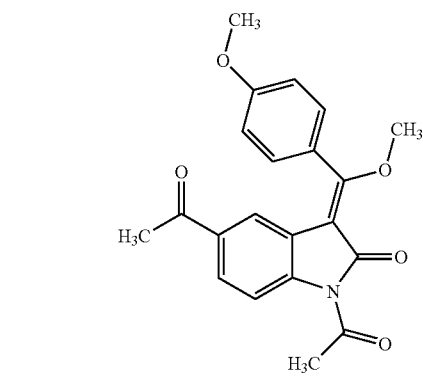

Prepared from 1,5-diacetyl-3-[(4-methoxy-phenyl)-hydroxy-methylidene]-2-indolinone (Ex. V.11)
Yield: 85% of theory
$R_f$=0.35 (silica gel, methylene chloride/methanol 30:1)
$C_{21}H_{19}NO_5$ (MW=365.383)
Mass spectrum: m/z=366 (M+H)$^+$

(12) 1-acetyl-5-propionyl-3-[(benzo[1,3]dioxol-5-yl)-methoxy-methylidene]-2-indolinone

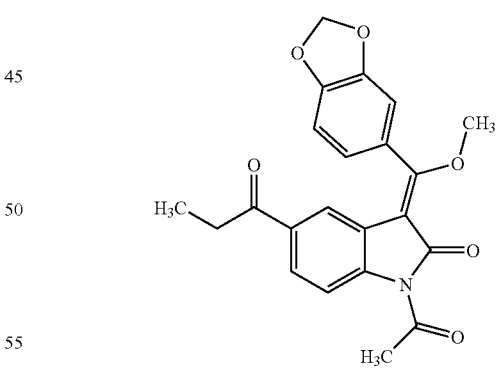

Prepared from 1-acetyl-5-propionyl-3-[(benzo[1,3]dioxol-5-yl)-hydroxy-methylidene]-2-indolinone (Ex. V.12)
Yield: 98% of theory
$R_f$=0.63 (silica gel, methylene chloride/methanol 30:1)
$C_{22}H_{19}NO_6$ (MW=393.393)
Mass spectrum: m/z=394 (M+H)$^+$

(13) 1,5-diacetyl-3-[(4-bromophenyl)-methoxy-methylidene]-2-indolinone

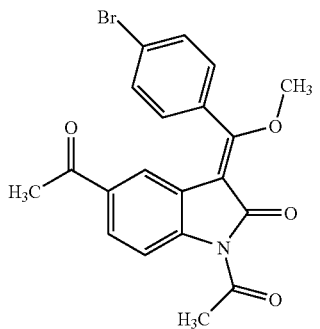

Prepared from 1,5-diacetyl-3-[(4-bromophenyl)-hydroxy-methylidene]-2-indolinone (Ex. V.13)
Yield: 48% of theory

(14) 1,5-diacetyl-3-[(3,5-dichloro-phenyl)-methoxy-methylidene]-2-indolinone

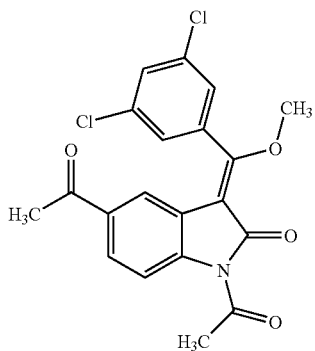

Prepared from 1,5-diacetyl-3-[(3,5-dichloro-phenyl)-hydroxy-methylidene]-2-indolinone (Ex. V.14)
Yield: 44% of theory
$R_f$=0.86 (silica gel, methylene chloride/methanol 30:1)
$C_{19}H_{13}Cl_2NO_4$ (MW=390.221)
Mass spectrum: m/z=388/390/392 (Cl2, M+H)$^+$

(15) 1,5-diacetyl-3-[(3,5-dimethoxy-phenyl)-methoxy-methylidene]-2-indolinone

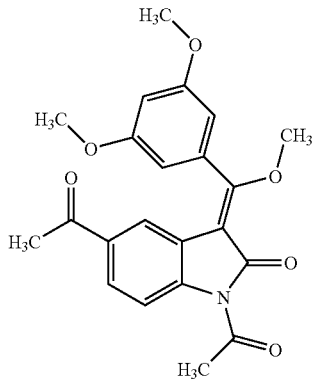

Prepared from 1,5-diacetyl-3-[(3,5-dimethoxy-phenyl)-hydroxy-methylidene]-2-indolinone (Ex. V.15)
Yield: 74% of theory
$R_f$=0.65 (silica gel, methylene chloride/methanol 30:1)
$C_{22}H_{21}NO_6$ (MW=395.409)
Mass spectrum: m/z=396 (M+H)$^+$

(16) 1,5-diacetyl-3-[(2-chloro-phenyl)-methoxy-methylidene]-2-indolinone

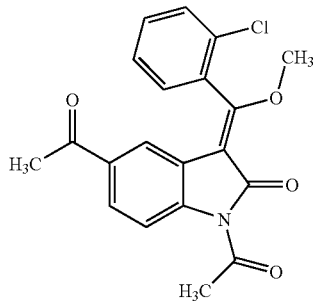

Prepared from 1,5-diacetyl-3-[(2-chloro-phenyl)-hydroxy-methylidene]-2-indolinone (Ex. V.16)
Yield: 54% of theory
$C_{20}H_{16}ClNO_4$ (MW=369.802)
Mass spectrum: m/z=370/372 (M+H)$^+$

(17) 1,5-diacetyl-3-[(2-methoxy-phenyl)-methoxy-methylidene]-2-indolinone

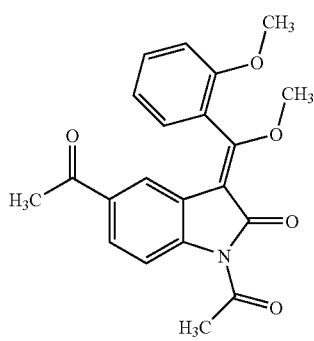

Prepared from 1,5-diacetyl-3-[(2-methoxy-phenyl)-hydroxy-methylidene]-2-indolinone (Ex. V.17)
Yield: 56% of theory
$C_{21}H_{19}NO_5$ (MW=365.383)
Mass spectrum: m/z=366 (M+H)$^+$

(18) 1,5-diacetyl-3-[(2,6-difluoro-phenyl)-methoxy-methylidene]-2-indolinone

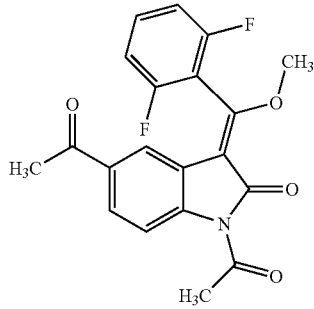

Prepared from 1,5-diacetyl-3-[(2,6-difluoro-phenyl)-hydroxy-methylidene]-2-indolinone (Ex. V.18)
Yield: 59% of theory
$C_{20}H_{15}F_2NO_4$ (MW=3371.337)
Mass spectrum: m/z=372 (M+H)$^+$

(19) 1,5-diacetyl-3-[(4-fluorophenyl)-methoxy-methylidene]-2-indolinone

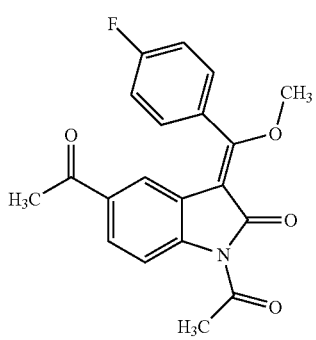

Prepared from 1,5-diacetyl-3-[(4-fluorophenyl)-hydroxy-methylidene]-2-indolinone (Ex. V.19)
Yield: 88% of theory
$C_{20}H_{16}FNO_4$ (MW=353.347)
Mass spectrum: m/z=354 (M+H)$^+$

(20) 1,5-diacetyl-3-[(3,4-difluoro-phenyl)-methoxy-methylidene]-2-indolinone

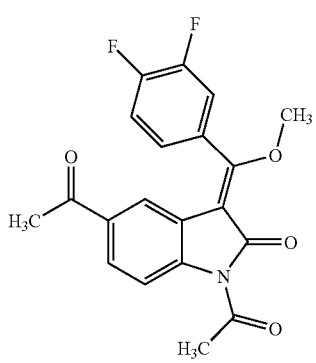

Prepared from 1,5-diacetyl-3-[(3,4-difluoro-phenyl)-hydroxy-methylidene]-2-indolinone (Ex. V.20)
Yield: 23% of theory
$C_{20}H_{15}F_2NO_4$ (MW=371.334)
Mass spectrum: m/z=372 (M+H)$^+$

(21) 1,5-diacetyl-3-[(2,2-difluoro-benzo[1,3]dioxol-5-yl)-methoxy-methylidene]-2-indolinone

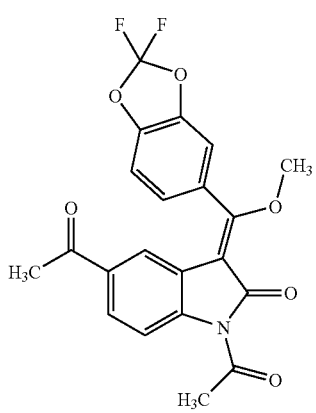

Prepared from 1,5-diacetyl-3-[(2,2-difluoro-benzo[1,3]dioxol-5-yl)-hydroxy-methylidene]-2-indolinone (Ex. V.21)
Yield: 6% of theory
$C_{21}H_{15}F_2NO_6$ (MW=415.346)
Mass spectrum: m/z=416 (M+H)$^+$

(22) 1,5-diacetyl-3-[(4-(2-methoxycarbonyl-ethyl)-phenyl)-methoxy-methylidene]-2-indolinone

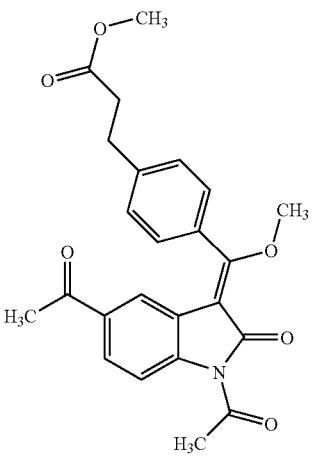

Prepared from 1,5-diacetyl-3-[(4-(2-methoxycarbonyl-ethyl)-phenyl)-hydroxy-methylidene]-2-indolinone (Ex. V.22)
Yield: 63% of theory
$C_{24}H_{23}NO_6$ (MW=421.447)
Mass spectrum: m/z=422 (M+H)$^+$

(23) 1,5-diacetyl-3-[furan-3-yl-methoxy-methylidene]-2-indolinone

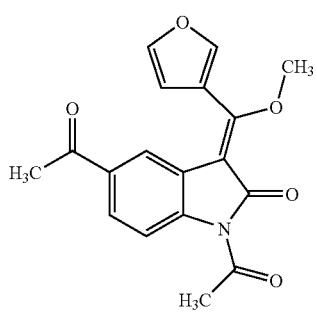

Prepared from 1,5-diacetyl-3-[furan-3-yl-hydroxy-methylidene]-2-indolinone (Ex. V.25)
Yield: 59% of theory
$C_{18}H_{15}NO_5$ (MW=325.324)
Mass spectrum: m/z=326 (M+H)$^+$

(24) 1,5-diacetyl-3-[(4-methoxycarbonylmethoxy-phenyl)-methoxy-methylidene]-2-indolinone

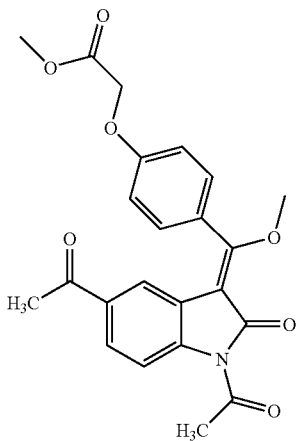

Prepared from 1,5-diacetyl-3-[(4-methoxycarbonyl-methoxy-phenyl)-hydroxy-methylidene]-2-indolinone (Ex. V.17)
Yield: 24% of theory
$C_{23}H_{21}NO_7$ (MW=423.415)
Mass spectrum: m/z=424 (M+H)$^+$

(25) 1,5-diacetyl-3-[(4-methylsulphonyl-phenyl)-methoxy-methylidene]-2-indolinone

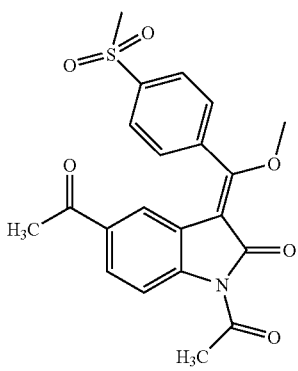

Prepared from 1,5-diacetyl-3-[(4-methylsulphonyl-phenyl)-hydroxy-methylidene]-2-indolinone (Ex. V.28)
Yield: 20% of theory
$C_{21}H_{19}NO_6S$ (MW=413.445)
Mass spectrum: m/z=414 (M+H)$^+$

(26) 1,5-diacetyl-3-(1-methoxy-octylidene)-2-indolinone

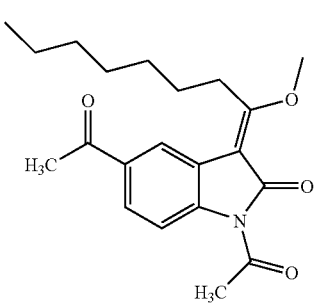

Prepared from 1,5-diacetyl-3-(1-hydroxyl-octylidene)-2-indolinone (Ex. X)
Yield: 82% of theory
$C_{21}H_{27}NO_4S$ (MW=357.443)
Mass spectrum: m/z=358 (M+H)$^+$

(27) 1,5-diacetyl-3-(1-methoxy-heptylidene)-2-indolinone

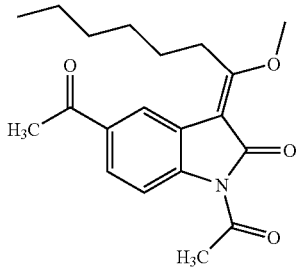

Prepared from 1,5-diacetyl-3-(1-hydroxy-heptylidene)-2-indolinone (Ex. V.31)

(28) 1,5-diacetyl-3-(1-methoxy-hexylidene)-2-indolinone

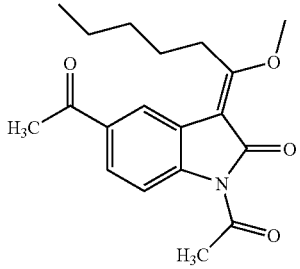

Prepared from 1,5-diacetyl-3-(1-hydroxy-hexylidene)-2-indolinone (Ex. V.32)

(29) 1,5-diacetyl-3-(1-methoxy-3-methyl-butylidene)-2-indolinone

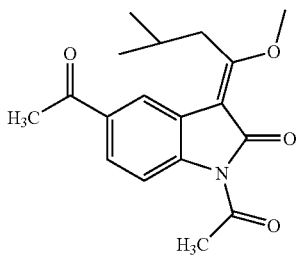

Prepared from 1,5-diacetyl-3-(11-hydroxy-3-methyl-butylidene)-2-indolinone (Ex. V.33)

EXAMPLE VII 1,5-diacetyl-3-[chloro-(pyrazin-2-yl)-methylidene]-2-indolinone

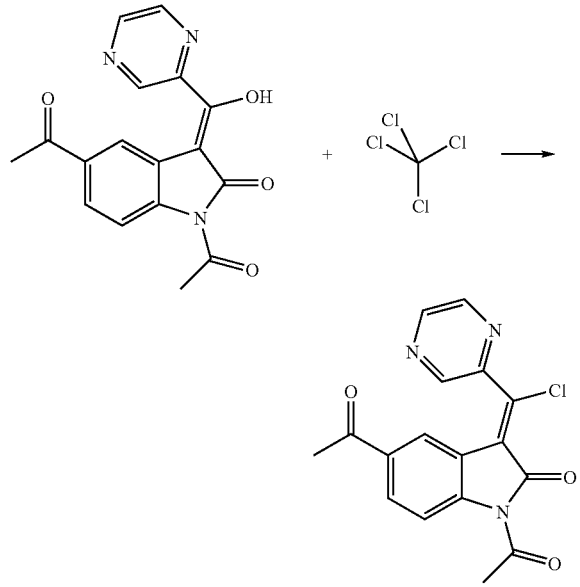

1.2 g (3.7 mmol) 1,5-diacetyl-3-[(pyrazin-2-yl)-hydroxy-methylidene]-2-indolinone (Ex. V.23) are dissolved in 50 ml dioxane and refluxed for 5 h with 2 ml carbon tetrachloride and 2 g triphenylphosphine. Then the mixture is left to cool and evaporated down. The residue is chromatographed through a silica gel column with methylene chloride/methanol 25:1, the corresponding fractions are combined and concentrated by rotary evaporation.

Yield: 400 mg (40% of theory)
$R_f$=0.70 (silica gel, methylene chloride/methanol 30:1)
$C_{17}H_{12}ClN_3O_3$ (MW=341.756)
Mass spectrum: m/z=342/344 (M+H)$^+$ (CL)

The following compound is prepared analogously to Example VII:

(1) 1,5-diacetyl-3-[chloro-(4-(2-dimethylamino-ethoxy)-phenyl)-methylidene]-2-indolinone

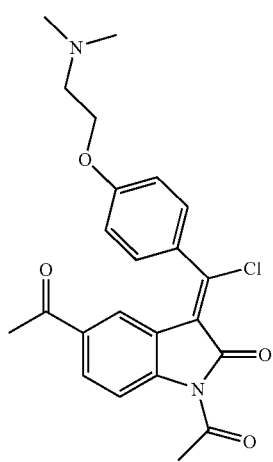

EXAMPLE VIII 1,5-diacetyl-3-[4-nitrophenyl-(1-methyl-piperidin-4-ylamino)-methylidene]-2-indolinone

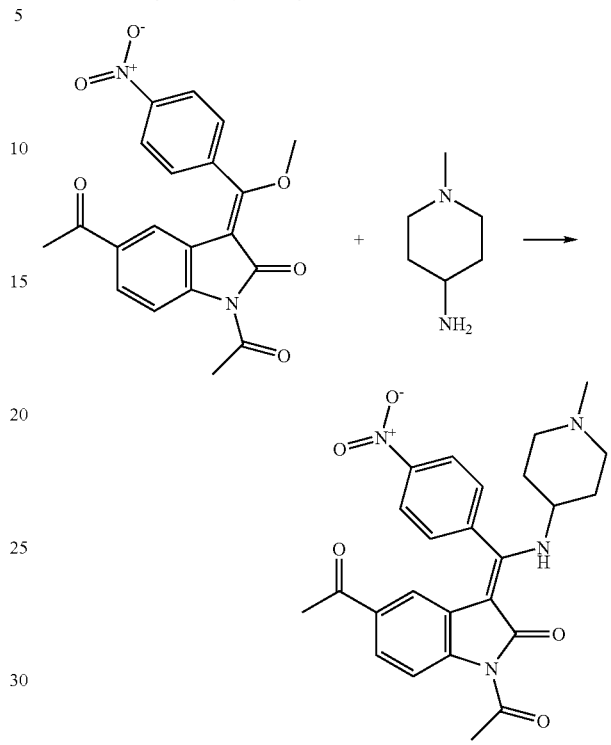

2.7 g (7 mmol) 1,5-diacetyl-3-[4-nitrophenyl-methoxy-methylidene]-2-indolinone (Ex. VI.2) are suspended in 20 ml of dimethylformamide and stirred with 0.9 g (7.7 mmol) 4-amino-N-methylpiperidine for 6 h at 80° C. Then the mixture is evaporated down and the acetyl-protected intermediate product is washed with a little water and suction filtered.

Yield: 2.4 g (72% of theory)
$C_{25}H_{26}N_4O_5$ (MW=462.51)
Mass spectrum: m/z=463 (M+H)$^+$ The following compounds are prepared analogously to Example VIII:

(1) 1,5-diacetyl-3-[3-nitrophenyl-(1-methyl-piperidin-4-ylamino)-methylidene]-2-indolinone

EXAMPLE IX 1,5-diacetyl-3-[4-aminophenyl-(1-methyl-piperidin-4-ylamino)-methylidene]-2-indolinone

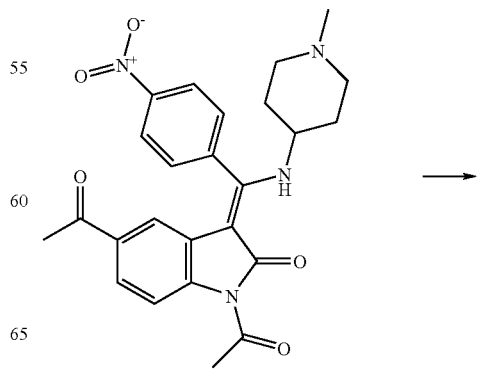

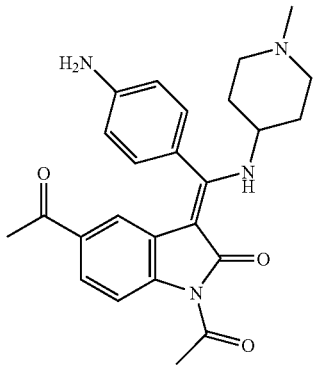

2.4 g (5 mmol) 1,5-diacetyl-3-[4-nitrophenyl-(1-methyl-piperidin-4-ylamino)-methylidene]-2-indolinone are dissolved in 40 ml of tetrahydrofuran (THF), 30 ml of methanol and 30 ml of ethyl acetate, combined with 250 mg Raney nickel and hydrogenated for 6 h at ambient temperature at a pressure of 50 psi. Then 20 ml of dimethylformamide are added in order to dissolve the precipitate formed and hydrogenation is continued for 2 h. Then the catalyst is filtered off and the solution is evaporated down.

Yield: 2.0 g (88% of theory)
$C_{25}H_{28}N_5O_3$ (MW=432.527)
Mass spectrum: m/z=433 (M+H)$^+$ The following compounds are prepared analogously to Example IX:

(1) 1,5-diacetyl-3-[3-aminophenyl-(1-methyl-piperidin-4-ylamino)-methylidene]-2-indolinone

EXAMPLE X 1,5-diacetyl-3-(1-hydroxy-octylidene)-2-indolinone

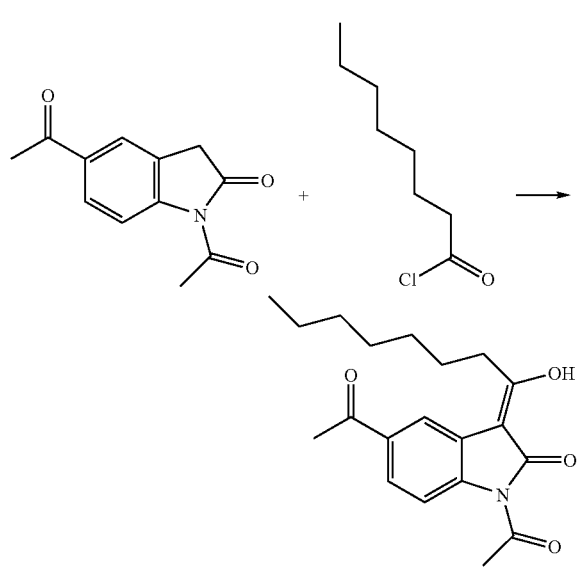

4.3 g (20 mmol) of 1,5-diacetyl-2-indolinone (Ex. II) are dissolved in 20 ml of dimethylformamide and 490 mg dimethylaminopyridine (DMAP) and 6 ml triethylamine are added and the mixture is cooled in the ice bath. 3.8 ml (22 mmol) octanoic acid chloride in 20 ml of dimethylformamide are added to this solution and the mixture is stirred for a further 10 min. Then the reaction mixture is added to 150 ml of methylene chloride and 150 ml of 1 N hydrochloric acid. The organic phase is separated off, dried over sodium sulphate and concentrated by rotary evaporation.

The residue is chromatographed through a silica gel column with methylene chloride/methanol 95:5.

Yield: 740 mg (11% of theory)
$C_{20}H_{25}NO_4$ (MW=343.417)
Mass spectrum: m/z=344 (M)$^+$

EXAMPLE XI trans-4-dimethylaminomethyl-cyclohexylamine a) methyl trans-4-tert-butoxycarbonylamino-cyclohexanecarboxylate 24.3 g (125 mmol) methyl trans-4-amino-cyclohexanecarboxylate hydrochloride (prepared analogously to T. P. Johnston, J. Med. Chem. 20 (2), 279-290 (1977)) are suspended in 250 ml methylene chloride, cooled in the ice bath and combined with 29.7 g BOC-anhydride. While cooling continues 34 ml of 4 N sodium hydroxide solution are slowly added dropwise and the mixture is stirred for a further hour. Then the organic phase is separated off, washed once with dilute citric acid solution and then evaporated down.

Yield: 32 g (99% of theory)

b) tert-butyl trans-4-hydroxymethyl-cyclohexyl-carbamate 1.56 g lithium borohydride are placed in 25 ml abs. tetrahydrofuran. A solution of 15.9 g (61 mmol) methyl trans-4-tert-butoxycarbonylamino-cyclohexanecarboxylate in 25 ml abs. tetrahydrofuran is added dropwise to this suspension. This suspension is refluxed for 50 min. After the reaction mixture has cooled it is carefully added dropwise to 25 ml of 0.6 N citric acid solution. Then 30 ml tert-butylmethylether are added, the solution is made alkaline with sodium hydroxide solution and the organic phase is separated off, washed and evaporated down.

Yield: 10.16 g (71% of theory)
$C_{12}H_{23}NO_3$ (MW=229.322)
Mass spectrum: m/z=252 (M+Na)$^+$ c) 4-tert-butoxycarbonylamino-cyclohexylmethyl trans-methanesulphonate 10.1 g (44 mmol) tert-butyl trans-4-hydroxymethyl-cyclohexyl-carbamate are dissolved in 140 ml methylene chloride and combined with 7.6 ml triethylamine. While stirring in the ice bath a solution of methanesulphonic acid chloride in 10 ml methylene chloride is slowly added dropwise. After it has been added, the ice bath is removed and the mixture is stirred for another 3 h at ambient temperature. The reaction mixture is washed with ice water and evaporated down.

Yield: 9.14 g (67% of theory)
$C_{13}H_{25}NO_5S$ (MW=307.412)
Mass spectrum: m/z=330 (M+Na)$^+$ d) tert-butyl(trans-4-dimethylaminomethyl-cyclohexyl)-carbamate 1 g (3.2 mmol) 4-tert-butoxycarbonylamino-cyclohexylmethyl trans-methanesulphonate are placed in 3 ml dioxane and combined with 0.3 g dimethylamine. The reaction mixture is stirred for 4 h at 100° C. in a bomb and then concentrated by rotary evaporation.

Yield: 0.728 g (87% of theory)
$C_{14}H_{28}N_2O_2$ (MW=256.384)
Mass spectrum: m/z=257 (M+H)$^+$ The following are prepared analogously:
tert-butyl(trans-4-piperidin-1-yl-methyl-cyclohexyl)-carbamate from 4-tert-butoxycarbonylamino-cyclohexylmethyl trans-methanesulphonate and piperidine
tert-butyl(trans-4-morpholin-1-yl-methyl-cyclohexyl)-carbamate from 4-tert-butoxycarbonylamino-cyclohexylmethyl trans-methanesulphonate and morpholine
tert-butyl(trans-4-(4-methylpiperazin-1-yl-methyl)-cyclohexyl)-carbamate from 4-tert-butoxycarbonylamino-cyclohexylmethyl trans-methanesulphonate and 4-methylpiperazine
tert-butyl(trans-4-(benzyl-methylamino-methyl-cyclohexyl)-carbamate from 4-tert-butoxycarbonylamino-cyclohexylmethyl trans-methanesulphonate and N-methylbenzylamine
tert-butyl(trans-4-(2-oxo-pyrrolidin-1-yl-methyl-cyclohexyl)-carbamate from 4-tert-butoxycarbonylamino-cyclohexylme trans-methanesulphonate and pyrrolidinone e) trans-4-dimethylaminomethyl-cyclohexylamine 8.4 g tert-butyl(trans-4-dimethylaminomethyl-cyclohexyl)-carbamate are dissolved in 100 ml methylene chloride and stirred overnight with 10 ml trifluoroacetic acid at ambient temperature. Then the mixture is concentrated by rotary evaporation and the residue is taken up in a little methylene chloride, made strongly alkaline with sodium hydroxide solution and the organic phase is separated off and evaporated down.

Yield: 3.1 g (61% of theory)
$C_9H_{20}N_2$ (MW=156.269)
Mass spectrum: m/z=157 (M+H)$^+$ The following are prepared analogously:
trans-4-piperidin-1-yl-methyl-cyclohexylamine from tert-butyl(trans-4-piperidin-1-yl-methyl-cyclohexyl)-carbamate
trans-4-morpholin-1-yl-methyl-cyclohexylamine from tert-butyl(trans-4-morpholin-1-yl-methyl-cyclohexyl)-carbamate
trans-4-(4-methylpiperazin-1-yl-methyl)-cyclohexylamine from tert-butyl(trans-4-(4-methylpiperazin-1-yl-methyl)-cyclohexyl)-carbamate
trans-4-(benzyl-methylamino-methyl)-cyclohexylamine from tert-butyl(trans-4-(benzyl-methylamino-methyl-cyclohexyl)-carbamate
trans-4-(2-oxo-pyrrolidin-1-yl-methyl-cyclohexylamine from tert-butyl(trans-4-(2-oxo-pyrrolidin-1-yl-methyl-cyclohexyl)-carbamate Preparation of the End Compounds:
Eluant:
A: methylene chloride/methanol 9:1
B: methylene chloride/methanol 4:1
C: methylene chloride/methanol/conc. ammonia 9:1:0.1
D: methylene chloride/methanol 30:1
E: methylene chloride/methanol/triethylamine 9:1:0.1

In the formulae in the Table the bond drawn free always represents the bond of the relevant group at the point of attachment in the molecule. The entry "—CH$_3$" in the Table thus denotes a methyl group and the entry

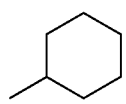

denotes a cyclohexyl group, and the entry

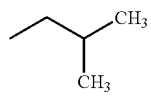

denotes an isobutyl group, i.e. —CH$_2$—CH(CH$_3$)$_2$.

As a rule the binding sites are also characterised by a dotted line.

EXAMPLE 1

5-Acetyl-3-[(benzo[1,3]dioxol-5-yl)-(1-methyl-piperidin-4-ylamino)-methylidene]-2-indolinone

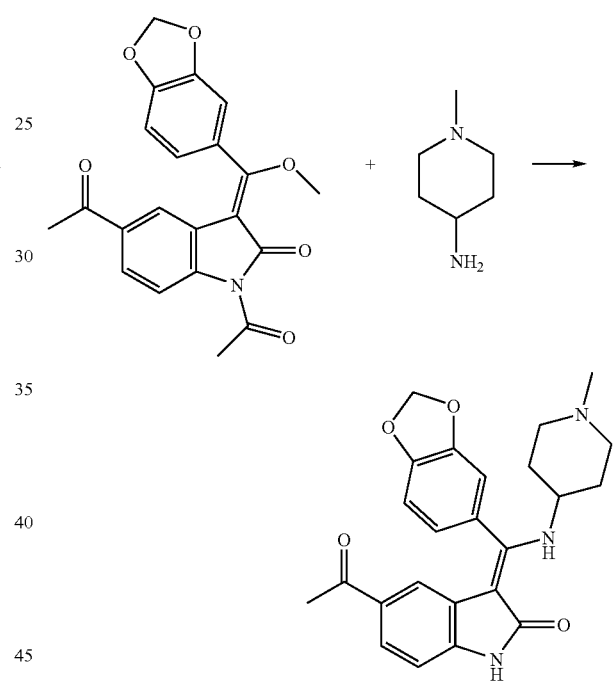

5 g (13.2 mmol) 1,5-diacetyl-3-[(benzo[1,3]dioxol-5-yl)-methoxy-methylidene]-2-indolinone (Ex. VI.1) are suspended in 50 ml of dimethylformamide and stirred overnight at ambient temperature with 1.5 g (13.2 mmol) 4-amino-N-methylpiperidine. The acetyl-protected intermediate product is combined with 2 ml of conc. ammonia without purification and stirred at ambient temperature for 30 min. Then the mixture is evaporated down and the residue is chromatographed through a silica gel column with the eluant methylene chloride/methanol 4:1.

Yield: 4.8 g (86% of theory)
$R_f$=0.33 (silica gel, methylene chloride/methanol/conc. ammonia 9:1:0.1)
$C_{24}H_{25}N_3O_4$ (MW=419.479)
Mass spectrum: m/z=420 (M+H)$^+$ The following compounds of formula I are prepared analogously to Example 1:

| Example | R¹ | R² | R³ | educt Yield [%] | Mass spectrum (ES) m/z | R_f value (silica gel) (eluant) |
|---|---|---|---|---|---|---|
| 1.001 | Me | Ph | 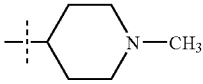 | III 66.6 | (M + H)⁺ = 376 | 0.26 (C) |
| 1.002 | Me | Ph | 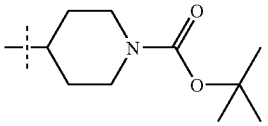 | III 78.5 | (M + H)⁺ = 462 | 0.53 (C) |
| 1.003 | Me | Ph | 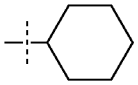 | III 77.7 | (M + H)⁺ = 361 | 0.51 (C) |
| 1.004 | Me | Ph | 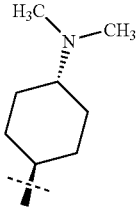 | III 74.3 | (M − H)⁻ = 402 | 0.37 (C) |
| 1.005 | Me | Ph | 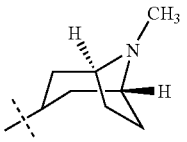 | III 64.8 | (M + H)⁺ = 402 | 0.42 (C) |
| 1.006 | Me | Ph | 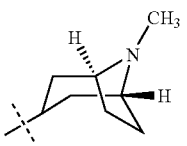 | III 74.7 | (M − H)⁻ = 400 | 0.39 (C) |
| 1.007 | Me | Ph | 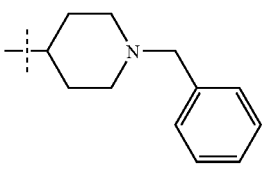 | III 97.4 | (M + H)⁺ = 452 | 0.58 (C) |
| 1.008 | Me | Ph | 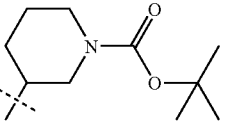 | III 73.7 | (M + H)⁺ = 462 | 0.43 (A) |
| 1.009 | n-Pr | Ph | 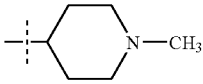 | IV 91.1 | (M + H)⁺ = 404 | 0.25 (C) |
| 1.010 | n-Pr | Ph | 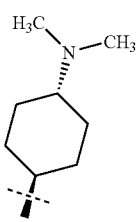 | IV 76.5 | (M + H)⁺ = 432 | 0.10 (C) |

-continued
| Example | R¹ | R² | R³ | educt Yield [%] | Mass spectrum (ES) m/z | R_f value (silica gel) (eluant) |
|---|---|---|---|---|---|---|
| 1.011 | n-Pr | Ph | 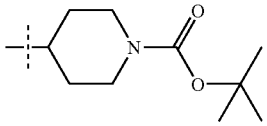 | IV 89.3 | (M + H)⁺ = 490 | 0.52 (A) |
| 1.012 | Me | 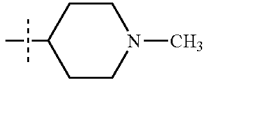 | 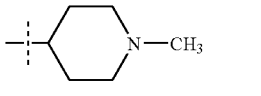 | V.2 80.3 | (M + H)⁺ = 421 | 0.48 (C) |
| 1.013 | Ph | Ph | 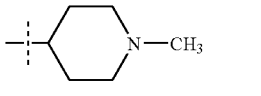 | III.2 86.8 | (M + H)⁺ = 438 | 0.19 (C) |
| 1.014 | Ph | Ph | 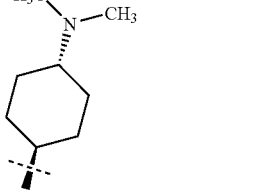 | III.2 79.5 | (M + H)⁺ = 466 | 0.42 (C) |
| 1.015 | Me | 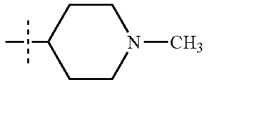 | 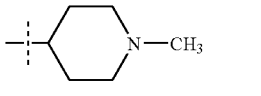 | VI 95 | (M + H)⁺ = 436 | 0.55 (C) |
| 1.016 | Me | 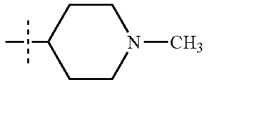 | 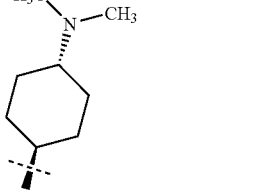 | VI 86.3 | (M + H)⁺ = 464 | 0.39 (C) |
| 1.017 | Me | Ph | 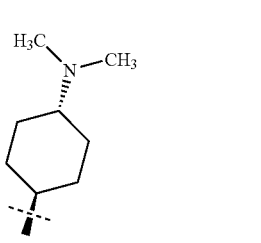 | III 75.4 | (M − H)⁻ = 416 | 0.12 (A) |
| 1.018 | Me | 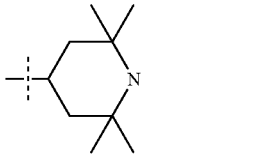 | 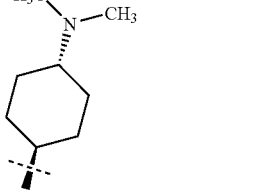 | VI.5 62.4 | (M + H)⁺ = 438/440 (Cl) | 0.14 (A) |
| 1.019 | Me | 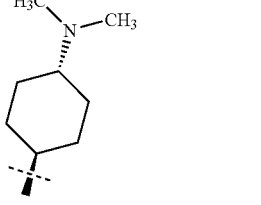 | 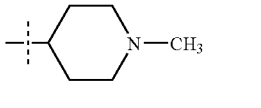 | VI.6 66.9 | (M + H)⁺ = 410/412 (Cl) | 0.35 (A) |

-continued
| Example | R¹ | R² | R³ | educt Yield [%] | Mass spectrum (ES) m/z | $R_f$ value (silica gel) (eluant) |
|---|---|---|---|---|---|---|
| 1.020 | Me | Ph | 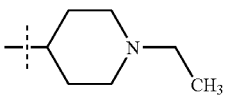 | III 12.8 | $(M + H)^+ = 390$ | 0.25 (A) |
| 1.021 | Me | Ph | 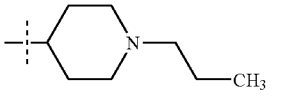 | III 10.7 | $(M + H)^+ = 404$ | 0.27 (A) |
| 1.022 | Me | Ph | 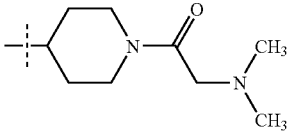 | III 10.3 | $(M + H)^+ = 447$ | 0.20 (A) |
| 1.023 | Me | Ph | 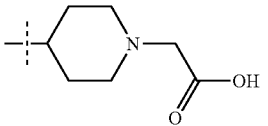 | III 22.9 | $(M + H)^+ = 420$ | 0.05 (A) |
| 1.024 | Me | Ph | 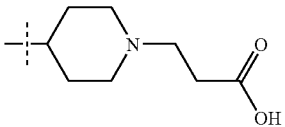 | III 16.6 | $(M + H)^+ = 434$ | 0.06 (A) |
| 1.025 | Me | Ph | 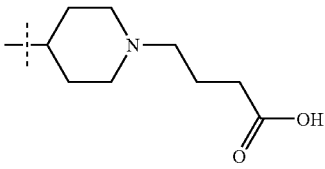 | III 13.4 | $(M + H)^+ = 448$ | 0.09 (A) |
| 1.026 | Me | 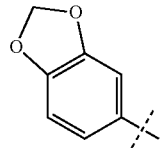 | 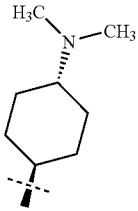 | VI 67.8 | $(M + H)^+ = 448$ | 0.12 (A) |
| 1.027 | Me | 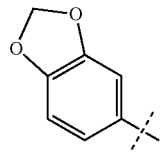 | 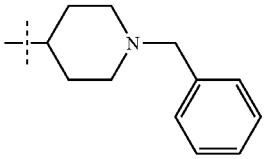 | VI.1 57.2 | $(M + H)^+ = 496$ | 0.32 (A) |
| 1.028 | Me | 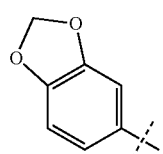 | 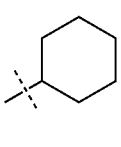 | VI.1 75.1 | $(M + H)^+ = 405$ | 0.26 (D) |
| 1.029 | Me | 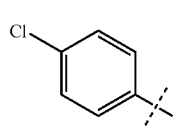 | 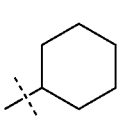 | VI.5 83.8 | $(M + H)^+ = $ 395/397 (Cl) | 0.04 (D) |

-continued
| Example | R¹ | R² | R³ | educt Yield [%] | Mass spectrum (ES) m/z | R$_f$ value (silica gel) (eluant) |
|---|---|---|---|---|---|---|
| 1.030 | Me | 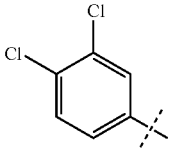 | 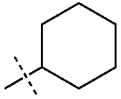 | VI.6 58.8 | (M + H)⁺ = 429/431/433 (Cl2) | 0.36 (A) |
| 1.031 | Me | 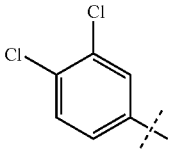 | 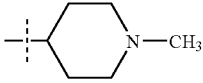 | VI.6 52.3 | (M + H)⁺ = 444/446/448 (Cl2) | 0.21 (A) |
| 1.032 | Me | 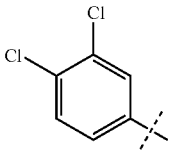 | 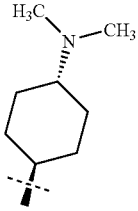 | VI.6 66.3 | (M + H)⁺ = 472/474/476 (Cl2) | 0.26 (A) |
| 1.033 | Me | 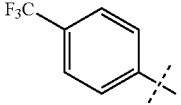 | 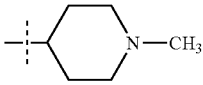 | VI.8 38.2 | (M + H)⁺ = 444 | 0.37 (C) |
| 1.034 | Me | 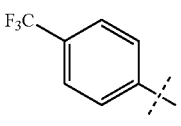 | 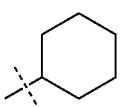 | VI.8 28.2 | (M + H)⁺ = 429 | 0.38 (C) |
| 1.035 | Me | 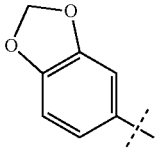 | 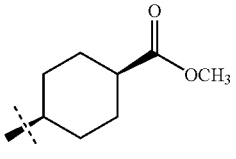 | VI.1 65.6 | (M + H)⁺ = 463 | 0.44 (A) |
| 1.036 | Me | 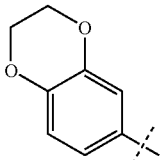 | 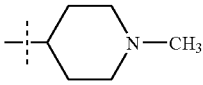 | VI.9 49.9 | (M + H)⁺ = 434 | 0.19 (A) |
| 1.037 | Me | 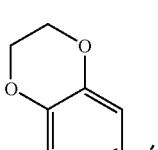 | 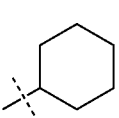 | VI.9 51.7 | (M + H)⁺ = 419 | 0.38 (A) |
| 1.038 | Me | Ph | 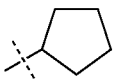 | III 95.9 | (M + H)⁺ = 347 | 0.26 (A) |

-continued
| Example | R¹ | R² | R³ | educt Yield [%] | Mass spectrum (ES) m/z | R_f value (silica gel) (eluant) |
|---|---|---|---|---|---|---|
| 1.039 | Me | 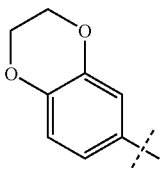 | 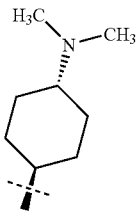 | VI.9 46.9 | (M + H)⁺ = 462 | 0.21 (CH₂Cl₂/ MeOH 6:1) |
| 1.040 | Me | 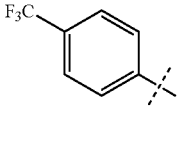 | 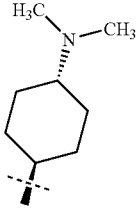 | VI.8 85.5 | (M − H)⁻ = 470 | 0.39 (C) |
| 1.041 | Me | 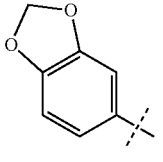 | 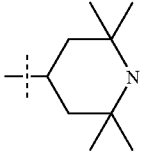 | VI.1 64.8 | (M + H)⁺ = 434 | 0.17 (A) |
| 1.042 | Me | 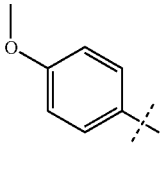 | 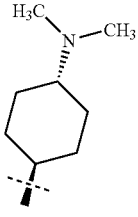 | VI.11 42.2 | (M + H)⁺ = 434 | 0.09 (A) |
| 1.043 | Me | 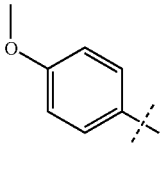 | 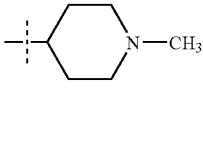 | VI.11 41.2 | (M + H)⁺ = 406 | 0.23 (A) |
| 1.044 | Me | 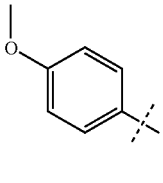 | 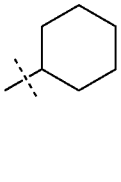 | VI.11 58.5 | (M + H)⁺ = 391 | 0.41 (A) |
| 1.045 | Me | 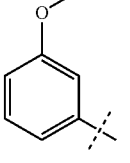 | 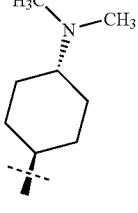 | VI.10 63.2 | (M + H)⁺ = 434 | 0.18 (A) |

-continued

| Example | R¹ | R² | R³ | educt Yield [%] | Mass spectrum (ES) m/z | R_f value (silica gel) (eluant) |
|---|---|---|---|---|---|---|
| 1.046 | Me | 3-methoxyphenyl | 1-methylpiperidin-4-yl | VI.10 56.8 | (M + H)⁺ = 406 | 0.26 (A) |
| 1.047 | Me | 3-methoxyphenyl | cyclohexyl | VI.10 70.2 | (M + H)⁺ = 391 | 0.37 (A) |
| 1.048 | Me | 3,5-dichlorophenyl | 4-(N,N-dimethylamino)cyclohexyl | VI.14 89.8 | (M + H)⁺ = 472/474/476 (Cl2) | 0.14 (A) |
| 1.049 | Me | 3,5-dichlorophenyl | 1-methylpiperidin-4-yl | VI.14 36.4 | (M + H)⁺ = 444/446/448 (Cl2) | 0.16 (A) |
| 1.050 | Me | 3,5-dichlorophenyl | cyclohexyl | VI.14 3209 | (M − H)⁻ = 427/429/431 (Cl2) | 0.37 (C) |
| 1.051 | Me | 3,5-dimethoxyphenyl | 4-(N,N-dimethylamino)cyclohexyl | VI.15 61.8 | (M + H)⁺ = 464 | 0.22 (A) |
| 1.052 | Me | 3,5-dimethoxyphenyl | 1-methylpiperidin-4-yl | VI.15 68.1 | (M + H)⁺ = 436 | 0.22 (A) |
| 1.053 | Me | 3,5-dimethoxyphenyl | cyclohexyl | VI.15 11.3 | (M + H)⁺ = 421 | 0.12 (A) |

-continued
| Example | R¹ | R² | R³ | educt Yield [%] | Mass spectrum (ES) m/z | $R_f$ value (silica gel) (eluant) |
|---|---|---|---|---|---|---|
| 1.054 | Me | 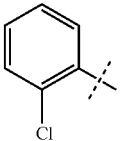 |  | VI.16 45.4 | $(M + H)^+ =$ 410/412 (Cl) | 0.12 (A) |
| 1.055 | Me | 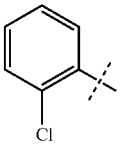 | 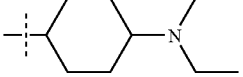 | VI.16 24.4 | $(M + H)^+ =$ 466/468 (Cl) | 0.05 (A) |
| 1.056 | Me | 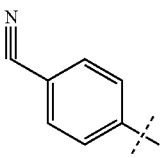 | 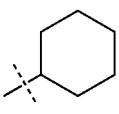 | VI.7 95.1 | $(M + H)^+ = 386$ | 0.32 (A) |
| 1.057 | Me | 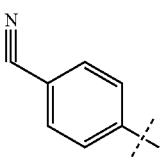 | 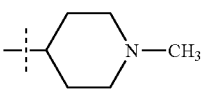 | VI.7 90 | $(M + H)^+ = 401$ | 0.35 (A) |
| 1.058 | Me | 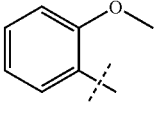 | 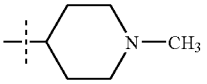 | VI.17 30.8 | $(M + H)^+ = 406$ | 0.52 (A) |
| 1.059 | Me | Ph | 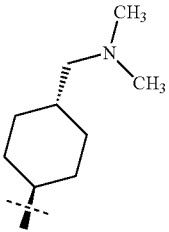 | III 57.8 | $(M + H)^+ = 418$ | 0.26 (A) |
| 1.060 | Me | 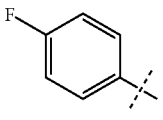 | 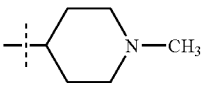 | VI.19 83.7 | not determined | 0.38 (A) |
| 1.061 | Me | 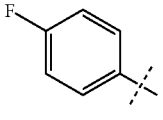 | 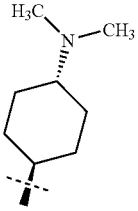 | VI.19 72.6 | $(M + H)^+ = 422$ | 0.20 (A) |
| 1.062 | Me | 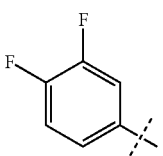 | 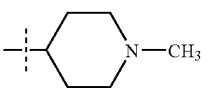 | VI.20 66.7 | $(M + H)^+ = 412$ | 0.38 (C) |

-continued
| Example | R¹ | R² | R³ | educt Yield [%] | Mass spectrum (ES) m/z | R_f value (silica gel) (eluant) |
|---|---|---|---|---|---|---|
| 1.063 | Me | 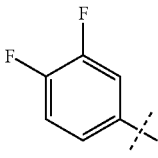 | 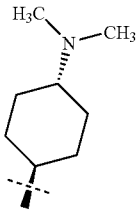 | VI.20 30.7 | (M + H)⁺ = 440 | 0.37 (C) |
| 1.064 | Me | 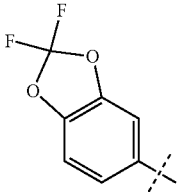 | 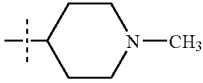 | VI.21 18.3 | (M + H)⁺ = 456 | 0.31 (A) |
| 1.065 | Me | 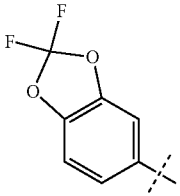 | 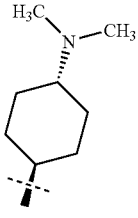 | VI.21 15.8 | (M + H)⁺ = 484 | 0.39 (A) |
| 1.066 | Me | Ph | 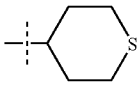 | III 58.6 | (M + H)⁺ = 379 | 0.52 (A) |
| 1.067 | Me | 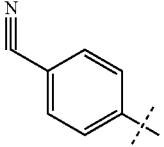 | 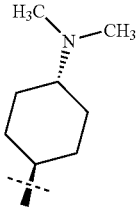 | VI.7 83 | (M + H)⁺ = 429 | 0.31 (C) |
| 1.068 | Me | 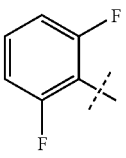 | 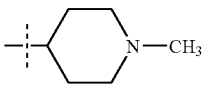 | VI.18 14.4 | (M + H)⁺ = 412 | 0.59 (A) |
| 1.069 | Me | 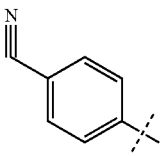 |  | VI.7 89.2 | (M + H)⁺ = 372 | 0.36 (A) |
| 1.070 | Me | 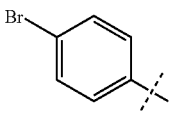 | 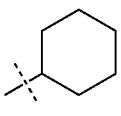 | VI.13 89.1 | (M − H)⁻ = 437/439 (Br) | 0.41 (A) |

-continued
| Example | R¹ | R² | R³ | educt Yield [%] | Mass spectrum (ES) m/z | R_f value (silica gel) (eluant) |
|---|---|---|---|---|---|---|
| 1.071 | Me | 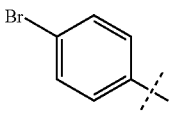 | 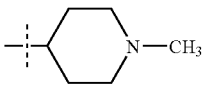 | VI.13 77.9 | (M + H)⁺ = 454/456 (Br) | 0.18 (A) |
| 1.072 | Me | 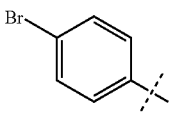 | 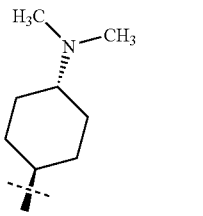 | VI.13 85.8 | (M + H)⁺ = 482/484 (Br) | 0.12 (A) |
| 1.073 | Me | Ph |  | III 63.8 | (M + H)⁺ = 411 | 0.32 (A) |
| 1.074 | Me | 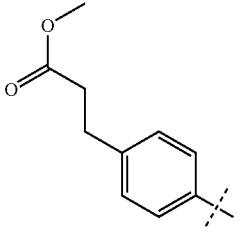 | 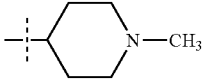 | VI.22 18.3 | (M + H)⁺ = 462 | 0.26 (A) |
| 1.075 | Me | 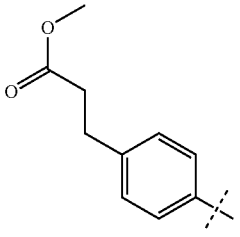 | 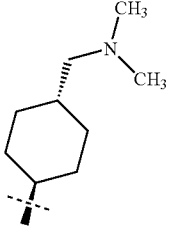 | VI.22 16.7 | (M + H)⁺ = 504 | 0.42 (A) |
| 1.076 | Me | 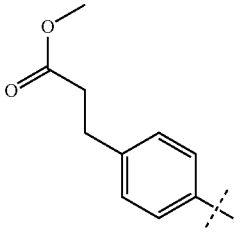 | 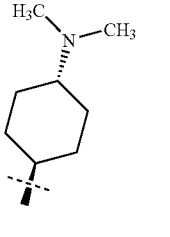 | VI.22 74.6 | (M + H)⁺ = 490 | 0.43 (C) |
| 1.077 | Me | 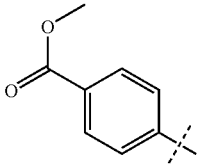 | 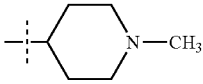 | VI.4 98.9 | (M + H)⁺ = 434 | 0.03 (C) |

-continued

| Example | R$^1$ | R$^2$ | R$^3$ | educt Yield [%] | Mass spectrum (ES) m/z | R$_f$ value (silica gel) (eluant) |
|---|---|---|---|---|---|---|
| 1.078 | Me | methyl benzoate | N,N-dimethyl cyclohexyl | VI.4 75.3 | (M + H)$^+$ = 462 | 0.17 (C) |
| 1.079 | Me | nitrophenyl | N-methyl piperidinyl | VI.3 72.9 | (M + H)$^+$ = 421 | 0.19 (A) |
| 1.080 | Me | Ph | methyl cyclohexanecarboxylate | III 70.5 | (M + H)$^+$ = 419 | 0.68 (A) |
| 1.081 | Et | benzodioxole | N,N-dimethyl cyclohexyl | VI.1 48.1 | (M + H)$^+$ = 462 | 0.16 (A) |
| 1.082 | Et | benzodioxole | N-methyl piperidinyl | VI.1 54.7 | (M + H)$^+$ = 434 | 0.24 (A) |
| 1.083 | Et | benzodioxole | cyclohexyl | VI.1 31.7 | (M + H)$^+$ = 419 | 0.36 (A) |
| 1.084 | Me | benzodioxole | cyclohexyl-O-CH$_2$CH$_2$-N(CH$_3$)$_2$ | VI.1 41.2 | (M + H)$^+$ = 492 | 0.09 (A) |
| 1.085 | Me | benzodioxole | N-Boc piperidinyl | VI.1 92.0 | (M + H)$^+$ = 506 | 0.037 (A) |

-continued
| Example | R¹ | R² | R³ | educt Yield [%] | Mass spectrum (ES) m/z | R_f value (silica gel) (eluant) |
|---|---|---|---|---|---|---|
| 1.086 | Me | 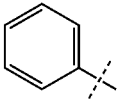 | 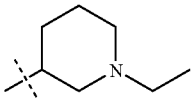 | III 78.0 | (M + H)⁺ = 390 | 0.38 (C) |
| 1.087 | Me | 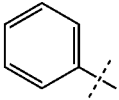 | 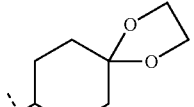 | III 79.0 | (M + H)⁺ = 419 | 0.43 (A) |
| 1.088 | Me | 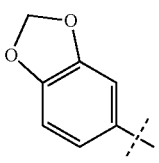 | 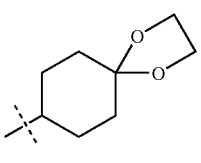 | VI.1 49.0 | (M + H)⁺ = 463 | 0.18 (D) |
| 1.089 | Me | 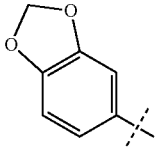 | 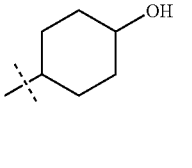 | VI.1 33.0 | (M + H)⁺ = 421 | 0.69 (A) |
| 1.090 | Me | 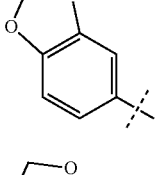 | 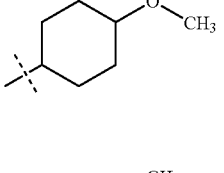 | VI.1 28.0 | (M + H)⁺ = 435 | 0.62 (A) |
| 1.091 | Me | 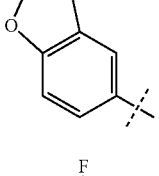 | 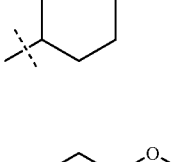 | VI.1 56.0 | (M + H)⁺ = 419 | 0.14 (D) |
| 1.092 | Me | 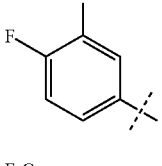 | 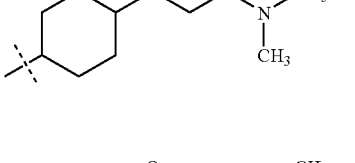 | VI.20 29.0 | (M + H)⁺ = 484 | 0.38 (A) |
| 1.903 | Me | 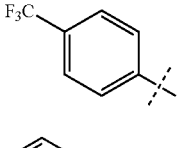 | 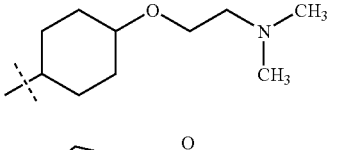 | VI.8 34.0 | (M + H)⁺ = 516 | 0.41 (A) |
| 1.094 | Me | 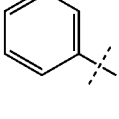 | 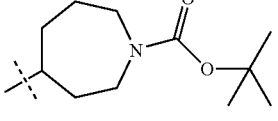 | III 80.0 | (M + H)⁺ = 520 | 0.4 (A) |
| 1.095 | Me | 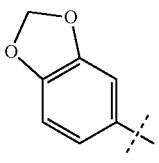 | 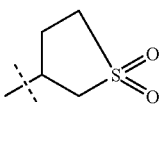 | VI.1 45.0 | (M + H)⁺ = 441 | 0.53 (A) |

-continued

| Example | R¹ | R² | R³ | educt Yield [%] | Mass spectrum (ES) m/z | R_f value (silica gel) (eluant) |
|---|---|---|---|---|---|---|
| 1.096 | Me | methyl 2-(4-phenoxy)acetate | 1-methylpiperidin-4-yl | VI.24 40.0 | (M + H)⁺ = 464 | 0.07 (C) |
| 1.097 | Me | methyl 2-(4-phenoxy)acetate | cyclohexyl | VI.24 37.0 | (M + H)⁺ = 449 | 0.48 (A) |
| 1.098 | Me | 4-(methylsulfonyl)phenyl | 1-methylpiperidin-4-yl | VI.25 35.0 | (M + H)⁺ = 454 | 0.23 (A) |
| 1.099 | Me | 4-(methylsulfonyl)phenyl | 4-(diethylamino)cyclohexyl | VI.25 26.0 | (M + H)⁺ = 510 | 0.07 (B) |
| 1.100 | Me | 4-(trifluoromethyl)phenyl | 4-(diethylamino)cyclohexyl | VI.8 61.0 | (M + H)⁺ = 500 | 0.12 (A) |
| 1.101 | Me | 4-(trifluoromethyl)phenyl | 1,4-dioxaspiro[4.5]decan-8-yl | VI.8 73.0 | (M + H)⁺ = 487 | 0.36 (A) |
| 1.102 | Me | 4-(trifluoromethyl)phenyl | 4-(Boc-amino)cyclohexyl | VI.8 63.0 | (M + H)⁺ = 544 | 0.44 (A) |
| 1.103 | Me | 4-(trifluoromethyl)phenyl | 4-carboxycyclohexyl | VI.8 65.0 | (M + H)⁺ = 473 | 0.33 (A) |

-continued

| Example | R¹ | R² | R³ | educt Yield [%] | Mass spectrum (ES) m/z | R$_f$ value (silica gel) (eluant) |
|---|---|---|---|---|---|---|
| 1.104 | Me | phenyl | 4-hydroxy-4-methylcyclohexyl | III 83.0 | (M + H)⁺ = 391 | 0.63 (A) |
| 1.105 | Me | 1,3-benzodioxol-5-yl | (4-(morpholinomethyl)cyclohexyl) | VI.1 36.0 | (M + H)⁺ = 504 | 0.41 (A) |
| 1.106 | Me | 1,3-benzodioxol-5-yl | (4-(piperidinomethyl)cyclohexyl) | VI.1 19.0 | (M + H)⁺ = 502 | 0.35 (A) |
| 1.107 | Me | 1,3-benzodioxol-5-yl | (4-((4-methylpiperazin-1-yl)methyl)cyclohexyl) | VI.1 32.0 | (M + H)⁺ = 517 | 0.16 (A) |
| 1.108 | Me | 1,3-benzodioxol-5-yl | (4-((N-methyl-N-benzylamino)methyl)cyclohexyl) | VI.1 38.0 | (M + H)⁺ = 538 | 0.46 (A) |
| 1.109 | Me | 1,3-benzodioxol-5-yl | (4-((2-oxopyrrolidin-1-yl)methyl)cyclohexyl) | VI.1 18.0 | (M + H)⁺ = 502 | 0.50 (A) |
| 1.110 | Me | phenyl | (4-(morpholinomethyl)cyclohexyl) | III 38.0 | (M + H)⁺ = 460 | 0.46 (A) |
| 1.111 | Me | phenyl | (4-((2-oxopyrrolidin-1-yl)methyl)cyclohexyl) | III 31.0 | (M + H)⁺ = 458 | 0.50 (A) |
| 1.112 | Me | phenyl | (4-(piperidinomethyl)cyclohexyl) | III 43.0 | (M + H)⁺ = 458 | 0.26 (A) |
| 1.113 | Me | phenyl | (4-((4-methylpiperazin-1-yl)methyl)cyclohexyl) | III 40.0 | (M + H)⁺ = 473 | 0.10 (A) |

-continued

| Example | R¹ | R² | R³ | educt Yield [%] | Mass spectrum (ES) m/z | R_f value (silica gel) (eluant) |
|---|---|---|---|---|---|---|
| 1.114 | Me | phenyl | cyclohexyl-CH₂-N(CH₃)(CH₂Ph) | III 34.0 | $(M+H)^+ = 494$ | 0.51 (A) |
| 1.115 | Me | 4-F₃C-phenyl | cyclohexyl-CH₂-N(CH₃)₂ | VI.8 22.0 | $(M+H)^+ = 486$ | 0.17 (A) |
| 1.116 | Me | 3,4-difluorophenyl | cyclohexyl-CH₂-N(CH₃)₂ | VI.20 60.0 | $(M+H)^+ = 454$ | 0.16 (A) |
| 1.117 | Me | 3,4-difluorophenyl | cyclohexyl-CH₂-morpholine | VI.20 37.0 | $(M+H)^+ = 496$ | 0.30 (A) |
| 1.118 | Me | 4-F₃C-phenyl | cyclohexyl-CH₂-morpholine | VI.8 83.0 | $(M+H)^+ = 528$ | 0.30 (C) |
| 1.119 | Me | heptyl | N-methylpiperidin-4-yl | VI.26 64.7 | $(M+H)^+ = 398$ | 0.31 (A) |
| 1.120 | Me | heptyl | cyclohexyl-N(CH₃)₂ | VI.26 65.5 | $(M+H)^+ = 426$ | 0.18 (A) |
| 1.121 | Me | hexyl | N-methylpiperidin-4-yl | VI.27 89.3 | $(M+H)^+ = 384$ | 0.35 (A) |

-continued

| Example | R¹ | R² | R³ | educt Yield [%] | Mass spectrum (ES) m/z | R_f value (silica gel) (eluant) |
|---|---|---|---|---|---|---|
| 1.122 | Me | (n-hexyl, dashed bond) | H₃C-N(CH₃)-cyclohexyl | VI.27 71.6 | (M + H)⁺ = 412 | 0.09 (A) |
| 1.123 | Me | (n-pentyl, dashed bond) | 1-methylpiperidin-4-yl | VI.28 25.0 | (M + H)⁺ = 370 | 0.38 (A) |
| 1.124 | Me | (n-pentyl, dashed bond) | H₃C-N(CH₃)-cyclohexyl | VI.28 41 | (M + H)⁺ = 398 | 0.39 (C) |
| 1.125 | Me | (isobutyl, dashed bond) | 1-methylpiperidin-4-yl | VI.29 33.0 | (M + H)⁺ = 356 | 0.36 (C) |
| 1.126 | Me | (isobutyl, dashed bond) | H₃C-N(CH₃)-cyclohexyl | VI.29 32.0 | (M + H)⁺ = 384 | 0.31 (C) |
| 1.127 | Et | Et | 1-methylpiperidin-4-yl | III.7 75.0 | (M + H)⁺ = 342 | 0.21 (A) |
| 1.128 | Et | Et | H₃C-N(CH₃)-cyclohexyl | III.7 71.0 | (M + H)⁺ = 370 | 0.08 (A) |
| 1.129 | n-C₅H₁₀ | Et | H₃C-N(CH₃)-cyclohexyl | III.8 46.0 | (M + H)⁺ = 412 | 0.12 (A) |
| 1.130 | n-C₅H₁₀ | Et | 1-methylpiperidin-4-yl | III.8 56.0 | (M + H)⁺ = 384 | 0.25 (A) |

-continued

| Example | R¹ | R² | R³ | educt Yield [%] | Mass spectrum (ES) m/z | $R_f$ value (silica gel) (eluant) |
|---|---|---|---|---|---|---|
| 1.131 | Me | 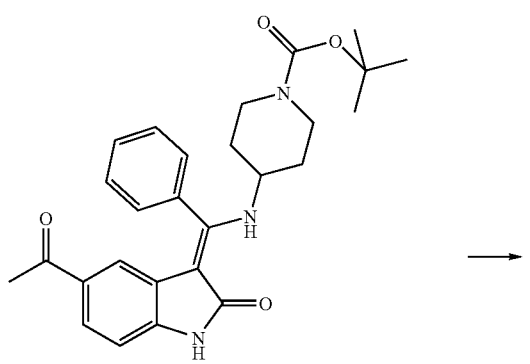 | | VI.28 95.0 | $(M+H)^+ = 412$ | 0.40 (C) |
| 1.132 | Me | | | VI.29 79.0 | $(M+H)^+ = 398$ | 0.32 (C) |

EXAMPLE 2

5-acetyl-3-[phenyl-(piperidin-4-ylamino)-methylidene]-2-indolinone-triflate

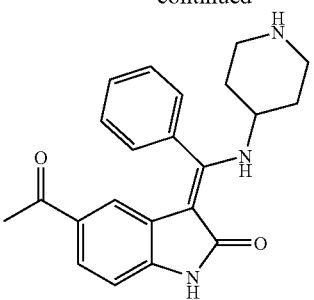

-continued

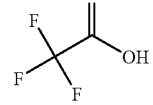

140 mg (0.3 mmol) 5-acetyl-3-[phenyl-(t-butyloxy-carbonyl-piperidin-4-ylamino)-methylidene]-2-indolinone (Example 1.002) are added batchwise to a solution of 1 ml trifluoroacetic acid in 10 ml methylene chloride and stirred overnight at ambient temperature. Then the mixture is evaporated down.

Yield: 130 mg (90% of theory)

$R_f$=0.28 (silica gel, methylene chloride/methanol/conc. ammonia 9:1:0.1)

$C_{22}H_{23}N_3O_2$ (MW=361.45)

Mass spectrum: m/z=362 (M+H)⁺

The following compounds of formula I are prepared analogously to Example 2, in each case as the triflate:

| Example | R¹ | R² | R³ | educt Yield [%] | Mass spectrum (ES) m/z | $R_f$ value (silica gel) (eluant) |
|---|---|---|---|---|---|---|
| 2.001 | Me | Ph | | 1.008 98.8 | $(M+H)^+ = 362$ | 0.17 (A) |

-continued

| Example | R¹ | R² | R³ | educt Yield [%] | Mass spectrum (ES) m/z | $R_f$ value (silica gel) (eluant) |
|---|---|---|---|---|---|---|
| 2.002 | n-Pr | Ph | (piperidine) | 1.011 87.6 | $(M + H)^+$ = 390 | 0.07 (C) |
| 2.003 | Me | (benzodioxole) | (piperidine) | 1.085 83.0 | $(M + H)^+$ = 405 | 0.07 (A) |
| 2.004 | Me | (benzodioxole) | (azepane) | 1.094 58.0 | $(M + H)^+$ = 420 | 0.12 (B) |
| 2.005 | Me | (benzodioxole) | (piperidinyl-glycinamide) | 19.00 46.0 | $(M + H)^+$ = 463 | 0.35 (B) |
| 2.006 | Me | $F_3C$-phenyl | (aminocyclohexyl) | 1.102 90.0 | $(M + H)^+$ = 444 | 0.05 (A) |

EXAMPLE 3

5-acetyl-3-[(trans-4-dimethylamino-cyclohexy-lamino)-(4-(carboxymethyl-carbamoyl)-phenyl)-methylidene]-2-indolinone

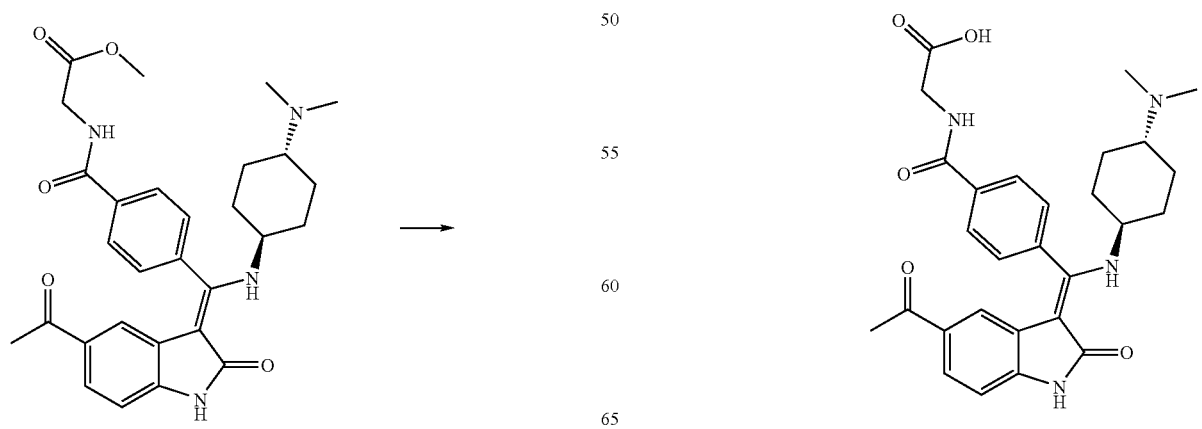

20 mg (0.039 mmol) 5-acetyl-3-[(trans-4-dimethylamino-cyclohexylamino)-(4-(methoxycarbonyl-methyl-carbamoyl-phenyl-methylidene]-2-indolinone (Example 4.005) are suspended in 0.1 ml 1 N sodium hydroxide solution and 1 ml of methanol and stirred for 3 h at 60° C. Then the mixture is allowed to cool and 0.1 ml of 1 N hydrochloric acid are added and the precipitate is removed by suction filtering.

Yield: 19 mg (96% of theory)
$C_{28}H_{32}N_4O_5$ (MW=504.584)
Mass spectrum: m/z=505 (M+H)$^+$ The following compounds of formula I are prepared analogously to Example 3:

| Example | R$^1$ | R$^2$ | R$^3$ | educt Yield [%] | Mass spectrum (ES) m/z | R$_f$ value (silica gel) (eluant) |
|---|---|---|---|---|---|---|
| 3.001 | Me | 4-carboxyphenyl | 1-methylpiperidin-4-yl | 1.077 / 99.8 | (M + H)$^+$ = 420 | 0.05 (A) |
| 3.002 | Me | 4-(carboxymethylcarbamoyl)phenyl | 1-methylpiperidin-4-yl | 4.002 / 88.5 | (M + H)$^+$ = 477 | 0.03 (A) |
| 3.003 | Me | 4-carboxyphenyl | trans-4-dimethylaminocyclohexyl | 1.078 / 96.1 | (M + H)$^+$ = 448 | 0.03 (C) |
| 3.004 | Me | Ph | trans-4-carboxycyclohexyl | 1.080 / 98.6 | (M + H)$^+$ = 405 | 0.47 (A) |
| 3.005 | Me | benzo[1,3]dioxol-5-yl | trans-4-carboxycyclohexyl | 1.035 / 94.3 | (M + H)$^+$ = 449 | 0.2 (A) |
| 3.006 | Me | 4-(2-carboxyethyl)phenyl | 1-methylpiperidin-4-yl | 1.074 / 98 | (M + H)$^+$ = 448 | 0.32 (MeOH) |

-continued

| Example | R¹ | R² | R³ | educt Yield [%] | Mass spectrum (ES) m/z | R_f value (silica gel) (eluant) |
|---|---|---|---|---|---|---|
| 3.007 | Me | (3-(4-substituted phenyl)propanoic acid with OH) | (4-((dimethylamino)methyl)cyclohexyl) | 1.075 97 | (M + H)⁺ = 490 | 0.25 (A) |
| 3.008 | Me | (3-(4-substituted phenyl)propanoic acid with OH) | (4-(dimethylamino)cyclohexyl) | 1.076 93.5 | (M + H)⁺ = 476 | 0.21 (MeOH) |
| 3.009 | Me | (benzo[1,3]dioxol-5-yl) | (4-substituted cyclohexanecarboxylic acid) | 20.00 84.0 | (M + H)⁺ = 464 | 0.39 (B) |
| 3.010 | Me | (2-(4-substituted phenoxy)acetic acid) | (cyclohexyl) | 1.097 71.0 | (M + H)⁺ = 435 | 0.09 (A) |
| 3.011 | Me | (2-(4-substituted phenoxy)acetic acid) | (1-methylpiperidin-4-yl) | 1.096 92.0 | (M + H)⁺ = 450 | 0.04 (A) |

EXAMPLE 4

5-acetyl-3-[(4-(2-dimethylamino-ethylcarbamoyl)-phenyl)-(1-methyl-piperidin-4-ylamino)-methylidene]-2-indolinone

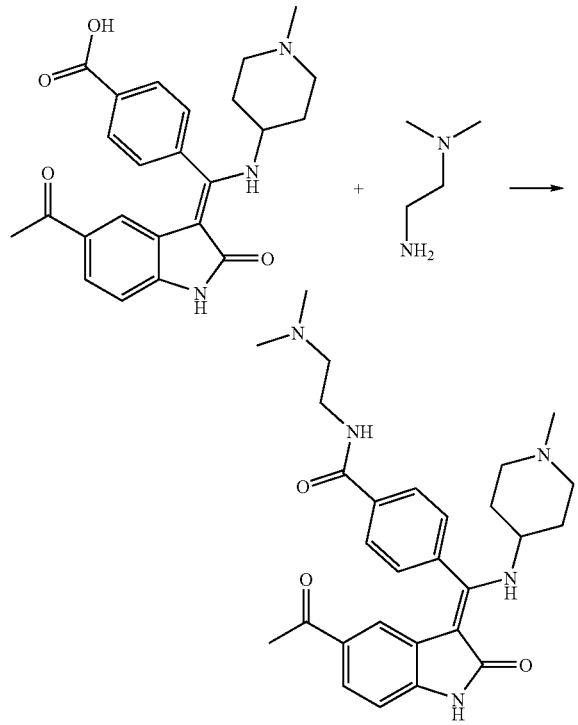

84 mg (0.2 mmol) 5-acetyl-3-[(4-carboxyl-phenyl)-(1-methyl-piperidin-4-ylamino)-methylidene]-2-indolinone (Example 3.001), 27 μl (0.24 mmol) N,N-dimethylethylene-diamine, 42 μl of Hünig base (ethyl-di-isopropylamine) and 77 mg TBTU (O-(benzo-triazol-1-yl)-N,N,N',N'-tetramethyluronium tetrafluoroborate) are stirred in 3 ml DMF (dimethylformamide) overnight at ambient temperature. Then the reaction mixture is combined with 5 ml 1N sodium hydroxide solution and extracted twice with 10 ml methylene chloride. The organic phases are dried over sodium sulphate and concentrated by rotary evaporation.

Yield: 70 mg (71% of theory)

$R_f$=0.18 (silica gel, methylene chloride/methanol/conc. ammonia 9:1:0.1)

$C_{28}H_{35}N_5O_3$ (MW=489.616)

Mass spectrum: m/z=490 (M+H)$^+$

The following compounds of formula I are prepared analogously to Example 4:

| Example | R$^1$ | R$^2$ | R$^3$ | educt Yield [%] | Mass spectrum (ES) m/z | R$_f$ value (silica gel) (eluant) |
|---|---|---|---|---|---|---|
| 4.001 | Me | ![structure: ethyl-NH-C(=O)-phenyl-] | ![structure: piperidine-N-CH3] | 3.002 78.4 | (M + H)$^+$ = 447 | 0.33 (C) |
| 4.002 | Me | ![structure: MeO-C(=O)-CH2-NH-C(=O)-phenyl-] | ![structure: piperidine-N-CH3] | 3.002 81.5 | (M + H)$^+$ = 491 | 0.33 (C) |

-continued

| Example | R[1] | R[2] | R[3] | educt Yield [%] | Mass spectrum (ES) m/z | R_f value (silica gel) (eluant) |
|---|---|---|---|---|---|---|
| 4.003 | Me | ethyl-NHC(O)-phenyl | 4-(N,N-dimethylamino)cyclohexyl | 3.002 58.5 | (M − H)⁻ = 473 | 0.09 (C) |
| 4.004 | Me | (dimethylamino)ethyl-NHC(O)-phenyl | 4-(N,N-dimethylamino)cyclohexyl | 3.002 60.8 | (M + H)⁺ = 518 | 0.03 (C) |
| 4.005 | Me | MeO-C(O)-CH₂-NHC(O)-phenyl | 4-(N,N-dimethylamino)cyclohexyl | 3.002 38.6 | (M + H)⁺ = 519 | 0.10 (C) |

EXAMPLE 5

5-acetyl-3-[3-(4-cis-(2-dimethylamino-ethyl-carbamoyl)-cyclohexylamino)-phenyl-methylidene]-2-indolinone

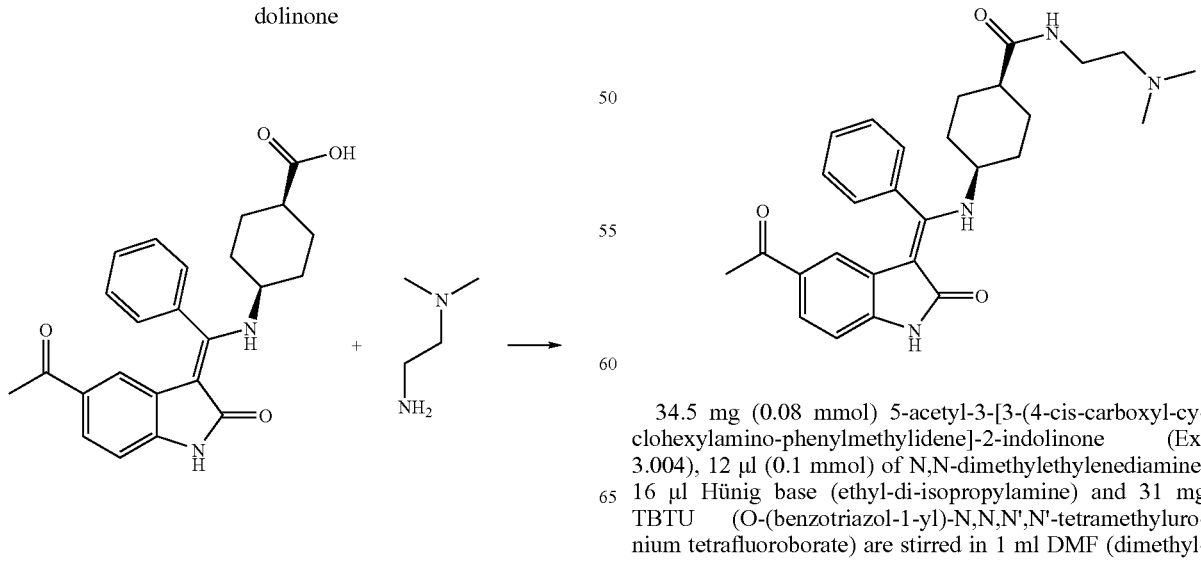

34.5 mg (0.08 mmol) 5-acetyl-3-[3-(4-cis-carboxyl-cyclohexylamino-phenylmethylidene]-2-indolinone (Ex. 3.004), 12 μl (0.1 mmol) of N,N-dimethylethylenediamine, 16 μl Hünig base (ethyl-di-isopropylamine) and 31 mg TBTU (O-(benzotriazol-1-yl)-N,N,N',N'-tetramethyluronium tetrafluoroborate) are stirred in 1 ml DMF (dimethylformamide) overnight at ambient temperature. Then the reaction mixture is combined with 3 ml 1 N sodium hydroxide solution and extracted twice with 10 ml methylene chloride. The organic phases are dried over sodium sulphate and concentrated by rotary evaporation.

Yield: 19 mg (50% of theory)

$R_f$=0.21 (methylene chloride/methanol/conc. ammonia 9:1:0.1)

$C_{28}H_{34}N_4O_3$ (MW=474.602)

Mass spectrum: m/z=475 (M+H)$^+$

The following compound of formula I is prepared analogously to Example 5:

| Example | R$^1$ | R$^2$ | R$^3$ | educt Yield [%] | Mass spectrum (ES) m/z | R$_f$ value (silica gel) (eluant) |
|---|---|---|---|---|---|---|
| 5.001 | Me | Ph | 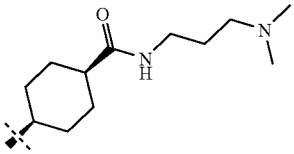 | 5.005 65.2 | (M + H)$^+$ = 489 | 0.10 (C) |
| 5.002 | Me | 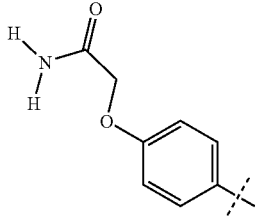 | 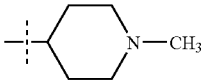 | 3.011 7.0 | (M + H)$^+$ = 449 | 0.17 (C) |
| 5.003 | Me | 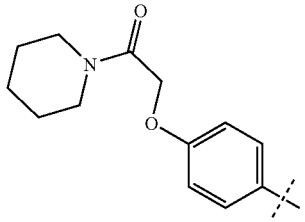 | 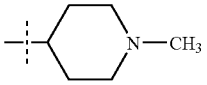 | 3.011 7.0 | (M + H)$^+$ = 517 | 0.22 (C) |
| 5.004 | Me | 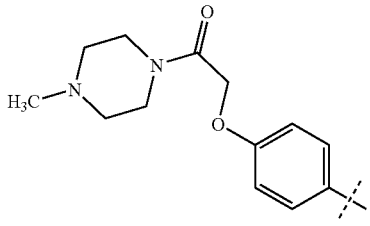 | 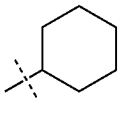 | 3.010 17.0 | (M + H)$^+$ = 517 | 0.25 (A) |

EXAMPLE 6
5-acetyl-3-[(4-aminomethyl-phenyl)-(1-methyl-piperidin-4-ylamino)-methylidene]-2-indolinone

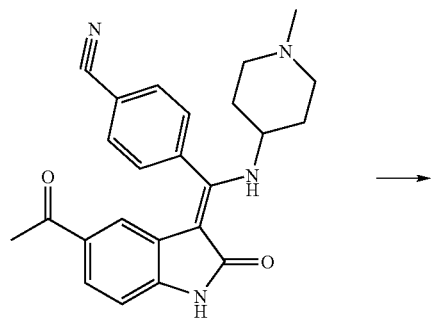

200 mg (0.5 mmol) 5-acetyl-3-[(4-cyano-phenyl)-(1-methyl-piperidin-4-ylamino)-methylidene]-2-indolinone (Example 1.057) are dissolved in 13 ml of methanolic ammonia, combined with 80 mg of Raney nickel and hydrogenated for 5 h at ambient temperature at a pressure of 50 psi. Then the catalyst is filtered off and the solution is evaporated down.

The residue is chromatographed through a silica gel column with methylene chloride:methanol 30:1. A solvent mixture comprising methylene chloride:methanol:conc. ammonia 10:1:0.1 is used to elute the product. The desired fraction is collected and evaporated down.

Yield: 113 mg (58% of theory)

$R_f$=0.20 (silica gel, methylene chloride/methanol 9:1)

$C_{24}H_{27}N_3O_2$ (MW=389.496)

Mass spectrum: m/z=390 (M+H)$^+$

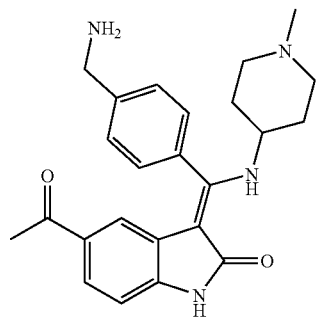

The following compounds of formula I are prepared analogously to Example 6:

| Example | $R^1$ | $R^2$ | $R^3$ | educt Yield [%] | Mass spectrum (ES) m/z | $R_f$ value (silica gel) (eluant) |
|---|---|---|---|---|---|---|
| 6.001 | Me | NH$_2$-CH$_2$-C$_6$H$_4$- | cyclohexyl | 1.056  58.3 | (M + H)$^+$ = 390 | 0.20 (A) |
| 6.002 | Me | NH$_2$-CH$_2$-C$_6$H$_4$- | 4-(N,N-dimethylamino)cyclohexyl | 1.067  79.2 | (M + H)$^+$ = 433 | 0.17 (C) |
| 6.003 | Me | NH$_2$-CH$_2$-C$_6$H$_4$- | cyclopentyl | 1.069  59.4 | (M + H)$^+$ = 376 | 0.36 (C) |

EXAMPLE 7

5-acetyl-3-[(4-acetylamino-methyl-phenyl)-(1-methyl-piperidin-4-ylamino)-methylidene]-2-indolinone

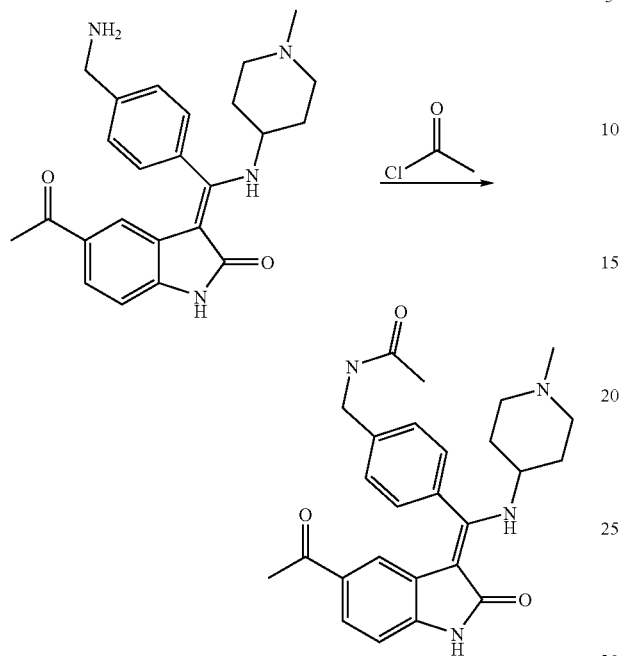

50 mg (0.12 mmol) 5-acetyl-3-[(4-aminomethyl-phenyl)-(1-methyl-piperidin-4-yl-amino)-methylidene]-2-indolinone (Example 6) are placed in 4 ml methylene chloride and combined with 40 μl triethylamine. 15 μl (0.21 mmol) acetyl chloride are added dropwise to this solution while cooling with ice and stirred for 10 min. Then the mixture is allowed to warm up to ambient temperature and stirred for 3 h. Then the solution is washed with water, the organic phase is dried over sodium sulphate, suction filtered and concentrated by rotary evaporation. The residue is eluted through a silica gel column with methylene chloride:methanol:conc. ammonia 20:1:0.1. The desired fraction is collected and evaporated down.

Yield: 48 mg (86% of theory)

$R_f$=0.25 (silica gel, methylene chloride/methanol 9:1)

$C_{26}H_{30}N_4O_3$ (MW=446.548)

Mass spectrum: m/z=447 $(M+H)^+$

The following compounds are prepared analogously to Example 7:

| Example | $R^1$ | $R^2$ | $R^3$ | educt Yield [%] | Mass spectrum (ES) m/z | $R_f$ value (silica gel) (eluant) |
|---|---|---|---|---|---|---|
| 7.001 | Me | HN-C(O)-CH₃ on 4-phenyl | cyclohexyl | 8.001 53.2 | $(M + H)^+$ = 432 | 0.39 (A) |
| 7.002 | Me | HN-C(O)-CH₃ on 4-phenyl | 4-(N,N-dimethylamino)cyclohexyl | 8.003 42.3 | $(M + H)^+$ = 475 | 0.36 (C) |
| 7.003 | Me | HN-C(O)-CH₃ on 4-phenyl | cyclopentyl | 8.007 41.9 | $(M + H)^+$ = 418 | 0.42 (C) |

EXAMPLE 8

5-acetyl-3-[(4-amino-phenyl)-(1-methyl-piperidin-4-ylamino)-methylidene]-2-indolinone

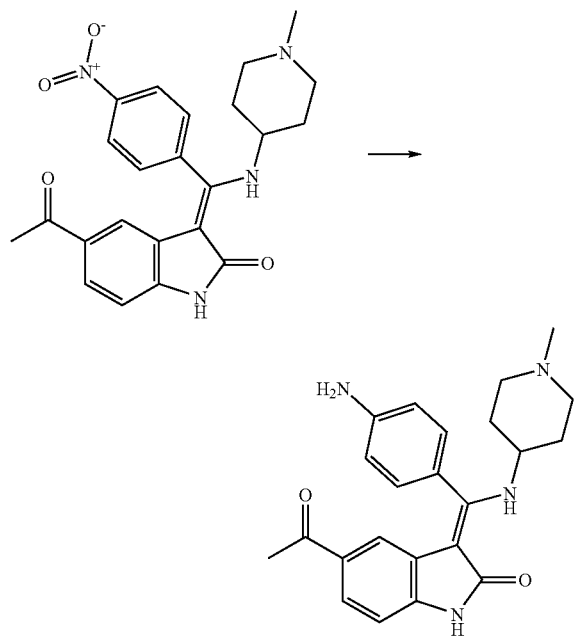

632 mg (1.5 mmol) 5-acetyl-3-[(4-nitro-phenyl)-(1-methyl-piperidin-4-ylamino)-methylidene]-2-indolinone (Example 1.012) are dissolved in 20 ml of tetrahydrofuran (THF) and 10 ml of ethyl acetate, combined with 70 mg Raney nickel and hydrogenated for 1 h at ambient temperature at a pressure of 50 psi. Then the catalyst is filtered off and the solution is evaporated down.

Yield: 560 mg (95% of theory)

$R_f$=0.31 (silica gel, methylene chloride/methanol/Konz. ammonia 9:1:0.1)

$C_{23}H_{26}N_4O_2$ (MW=390.484)

Mass spectrum: m/z=391 (M+H)$^+$

The following compound of formula I is prepared analogously to Example 8:

EXAMPLE 9

5-acetyl-3-[(3-acetylamino-phenyl)-(1-methyl-piperidin-4-ylamino)-methylidene]-2-indolinone

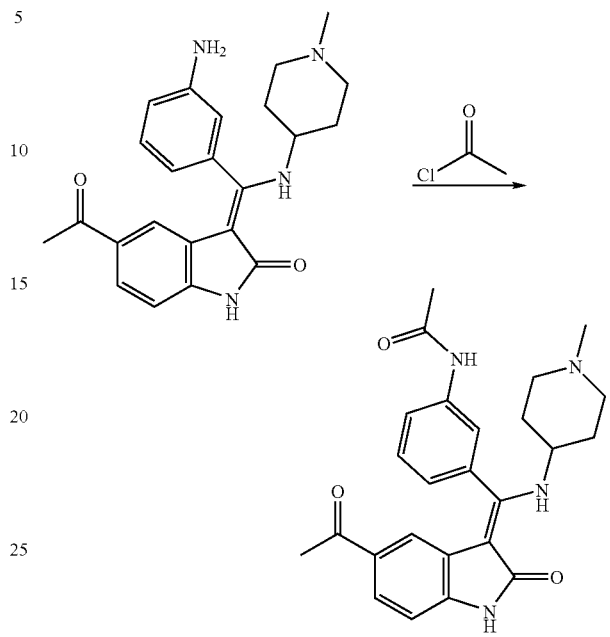

50 mg (0.11 mmol) 5-acetyl-3-[(3-amino-phenyl)-(1-methyl-piperidin-4-ylamino)-methylidene]-2-indolinone (Example 8.001) are placed in 5 ml methylene chloride and combined with 100 µl triethylamine. 15 µl (0.21 mmol) acetyl chloride are added dropwise to this solution while cooling with ice and stirred for 10 min. Then the mixture is allowed to come up to ambient temperature and stirred for another 1 h. Then 1 ml of 2N sodium hydroxide solution in 4 ml of methanol is added and the mixture is for 1 h at ambient temperature. Then the solution is combined with 10 ml methylene chloride, washed with water, the organic phase is dried over sodium sulphate, suction filtered and concentrated by rotary evaporation.

Yield: 44 mg (88% of theory)

$R_f$=0.12 (silica gel, methylene chloride/methanol 4:1)

$C_{25}H_{28}N_4O_3$ (MW=432.521)

Mass spectrum: m/z=433 (M+H)$^+$

| Example | R$^1$ | R$^2$ | R$^3$ | educt Yield [%] | Mass spectrum (ES) m/z | R$_f$ value (silica gel) (eluant) |
|---|---|---|---|---|---|---|
| 8.001 | Me | 3-NH$_2$-phenyl | 1-methyl-piperidin-4-yl | 2.079 35.5 | (M + H)$^+$ = 391 | 0.24 (C) |

The following compounds of formula I are prepared analogously to Example 9:

| Example | R¹ | R² | R³ | educt Yield [%] | Mass spectrum (ES) m/z | $R_f$ value (silica gel) (eluant) |
|---|---|---|---|---|---|---|
| 9.001 | Me | 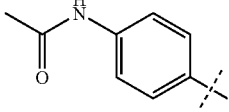 | 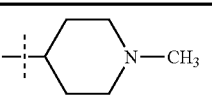 | 8.000 78.6 | $(M + H)^+ = 433$ | 0.24 (C) |
| 9.002 | Me | 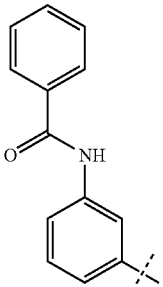 | 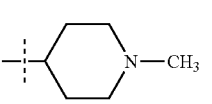 | 8.001 87 | $(M + H)^+ = 495$ | 0.19 (A) |
| 9.003 | Me | 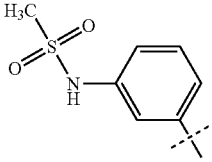 | 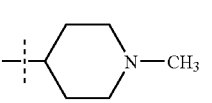 | 8.001 40.5 | $(M + H)^+ = 469$ | 0.34 (CH$_2$Cl$_2$/MeOH 1:1) |
| 9.004 | Me | 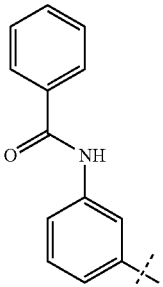 | 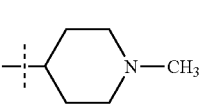 | 8.000 99 | $(M + H)^+ = 495$ | 0.18 (A) |

EXAMPLE 10

5-acetyl-3-[(4-methyl-piperazin-1-ylamino)-phenyl-methylidene]-2-indolinone

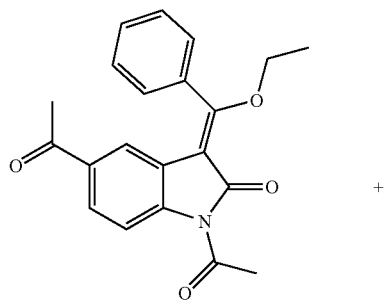

+

-continued

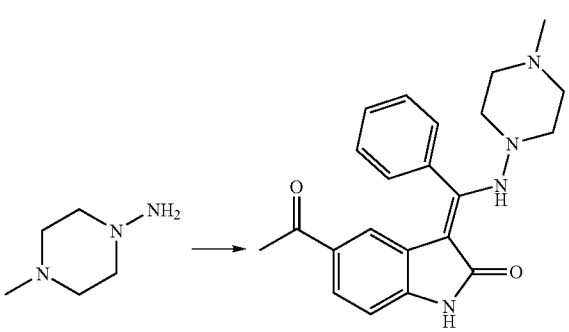

0.2 g (0.57 mmol) 1,5-diacetyl-3-[phenyl-ethoxy-methylidene]-2-indolinone (Ex. III) are suspended in 5 ml of dimethylformamide and stirred for 2 h at 80° C. with 0.1 ml of 1-amino-4-methylpiperazine. Then the mixture is left to cool, 0.4 ml of piperidine are added and the resulting mixture is stirred at ambient temperature for 30 min. The reaction mixture is evaporated down, the residue is taken up with 10 ml methylene chloride and the organic phase is washed with water, then dried with sodium sulphate and evaporated down. Then the compound is purified by chromatography on silica gel. Methylene chloride/methanol 50:1 is used as eluant.

Yield: 0.16 g (74% of theory)
$R_f$=0.28 (silica gel, methylene chloride/methanol 9:1)
$C_{22}H_{24}N_4O_2$ (MW=376.458)
Mass spectrum: m/z=377 (M+H)$^+$ The following compounds of formula I are prepared analogously to Example 10:

| Example | R$^1$ | R$^2$ | R$^3$ | educt Yield [%] | Mass spectrum (ES) m/z | R$_f$ value (silica gel) (eluant) |
|---|---|---|---|---|---|---|
| 10.001 | Me | 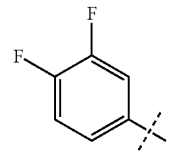 | 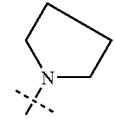 | VI.20 34.0 | (M + H)$^+$ = 413 | 0.69 (A) |
| 10.002 | Me | 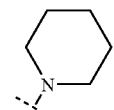 | 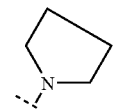 | VI.20 41.0 | (M + H)$^+$ = 384 | 0.81 (A) |
| 10.003 | Me | F$_3$C— | 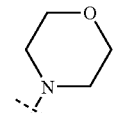 | VI.8 38.0 | (M + H)$^+$ = 430 | 0.69 (A) |
| 10.004 | Me | F$_3$C— | 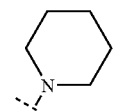 | VI.8 11.0 | (M + H)$^+$ = 414 | 0.70 (A) |
| 10.005 | Me | F$_3$C— | 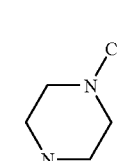 | VI.8 37.0 | (M + H)$^+$ = 432 | 0.70 (A) |
| 10.006 | Me | 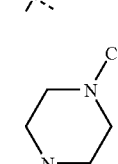 | | VI.20 33.0 | (M + H)$^+$ = 388 | 0.78 (A) |
| 10.007 | Me | Et | | III.3 61.0 | (M − H)$^-$ = 327 | 0.69 (A) |
| 10.008 | Me | Et | | III.3 60.0 | (M + H)$^+$ = 300 | 0.69 (A) |

-continued
| Example | R¹ | R² | R³ | educt Yield [%] | Mass spectrum (ES) m/z | $R_f$ value (silica gel) (eluant) |
|---|---|---|---|---|---|---|
| 10.009 | Me | Et | 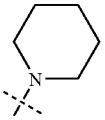 | III.3 37.0 | $(M + H)^+ = 312$ | 0.13 (D) |
| 10.010 | Me | Et | 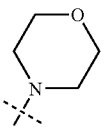 | III.3 73.0 | $(M + H)^+ = 314$ | 0.12 (D) |
| 10.011 | Me | 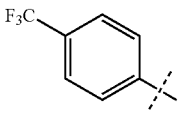 | 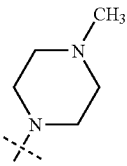 | VI.8 56.0 | $(M + H)^+ = 445$ | 0.36 (A) |
| 10.012 | Me | 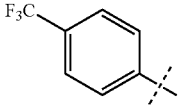 | 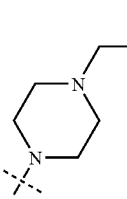 | VI.8 40.0 | $(M + H)^+ = 475$ | 0.32 (A) |
| 10.013 | Me | 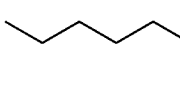 | 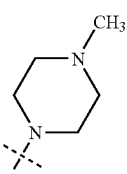 | VI.26 82.4 | $(M + H)^+ = 399$ | 0.35 (A) |
| 10.014 | Me | 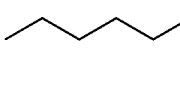 | 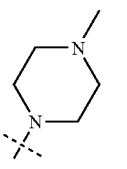 | VI.27 62.4 | $(M + H)^+ = 385$ | 0.47 (A) |
| 10.015 | Me | 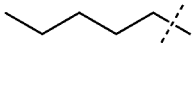 | 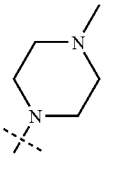 | VI.28 27.0 | $(M + H)^+ = 371$ | 0.50 (A) |
| 10.016 | Me | 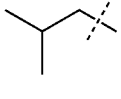 | 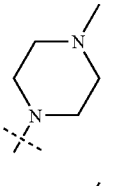 | VI.29 24.0 | $(M + H)^+ = 357$ | 0.28 (C) |
| 10.017 | Et | Et | 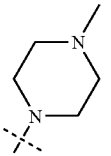 | III.7 56.0 | $(M + H)^+ = 343$ | 0.38 (A) |

-continued

| Example | R¹ | R² | R³ | educt Yield [%] | Mass spectrum (ES) m/z | $R_f$ value (silica gel) (eluant) |
|---|---|---|---|---|---|---|
| 10.018 | Am | Et | 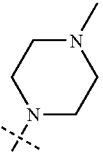 | III.8 60.0 | (M + H)⁺ = 385 | 0.37 (A) |

EXAMPLE 11

5-acetyl-3-[(1-methyl-piperidin-4-ylamino)-(4-pyrrol-1-yl-phenyl)-methylidene]-2-indolinone

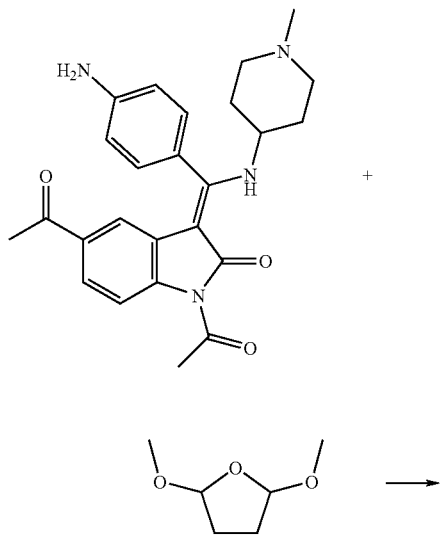

0.21 g (0.5 mmol) 1,5-diacetyl-3-[(1-methyl-piperidin-4-ylamino)-(4-aminophenyl)-methylidene]-2-indolinone (Ex. IX) are suspended in 5 ml of dimethylformamide and combined with 129 μl (1 mmol) 2,5-diethoxytetrahydrofuran and 110 mg phosphorus pentoxide. Then the mixture is heated to 220° C. for 5 min in a microwave. It is then left to cool, the solution is added to 20 ml of 1 N sodium hydroxide solution, stirred 10 min at ambient temperature and extracted three times with 20 ml methylechlorid/methanol 9:1. The combined organic phases are washed with water and concentrated by rotary evaporation. Then the compound is purified by chromatography on silica gel. Methylene chloride/methanol 4:1 is used as eluant.

Yield: 73 mg (33% of theory)

$R_f$=0.27 (silica gel, methylene chloride/methanol 9:1)

$C_{27}H_{28}N_4O_2$ (MW=440.550)

Mass spectrum: m/z=441 (M+H)⁺

The following compound is prepared analogously to Example 11:

EXAMPLE 11.001

5-acetyl-3-[(1-methyl-piperidin-4-ylamino)-(4-(2,5-dimethylpyrrol-1-yl)-phenyl)-methylidene]-2-indolinone Prepared from 1,5-diacetyl-3-[(1-methyl-piperidin-4-ylamino)-(4-aminophenyl)-methylidene]-2-indolinone (Ex. IX) and acetylacetone.

Yield: 52% of theory)

$R_f$=0.30 (silica gel, methylene chloride/methanol 9:1)

$C_{29}H_{32}N_4O_2$ (MW=468.604)

Mass spectrum: m/z=469 (M+H)⁺

EXAMPLE 12

5-acetyl-3-[(1-methyl-piperidin-4-ylamino)-(4-(1,3-dioxo-1,3-dihydroisoindol-2-yl-phenyl)-methylidene]-2-indolinone

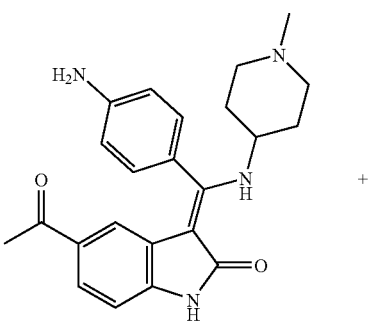

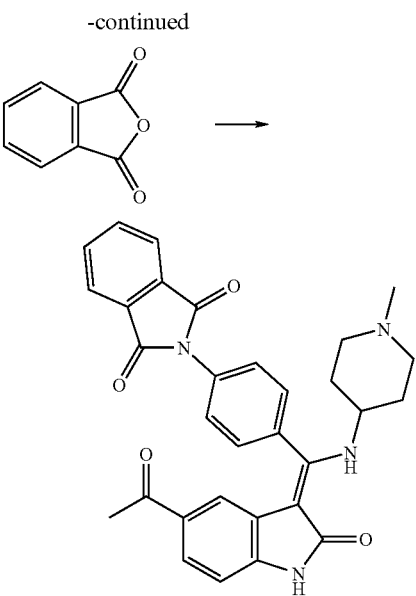

0.178 g (0.45 mmol) of 5-acetyl-3-[(1-methyl-piperidin-4-ylamino)-(4-aminophenyl)-methylidene]-2-indolinone (Ex. 8) are suspended in 3 ml of pyridine and combined with 100 mg phthalic anhydride. Then the mixture is heated to 220° C. for 10 min in a microwave. Then it is left to cool, the solution is added to 50 ml of water, stirred for 10 min at ambient temperature and the fine precipitate is suction filtered.

Yield: 173 mg (73% of theory)
$R_f$=0.24 (silica gel, methylene chloride/methanol 9:1)
$C_{31}H_{28}N_4O_4$ (MW=520.593)
Mass spectrum: m/z=521 (M+H)$^+$

EXAMPLE 13

5-acetyl-3-[(1-methyl-piperidin-4-ylamino)-(4-(2-dimethylamino-ethoxy-phenyl)-methylidene]-2-indolinone

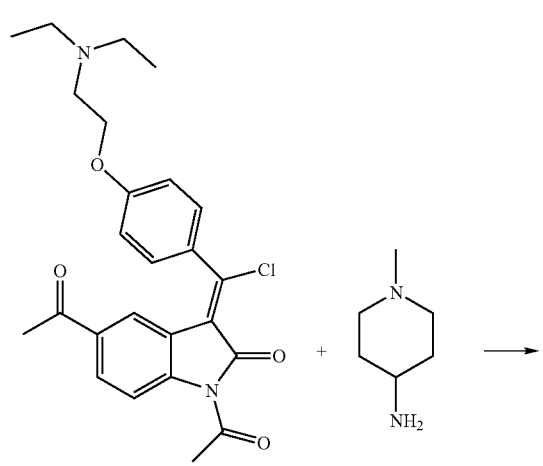

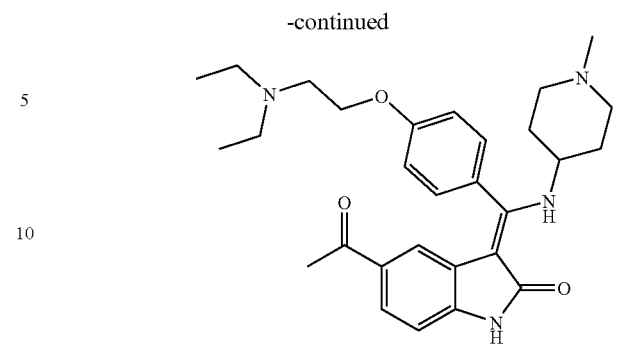

0.170 g (0.41 mmol) 1,5-diacetyl-3-[chloro-(4-(2-dimethylamino-ethoxy)-phenyl)-methylidene]-2-indolinone (Ex. VII.1) are dissolved in 5 ml of dimethylformamide and stirred with 200 mg 4-amino-1-methylpiperazin for 3 h at 80° C. Then the mixture is evaporated down and the residue is chromatographed through silica gel. The eluant used is a gradient consisting of methylene chloride/methanol 9:1 which is gradually changed to methylene chloride/methanol 1:1. The fractions are collected and concentrated by rotary evaporation.

Yield: 60 mg (30% of theory)
$R_f$=0.21 (silica gel, methylene chloride/methanol/conc. ammonia 9:1:0.1)
$C_{29}H_{38}N_4O_3$ (MW=490.651)
Mass spectrum: m/z=491 (M+H)$^+$

EXAMPLE 14

5-acetyl-3-[1-(1-methyl-piperidin-4-ylamino)-ethylidene]-2-indolinone

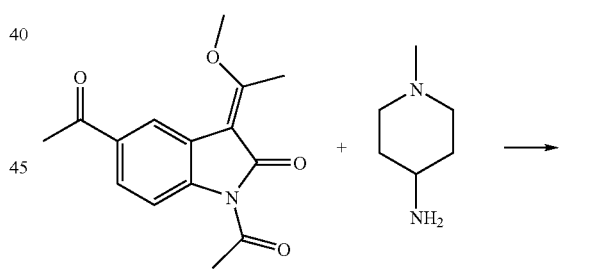

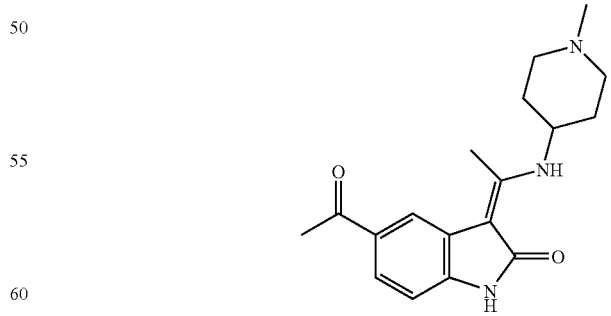

300 mg (1 mmol) 1,5-diacetyl-3-[-1-methoxy-methylidene]-2-indolinone (Ex. IV.2) are dissolved in 5 ml of dimethylformamide and stirred overnight with 0.125 g (1 mmol) of 4-amino-N-methylpiperidine at ambient temperature. The acetyl-protected intermediate product is combined with 1 ml of conc. ammonia without purification and stirred for one hour at ambient temperature. Then it is evaporated down and the residue is chromatographed through a silica gel column with methylene chloride/methanol 4:1 as eluant.

Yield: 200 mg (59% of theory)

$R_f$=0.17 (silica gel, methylene chloride/methanol 9:1)
$C_{18}H_{23}N_3O_2$ (MW=313.403)
Mass spectrum: m/z=314 (M+H)$^+$ The following compounds of formula I are prepared analogously to Example 14:

| Example | $R^1$ | $R^2$ | $R^3$ | educt Yield [%] | Mass spectrum (ES) m/z | $R_f$ value (silica gel) (eluant) |
|---|---|---|---|---|---|---|
| 14.001 | Me | Et | 1-methylpiperidin-4-yl | III.3 64.0 | (M + H)$^+$ = 328 | 0.28 (E) |
| 14.002 | Me | Et | 4-(N,N-dimethylamino)cyclohexyl | III.3 72.0 | (M + H)$^+$ = 356 | 0.28 (E) |
| 14.003 | Me | Et | [4-(N,N-dimethylamino)methyl]cyclohexyl | III.3 27.0 | (M + H)$^+$ = 370 | 0.30 (E) |
| 14.004 | Me | propyl | 1-methylpiperidin-4-yl | III.4 59.0 | (M − H)$^−$ = 340 | 0.40 (C) |
| 14.005 | Me | propyl | 4-(N,N-dimethylamino)cyclohexyl | III.4 79.0 | (M − H)$^−$ = 368 | 0.42 (C) |
| 14.006 | Me | propyl | [4-(N,N-dimethylamino)methyl]cyclohexyl | III.4 71.0 | (M − H)$^−$ = 382 | 0.52 (C) |
| 14.007 | Me | butyl | 1-methylpiperidin-4-yl | III.5 74.0 | (M + H)$^+$ = 356 | 0.37 (A) |

-continued

| Example | R¹ | R² | R³ | educt Yield [%] | Mass spectrum (ES) m/z | $R_f$ value (silica gel) (eluant) |
|---|---|---|---|---|---|---|
| 14.008 | Me | (propyl) | (H₃C-N(CH₃)-cyclohexyl) | III.5 82.0 | $(M + H)^+ = 384$ | 0.17 (A) |
| 14.009 | Me | (propyl) | (CH₂-N(CH₃)₂-cyclohexyl) | III.5 69.0 | $(M - H)^- = 396$ | 0.28 (A) |
| 14.010 | Me | (tBu) | (N-methylpiperidinyl) | III.6 33.0 | $(M + H)^+ = 342$ | 0.42 (C) |
| 14.011 | Me | (tBu) | (H₃C-N(CH₃)-cyclohexyl) | III.6 43.0 | $(M + H)^+ = 370$ | 0.17 (C) |

EXAMPLE 15

5-acetyl-3-[(pyrazin-2-yl)-(4-dimethylamino-cyclohexylamino)-methylidene]-2-indolinone

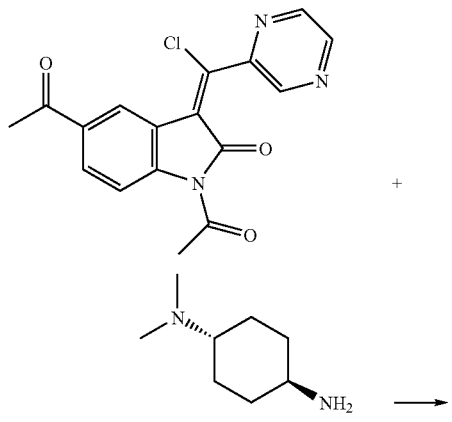

+

-continued

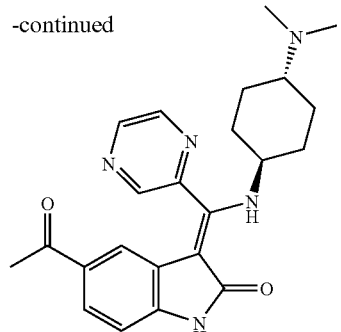

100 mg (0.29 mmol) 1,5-diacetyl-3-[chloro-pyrazin-2-yl-methylidene]-2-indolinone (Ex. VII) are stirred overnight in 4 ml of tetrahydrofuran with 0.06 ml triethylamine and 0.05 g N,N-dimethyl-cyclohexane-1,4-diamine at ambient temperature. The acetyl-protected intermediate product is combined with 0.8 ml of conc. ammonia without purification and stirred for half an hour at ambient temperature. Then the mixture is evaporated down and the residue is chromatographed through a silica gel column with methylene chloride/methanol 4:1 as eluant.

Yield: 40 mg (34% of theory)

$R_f$=0.05 (silica gel, methylene chloride/methanol 9:1)

$C_{23}H_{27}N_5O_2$ (MW=405.504)

Mass spectrum: m/z=404 (M−H)⁻

The following compound of formula I is prepared analogously to Example 15:

| Example | R¹ | R² | R³ | educt Yield [%] | Mass spectrum (ES) m/z | R_f value (silica gel) (eluant) |
|---|---|---|---|---|---|---|
| 15.001 | Me | pyrazin-2-yl | 1-methyl-piperidin-4-yl | VII 18.1 | (M + H)⁺ = 378 | 0.12 (A) |

EXAMPLE 16

5-acetyl-3-[(Pyridin-4-yl)-(1-methyl-piperidin-4-ylamino)-methylidene]-2-indolinone

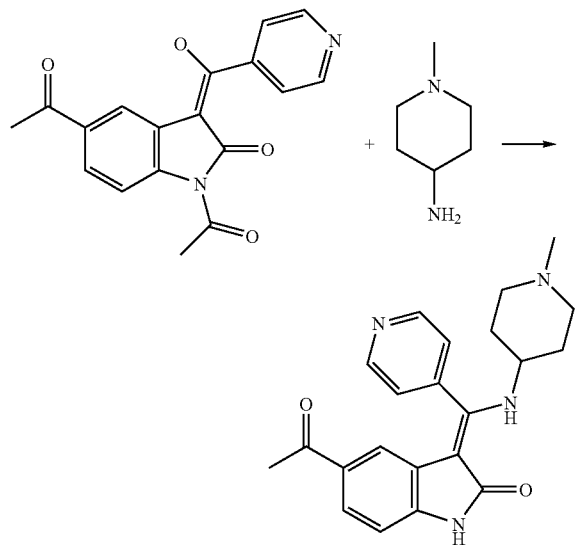

250 mg (0.77 mmol) 1,5-diacetyl-3-[(pyridin-4-yl)-hydroxy-methylidene]-2-indolinone (Ex. V.24) are heated with 1.2 ml hexamethyldisilazane, 0.14 g 4-amino-1-methyl-piperidine and 10 mg p-toluenesulphonic acid for 3 h at 120° C. Then the mixture is left to cool and 5 ml of methanol and 35 mg sodium methoxide are added and stirred for 1 h at ambient temperature. Then the mixture is evaporated down and the residue is chromatographed through a silica gel column with methylene chloride/methanol/conc. ammonia 4:1:0.1 as eluant.

Yield: 90 mg (21% of theory)

$R_f$=0.56 (silica gel, methylene chloride/methanol/conc. ammonia 4:1:0.1)

$C_{22}H_{24}N_4O_2$ (MW=376.46)

Mass spectrum: m/z=377 (M+H)⁺

The following compounds of formula I are prepared analogously to Example 16:

| Example | R¹ | R² | R³ | educt Yield [%] | Mass spectrum (ES) m/z | R_f value (silica gel) (eluant) |
|---|---|---|---|---|---|---|
| 16.001 | Me | pyridin-4-yl | 4-(dimethylamino)cyclohexyl | V.24 21.2 | (M + H)⁺ = 405 | 0.4 (C) |

-continued

| Example | R¹ | R² | R³ | educt Yield [%] | Mass spectrum (ES) m/z | R_f value (silica gel) (eluant) |
|---|---|---|---|---|---|---|
| 16.002 | Me | (CH₂N(Et)₂-benzyl) | N(CH₃)₂-cyclohexyl | V.26 49.9 | (M + H)⁺ = 489 | 0.49 (C) |
| 16.003 | Me | (Et₂N-CH₂CH₂-O-phenyl) | cyclohexyl | V.29 7.0 | (M + H)⁺ = 476 | 0.63 (A) |
| 16.004 | Me | (Et₂N-CH₂CH₂-O-phenyl) | cyclopentyl | V.29 7.0 | (M + H)⁺ = 462 | 0.23 (A) |
| 16.005 | Me | (Et₂N-CH₂CH₂-O-phenyl) | N(CH₃)₂-cyclohexyl | V.29 14.0 | (M + H)⁺ = 519 | 0.66 (C) |
| 16.006 | Me | (meta-Et₂N-CH₂CH₂-O-phenyl) | N(CH₃)₂-cyclohexyl | V.30 + trimethyl silyl-imidazole 66.0 | (M + H)⁺ = 519 | 0.72 (C) |
| 16.007 | Me | (meta-Et₂N-CH₂CH₂-O-phenyl) | cyclohexyl | V.30 + trimethyl silyl-imidazole 21.0 | (M + H)⁺ = 476 | 0.68 (C) |

EXAMPLE 17

5-acetyl-3-[furan-3-yl-(1-methyl-piperidin-4-ylamino)-methylidene]-2-indolinone

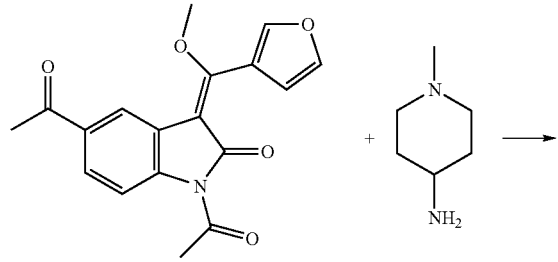

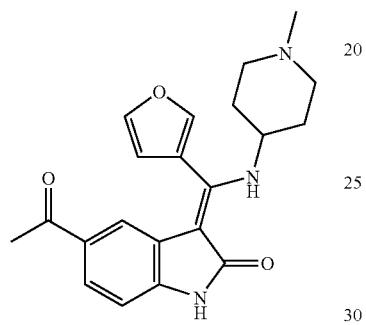

200 mg (0.65 mmol) 1,5-diacetyl-3-[furan-3-yl-methoxy-methylidene]-2-indolinone (Ex. VI.23) are suspended in 5 ml of dimethylformamide and stirred overnight with 73 mg 4-amino-N-methylpiperidin at ambient temperature. The acetyl-protected intermediate product is combined with 1 ml of conc. ammonia without purification and stirred at ambient temperature for 30 min. Then it is evaporated down and the residue is chromatographed through a silica gel column with methylene chloride/methanol 4:1 as eluant.

Yield: 77 mg (32% of theory)
$R_f$=0.18 (silica gel, methylene chloride/methanol 9:1)
$C_{24}H_{25}N_3O_4$ (MW=419.479)
Mass spectrum: m/z=420 (M+H)$^+$ The following compound of formula I is prepared analogously to Example 17:

EXAMPLE 18

5-acetyl-3-[(benzo[1,3]dioxol-5-yl)-(1-acetyl-piperidin-4-ylamino)-methylidene]-2-indolinone

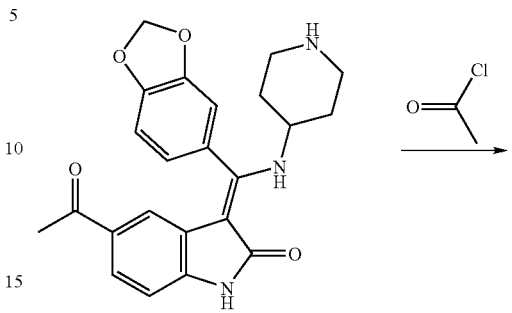

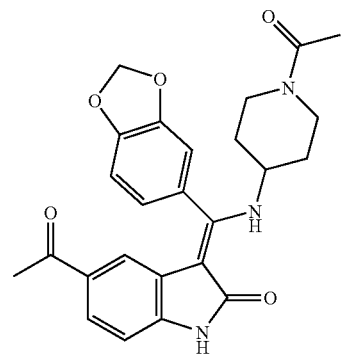

200 mg (0.38 mmol) 5-acetyl-3-[(benzo[1,3]dioxol-5-yl)-(piperidin-4-ylamino)-methylidene]-2-indolinone (Ex. 2.004) are dissolved with 0.11 ml triethylamine in 5 ml methylene chloride (dichloromethane). 0.03 ml (0.39 mmol) acetyl chloride are added dropwise to the solution. This solution is stirred overnight at ambient temperature, washed with water and the organic phase is dried with sodium sulphate. The methylene chloride phase is concentrated by rotary evaporation and triturated with a little diethyl ether. The residue may be chromatographed through a silica gel column with methylene chloride/methanol/conc. ammonia 4:1:0.1 as eluant.

Yield: 67 mg (39% of theory)
$R_f$=0.86 (silica gel, methylene chloride/methanol 9:1)
$C_{25}H_{25}N_3O_5$ (MW=447.48)
Mass spectrum: m/z=448 (M+H)$^+$ The following compounds of formula I are prepared analogously to Example 18:

| Example | $R^1$ | $R^2$ | $R^3$ | educt Yield [%] | Mass spectrum (ES) m/z | $R_f$ value (silica gel) (eluant) |
|---|---|---|---|---|---|---|
| 17.001 | Me | ![furan] | ![N-methylcyclohexyl-N-methyl] | VI.23 62.1 | (M + H)$^+$ = 394 | 0.09 (A) |

| Example | R¹ | R² | R³ | educt Yield [%] | Mass spectrum (ES) m/z | $R_f$ value (silica gel) (eluant) |
|---|---|---|---|---|---|---|
| 18.001 | Me | benzo[1,3]dioxol-5-yl | -C(O)-CH₂-N(CH₃)₂-piperidinyl | 2.004<br>14.0 | (M + H)⁺ = 491 | 0.63 (A) |
| 18.002 | Me | benzo[1,3]dioxol-5-yl | -S(O)₂-CH₃-piperidinyl | 2.004<br>55.0 | (M + H)⁺ = 484 | 0.47 (A) |
| 18.003 | Me | benzo[1,3]dioxol-5-yl | -C(O)-N(CH₃)₂-piperidinyl | 2.004 + dimethylcarbamoyl chloride<br>82.0 | (M + H)⁺ = 477 | 0.81 (A) |

EXAMPLE 19

5-acetyl-3-[(benzo[1,3]dioxol-5-yl)-(1-(2-tert-butoxycarbonylamine-acetyl-piperidin-4-ylamino)-methylidene]-2-indolinone

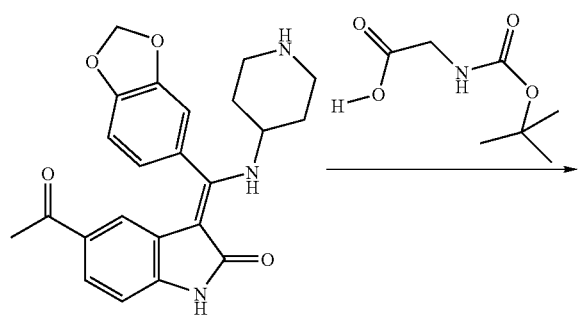

400 mg (0.77 mmol) 5-acetyl-3-[(benzo[1,3]dioxol-5-yl)-(piperidin-4-ylamino)-methylidene]-2-indolinone (Ex. 2.004) are dissolved together with 0.67 ml Hünig base (ethyldiisopropylamine), 135 mg (0.77 mmol) BOC-Glycine and 300 mg TBTU (O-benzotriazol-1-yl-N,N,N',N'-tetramethyluronium tetrafluoroborate) in 10 ml of dimethylformamide (DMF) and stirred at ambient temperature for 48 h. Then the solution is concentrated by evaporation and the residue is taken up in 10 ml methylene chloride. The solution is washed with 5 ml of water and the organic phase is dried over sodium sulphate and concentrated by evaporation. The residue is washed with a little ether or chromatographed through a silica gel column with methylene chloride/methanol/conc. ammonia 4:1:0.1 as eluant.

Yield: 280 mg (65% of theory)

$R_f$=0.38 (silica gel, methylene chloride/methanol 9:1)

$C_{30}H_{34}N_4O_7$ (MW=562.61)

Mass spectrum: m/z=563 (M+H)⁺

The following compounds of formula I are prepared analogously to Example 19:

| Example | R¹ | R² | R³ | educt Yield [%] | Mass spectrum (ES) m/z | R_f value (silica gel) (eluant) |
|---|---|---|---|---|---|---|
| 19.001 | Me | 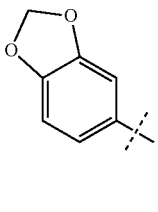 | 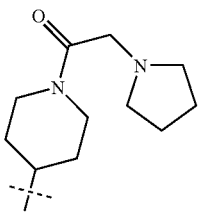 | 2.004 33.0 | (M + H)⁺ = 517 | 0.32 (A) |
| 19.002 | Me | 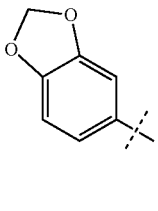 | 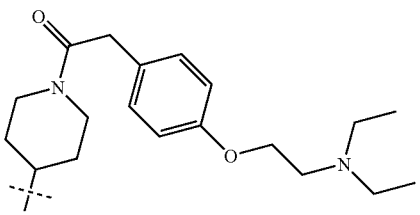 | 2.004 41.0 | (M + H)⁺ = 639 | 0.56 (B) |
| 19.003 | Me | 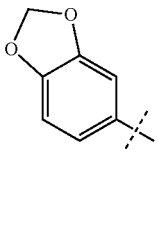 | 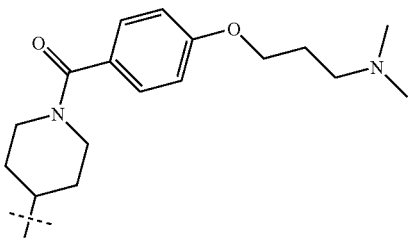 | 2.004 30.0 | (M + H)⁺ = 611 | 0.54 (B) |
| 19.004 | Me | 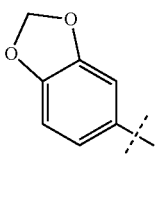 | 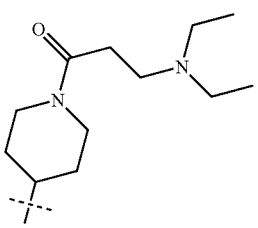 | 2.004 32.0 | (M + H)⁺ = 533 | 0.40 (B) |
EXAMPLE 20
5-acetyl-3-[(benzo[1,3]dioxol-5-yl)-(1-methoxycarbonyl-methyl-piperidin-4-ylamino)-methylidene]-2-indolinone
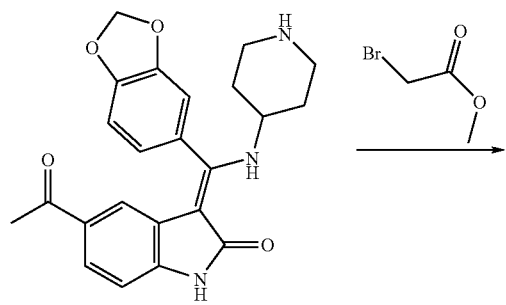
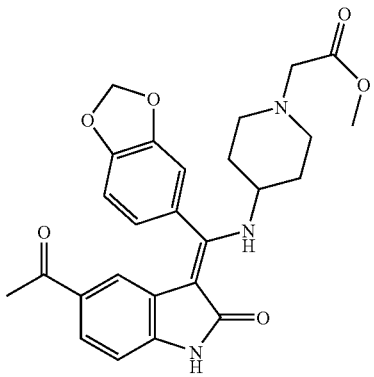
2 g (3.85 mmol) 5-acetyl-3-[(benzo[1,3]dioxol-5-yl)-(piperidin-4-ylamino)-methylidene]-2-indolinone (Ex. 2.004) are dissolved with 1.4 ml Hünig base (ethyldiisopropylamine) and 0.395 ml (3.9 mmol) methyl bromoacetate in 20 ml acetonitrile and refluxed for 3 h. Then the solution is concentrated by evaporation and the residue is taken up in 40 ml of ethyl acetate. The organic phase is washed with 10 ml of water, dried over sodium sulphate, filtered through silica gel and concentrated by evaporation.

Yield: 1.1 g (60% of theory)
$R_f$=0.40 (silica gel, methylene chloride/methanol 9:1)
$C_{26}H_{27}N_3O_6$ (MW=477.51)
Mass spectrum: m/z=478 (M+H)$^+$

EXAMPLE 21

5-acetyl-3-[(benzo[1,3]dioxol-5-yl)-(1-(2-oxo-2-morpholin-4-yl-ethyl)-piperidin-4-ylamino)-methylidene]-2-indolinone

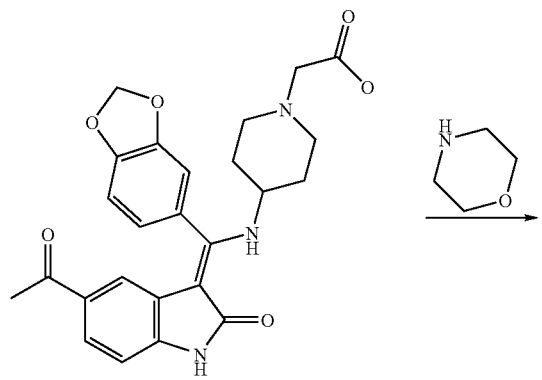

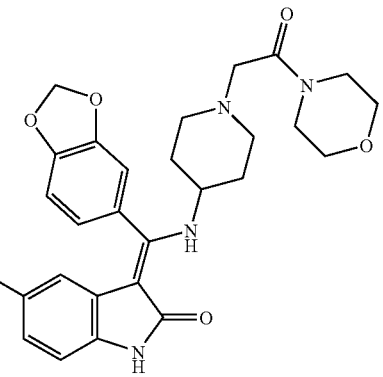

100 mg (0.21 mmol) 5-acetyl-3-[(benzo[1,3]dioxol-5-yl)-(1-carboxy-methyl-piperidin-4-ylamino)-methylidene]-2-indolinone (Ex. 3.009) are dissolved in 4 ml of dimethylformamide and stirred with 40 mg carbonyldiimidazole and 0.02 ml (0.22 mmol) morpholine for 2 h at 70°. Then the solution is concentrated by evaporation and the residue is stirred with a little diethyl ether and the residue is suction filtered.

Yield: 87 mg (76% of theory)
$R_f$=0.39 (silica gel, methylene chloride/methanol 9:1)
$C_{29}H_{32}N_4O_6$ (MW=532.59)
Mass spectrum: m/z=533 (M+H)$^+$ The following compounds of formula I are prepared analogously to Example 21:

| Example | R$^1$ | R$^2$ | R$^3$ | educt Yield [%] | Mass spectrum (ES) m/z | R$_f$ value (silica gel) (eluant) |
|---|---|---|---|---|---|---|
| 21.001 | Me | 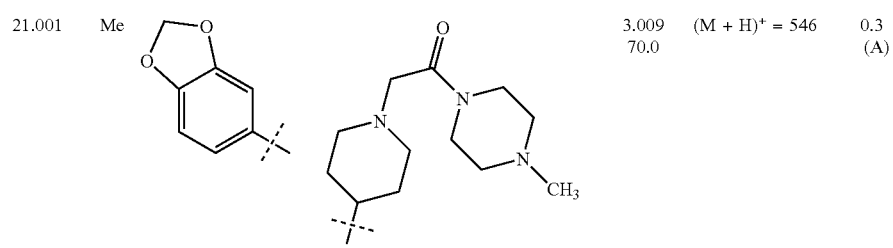 | | 3.009 70.0 | (M + H)$^+$ = 546 | 0.3 (A) |
| 21.002 | Me | 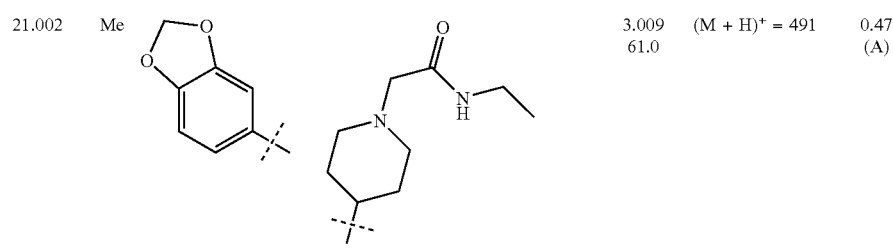 | | 3.009 61.0 | (M + H)$^+$ = 491 | 0.47 (A) |

-continued

| Example | R¹ | R² | R³ | educt Yield [%] | Mass spectrum (ES) m/z | $R_f$ value (silica gel) (eluant) |
|---|---|---|---|---|---|---|
| 21.003 | Me | 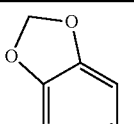 | 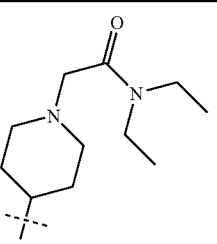 | 3.009<br>27.0 | $(M + H)^+ = 519$ | 0.38<br>(A) |
| 21.004 | Me | 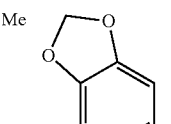 | 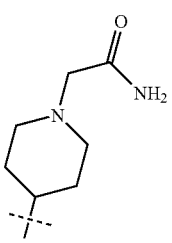 | 3.009<br>85.0 | $(M + H)^+ = 463$ | 0.40<br>(A) |

EXAMPLE 22

5-acetyl-3-[(benzo[1,3]dioxol-5-yl)-(1-butylcarbamoyl-piperidin-4-ylamino)-methylidene]-2-indolinone

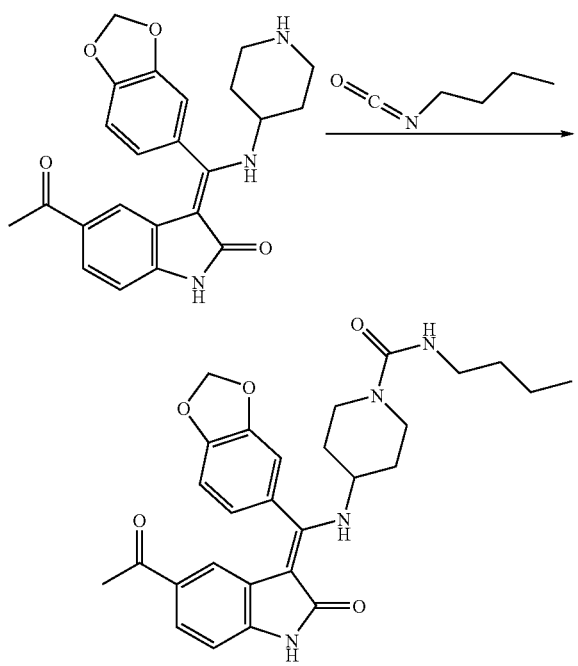

200 mg (0.38 mmol) 5-acetyl-3-[(benzo[1,3]dioxol-5-yl)-(piperidin-4-ylamino)-methylidene]-2-indolinone (Ex. 2.004) are dissolved with 0.05 ml butylisocyanate in 5 ml methylene chloride (dichloromethane). This solution is stirred overnight at ambient temperature, then washed with water and the organic phase is dried with sodium sulphate. The methylene chloride phase is concentrated by rotary evaporation and triturated with a little diethyl ether.

Yield: 130 mg (67% of theory)
$R_f$=0.89 (silica gel, methylene chloride/methanol 9:1)
$C_{28}H_{32}N_4O_5$ (MW=504.578)
Mass spectrum: m/z=505 $(M+H)^+$

EXAMPLE 23

| Coated tablets containing 75 mg of active substance | |
|---|---|
| 1 tablet core contains: | |
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 24

Tablets containing 100 mg of active substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

EXAMPLE 25

Tablets containing 150 mg of active substance

Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

EXAMPLE 26

Hard gelatine capsules containing 150 mg of active substance 1 capsule contains:

| | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE 27

Suppositories containing 150 mg of active substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 28

Suspension containing 50 mg of active substance 100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 29

Ampoules containing 10 mg active substance

Composition:

| | |
|---|---|
| active substance | 10.0 mg |
| 0.01 N hydrochloric acid q.s. | |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 30

| Ampoules containing 50 mg of active substance | |
|---|---|
| Composition: | |
| active substance | 50.0 mg |
| 0.01 N hydrochloric acid q.s. | |
| double-distilled water | ad 10.0 ml |

Preparation:

The active substance is dissolved in the necessary amount of 0.01 N HCl, made isotonic with common salt, filtered sterile and transferred into 10 ml ampoules.

The invention claimed is:
1. Compounds of general formula

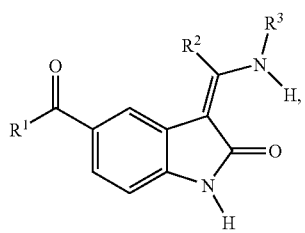

(I)

wherein
- $R^1$ denotes a straight-chain or branched $C_{1-5}$-alkyl group wherein the hydrogen atoms may be wholly or partly replaced by fluorine atoms, or
  an aryl group optionally substituted by a fluorine, chlorine or bromine atom,
  while by an aryl group is meant a phenyl or naphthyl group,
- $R^2$ denotes a straight-chain or branched $C_{1-7}$-alkyl or $C_{3-7}$-cycloalkyl group,
  a 5- or 6-membered heteroaryl group with one to three heteroatoms selected from the group N, S and O, optionally substituted by one or two fluorine, chlorine, bromine or iodine atoms or one or two nitro, cyano, amino, $C_{1-3}$-alkyl or $C_{1-3}$-alkoxy groups, while both the heteroatoms and the substituents may be identical or different,
  a phenyl group wherein two adjacent carbon atoms are linked together through a methylenedioxy, ethylenedioxy or difluoromethylenedioxy group,
  a phenyl group, to which another phenyl ring or a 5- or 6-membered heteroaromatic ring with one to three heteroatoms selected from the group N, S and O, wherein the heteroatoms may be identical or different, is anellated, while the bicyclic group may be substituted by one or two fluorine, chlorine, bromine or iodine atoms or one or two nitro, cyano, amino, $C_{1-3}$-alkyl or $C_{1-3}$-alkoxy groups and the substituents may be identical or different, or
  a phenyl group which may be substituted by one to three fluorine, chlorine, bromine or iodine atoms or by one to three $C_{1-3}$-alkyl, nitro, cyano, amino, di-($C_{1-3}$-alkyl)-amino, $C_{1-3}$-alkyl-carbonylamino, phenylcarbonylamino, $C_{1-3}$-alkylsulphonylamino, arylsulphonylamino, trifluoromethyl, $C_{1-3}$alkylsulphonyl, carboxy, $C_{1-3}$-alkoxy, di-($C_{1-3}$-alkyl)-amino-$C_{1-3}$-alkyloxy, $C_{1-3}$-alkoxy-carbonyl, $C_{1-3}$-alkylaminocarbonyl, hydroxy-carbonyl-$C_{1-3}$-alkyl-aminocarbonyl, $C_{1-3}$-alkoxy-carbonyl-$C_{1-3}$-alkyl-aminocarbonyl, amino-$C_{1-3}$-alkyl-aminocarbonyl, $C_{1-3}$-alkyl-amino-$C_{1-3}$-alkyl-aminocarbonyl, di-($C_{1-3}$-alkyl)-amino-$C_{1-3}$-alkylaminocarbonyl, di-($C_{1-3}$-alkyl)-amino-carbonyl-$C_{1-3}$-alkoxy, $C_{1-3}$-alkyl-amino-carbonyl-$C_{1-3}$-alkoxy, amino-carbonyl-$C_{1-3}$-alkoxy, carboxy-$C_{1-3}$-alkoxy, $C_{1-3}$-alkyloxy-carbonyl-$C_{1-3}$-alkoxy, piperidinylcarbonyl-$C_{1-3}$-alkoxy, piperazinylcarbonyl-$C_{1-3}$-alkoxy, 4-($C_{1-3}$-alkyl)-piperazinylcarbonyl-$C_{1-3}$-alkoxy, carboxy-$C_{1-3}$-alkyl, $C_{1-3}$-alkoxy-carbonyl-$C_{1-3}$-alkyl, amino-$C_{1-3}$-alkyl, di-($C_{1-3}$-alkyl)-amino-$C_{1-3}$-alkyl, $C_{1-3}$-alkyl-carbonylamino-$C_{1-3}$-alkyl, phthalimido, pyrrolyl or mono- or di-($C_{1-3}$-alkyl)-pyrrolyl groups, while the substituents are identical or different, and
- $R^3$ denotes a $C_{3-8}$-cycloalkyl group,
  a cyclohexyl, cyclohexenyl, cycloheptyl, cyclooctyl, cyclopentenyl or cyclopentyl group which is substituted by a hydroxy, $C_{1-3}$-alkoxy, $C_{1-3}$-alkyl, amino, $C_{1-3}$-alkyl-amino, di-($C_{1-3}$-alkyl)-amino, $C_{1-4}$-alkyloxy-carbonyl-amino, di-($C_{1-3}$-alkyl)-amino-$C_{1-3}$-alkyl, N-($C_{1-3}$-alkyl)-N-(phenyl-$C_{1-3}$-alkyl)-amino-$C_{1-3}$-alkyl, piperidino-$C_{1-3}$-alkyl, piperazino-$C_{1-3}$-alkyl, 4-($C_{1-3}$-alkyl)-piperazino-$C_{1-3}$-alkyl, pyrrolidino-$C_{1-3}$-alkyl, 2-oxo-pyrrolidino-$C_{1-3}$-alkyl, morpholino-$C_{1-3}$-alkyl, carboxy, $C_{1-4}$-alkoxy-carbonyl, di-($C_{1-3}$-alkyl)-amino-$C_{1-3}$-alkyl-aminocarbonyl, amino-$C_{1-3}$-alkyloxy, $C_{1-3}$-alkyl-amino-$C_{1-3}$-alkyloxy, di-($C_{1-3}$-alkyl)-amino-$C_{1-3}$-alkyloxy or ethylenedioxy group,
  a cyclopentyl or cyclohexyl group wherein the methylene group in position 3 or 4 is replaced in each case by an oxygen or a sulphur atom, a sulphonyl group or a sulphinyl group,
  a cyclohexyl group which is substituted by a $C_{1-3}$-alkyl and a hydroxy group,
  a 5- to 7-membered cycloalkyleneimino group wherein the methylene group in the 4 position may be replaced by an oxygen or a sulphur atom, a sulphonyl group or a sulphinyl group,
  a piperidin-4-yl, piperidin-3-yl, homopiperidin-4-yl or pyrrolidin-3-yl group which may be substituted at the amino-nitrogen atom by a straight-chain or branched $C_{1-5}$-alkyl, benzyl, $C_{1-5}$-alkyl-carbonyl, $C_{1-5}$-alkyl-sulphonyl, phenyl-carbonyl, phenyl-sulphonyl, hydroxy-carbonyl-$C_{1-3}$-alkyl, morpholinocarbonyl-$C_{1-3}$-alkyl, $C_{1-4}$alkoxy-carbonyl-$C_{1-3}$-alkyl, $C_{1-4}$-alkoxy-carbonyl, di-($C_{1-3}$alkyl)-amino-carbonyl, $C_{1-5}$-alkyl-amino-carbonyl, $C_{1-3}$-alkylamino-sulphonyl, $C_{1-4}$-alkoxy-carbonyl-$C_{1-3}$-alkyl, di-($C_{1-3}$alkyl)-amino-carbonyl-$C_{1-3}$-alkyl, $C_{1-3}$-alkyl-amino-carbonyl-$C_{1-3}$-alkyl, amino-carbonyl-$C_{1-3}$-alkyl, di-($C_{1-3}$-alkyl)-amino-$C_{1-3}$-alkyl-carbonyl, $C_{1-3}$-alkyl-amino-$C_{1-3}$-alkyl-carbonyl, amino-$C_{1-3}$-alkyl-carbonyl, di-($C_{1-3}$-alkyl)-amino-$C_{1-3}$-alkyl-aminocarbonyl, $C_{1-4}$-alkyloxy-carbonyl-amino-$C_{1-3}$-alkyl-carbonyl, 4-[di-($C_{1-3}$-alkyl)-amino-$C_{1-3}$-alkyloxy]-phenyl-carbonyl, 4-[di-($C_{1-3}$-alkyl)-amino-$C_{1-3}$-alkyloxy]-phenyl-$C_{1-3}$-alkyl-carbonyl or pyrrolidino-$C_{1-3}$-alkyl-carbonyl group,
  a piperidin-4-yl group which is substituted in the carbon skeleton by one to four $C_{1-3}$-alkyl groups,
  a piperidin-1-yl group which may be substituted in the carbon skeleton by one to four $C_{1-3}$-alkyl groups, a piperazinyl group which may be substituted in the 4 position by a $C_{1-3}$-alkyl group, while the alkyl group may be substituted from position 2 by a hydroxy group, or a 6-methyl-6-aza-bicyclo[3.1.1]heptanyl or 8-methyl-8-aza-bicyclo[3.2.1.]octanyl group, while the above-mentioned alkyl groups may be straight-chain or branched, the tautomers, enantiomers, diastereomers, the mixtures thereof and the salts thereof.

2. Compounds of general formula I according to claim 1, wherein $R^2$ and $R^3$ are defined as in claim 1 and $R^1$ denotes a methyl, ethyl, propyl or phenyl group, the tautomers, enantiomers, diastereomers, the mixtures thereof and the salts thereof.

3. Compounds of general formula I according to claim 2, wherein $R^1$ denotes a methyl, ethyl, propyl or phenyl group, $R^2$ denotes a pyridinyl, pyrazinyl or furanyl group, a straight-chain or branched $C_{1-7}$-alkyl group, a phenyl group wherein two adjacent carbon atoms are linked together through a methylenedioxy, ethylenedioxy or difluoromethylenedioxy group, or a phenyl group which may be substituted by one or two fluorine, chlorine, bromine or iodine atoms or by one or two $C_{1-3}$-alkyl, nitro, cyano, amino, $C_{1-3}$-alkyl-carbonylamino, phenylcarbonylamino, $C_{1-3}$-alkylsulphonylamino, trifluoromethyl, carboxy, $C_{1-3}$-alkoxy, di-($C_{1-3}$-alkyl)-amino-$C_{1-3}$-alkyloxy, $C_{1-3}$-alkoxy-carbonyl, $C_{1-3}$-alkylaminocarbonyl, hydroxycarbonyl-$C_{1-3}$-alkyl-aminocarbonyl, $C_{1-3}$-alkoxy-carbonyl-$C_{1-3}$-alkyl-aminocarbonyl, di-($C_{1-3}$-alkyl)-amino-$C_{1-3}$-alkylaminocarbonyl, carboxy-$C_{1-3}$-alkyl, $C_{1-3}$-alkoxy-carbonyl-$C_{1-3}$-alkyl, amino-$C_{1-3}$-alkyl or $C_{1-3}$-alkyl-carbonyl-amino-$C_{1-3}$-alkyl groups, while the substituents are identical or different, and $R^3$ denotes a $C_{3-7}$-cycloalkyl group, a cyclohexyl group which is substituted by a di-($C_{1-3}$-alkyl)-amino, di-($C_{1-3}$-alkyl)-amino-$C_{1-3}$-alkyl, carboxy, di-($C_{1-3}$-alkyl)-amino-$C_{1-3}$-alkyl-aminocarbonyl, amino-$C_{1-3}$alkyloxy, N-($C_{1-3}$-alkyl)-N-(phenyl-$C_{1-3}$-alkyl)-amino-$C_{1-3}$-alkyl, piperidino-$C_{1-3}$-alkyl, piperazino-$C_{1-3}$-alkyl, 4-($C_{1-3}$-alkyl)-piperazino-$C_{1-3}$-alkyl, pyrrolidino-$C_{1-3}$-alkyl, 2-oxo-pyrrolidino-$C_{1-3}$-alkyl, morpholino-$C_{1-3}$-alkyl or di-($C_{1-3}$-alkyl)-amino-$C_{1-3}$-alkyloxy group, a cyclohexyl group wherein the methylene group in the 4 position is replaced by a sulphur atom, a piperidinyl group which may be substituted at the amino-nitrogen atom by a $C_{1-3}$-alkyl, benzyl, carboxy, hydroxycarbonyl-$C_{1-3}$-alkyl, $C_{1-4}$-alkoxy-carbonyl, di-($C_{1-3}$-alkyl)-amino-$C_{1-3}$-alkyl-carbonyl or di-($C_{1-3}$-alkyl)-amino-$C_{1-3}$-alkyl-aminocarbonyl group, or a 4-($C_{1-3}$-alkyl)-piperazinyl group, while the above-mentioned alkyl groups may be straight-chain or branched, the tautomers, enantiomers, diastereomers, the mixtures thereof and the salts thereof.

4. Compounds of general formula I according to claim 3, wherein $R^1$ denotes a methyl or ethyl group, $R^2$ denotes a furanyl group, an ethyl, propyl, butyl or pentyl group, a phenyl group wherein two adjacent carbon atoms are linked together through a methylenedioxy or ethylenedioxy group, or a phenyl group which may be substituted by one or two methoxy groups, and $R^3$ denotes a cyclohexyl group which is substituted by a dimethylamino group, a cyclohexyl group wherein the methylene group in the 4 position is replaced by a sulphur atom, or a piperidinyl group which is substituted at the amino-nitrogen atom by a $C_{1-3}$-alkyl group, while the above-mentioned alkyl groups may be straight-chain or branched, the tautomers, enantiomers, diastereomers, the mixtures thereof and the salts thereof.

5. The following compounds of general formula I according to claim 1:

(a) 5-acetyl-3-[benzo[1,3]dioxol-5-yl-(1-methyl-piperidin-4-ylamino)-methylidene]-2-indolinone

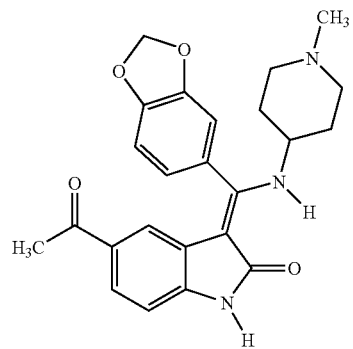

(b) 5-acetyl-3-[phenyl-(1-methyl-piperidin-4-ylamino)-methylidene]-2-indolinone

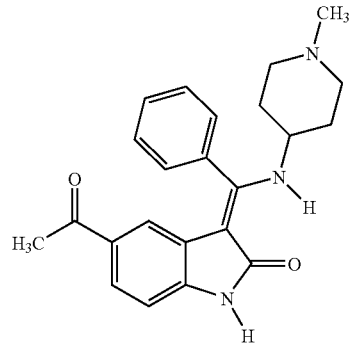

(c) 5-acetyl-3-[phenyl-(1-ethyl-piperidin-4-ylamino)-methylidene]-2-indolinone

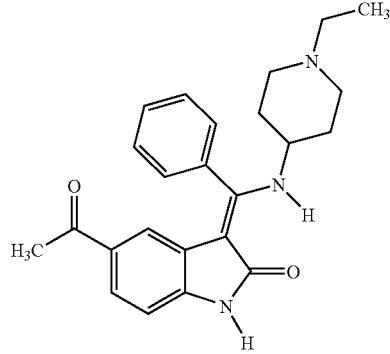

(d) 5-acetyl-3-[phenyl-(1-propyl-piperidin-4-ylamino)-methylidene]-2-indolinone

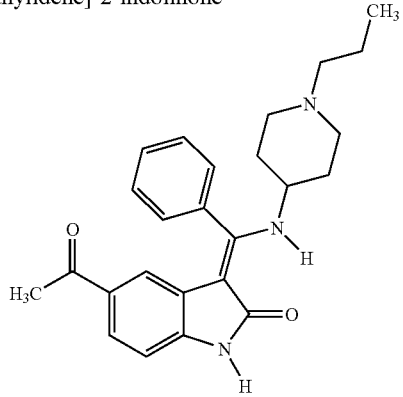

(e) 5-acetyl-3-[(1-methyl-piperidin-4-ylamino)-(2,3-dihydro-benzo[1,4]dioxin-6-yl)-methylidene]-2-indolinone

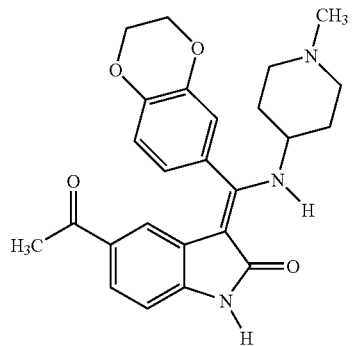

(f) 5-acetyl-3-[benzo[1,3]dioxol-5-yl-(1-ethyl-piperidin-4-ylamino)-methylidene]-2-indolinone

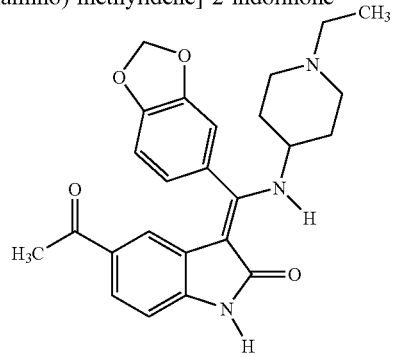

(g) 5-acetyl-3-[4-methoxy-phenyl-(4-trans-dimethylamino-cyclohexylamino)-methylidene]-2-indolinone

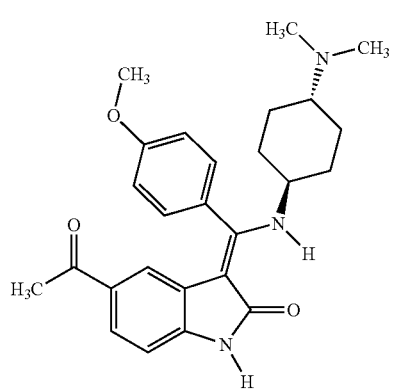

(h) 5-acetyl-3-[4-methoxy-phenyl-(1-methyl-piperidin-4-ylamino)-methylidene]-2-indolinone

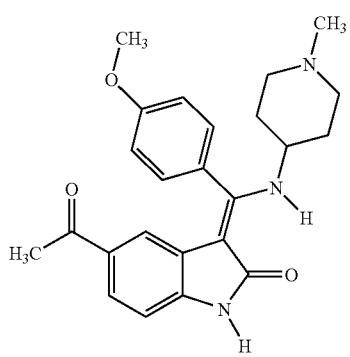

(i) 5-acetyl-3-[3-methoxy-phenyl-(1-methyl-piperidin-4-ylamino)-methylidene]-2-indolinone

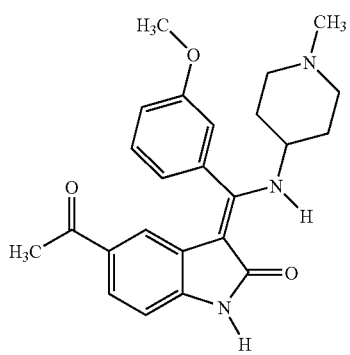

(j) 5-acetyl-3-[3,5-dimethoxy-phenyl-(1-methyl-piperidin-4-ylamino)-methylidene]-2-indolinone

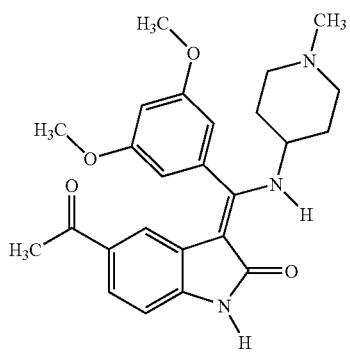

(k) 5-acetyl-3-[phenyl-(tetrahydrothiopyran-4-ylamino)-methylidene]-2-indolinone

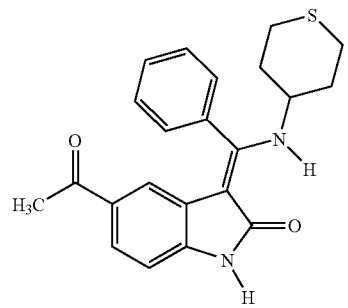

(l) 5-propionyl-3-[benzo[1,3]dioxol-5-yl-(dimethylamino-cyclohexylamino)-methylidene]-2-indolinone

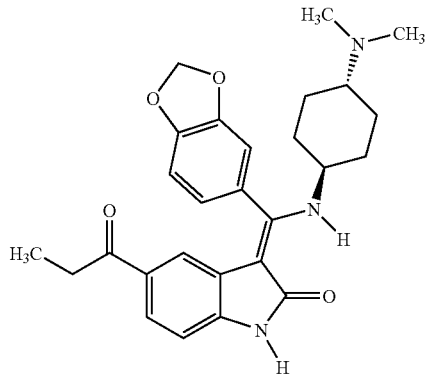

(m) 5-acetyl-3-[furan-3-yl-(1-methyl-piperidin-4-ylamino)-methylidene]-2-indolinone

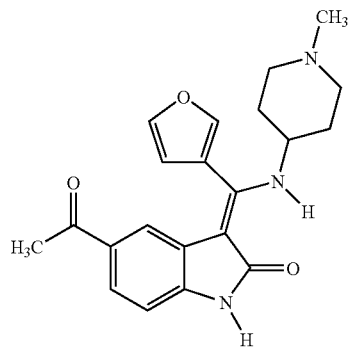

(n) 5-acetyl-3-[1-phenyl-(trans-4-dimethylaminomethyl-cyclohexylamino)-methylidene]-2-indolinone

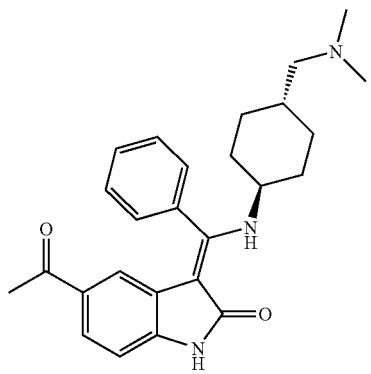

(o) 5-acetyl-3-[(trans-4-dimethylamino-cyclohexylamino)-propylidene]-2-indolinone

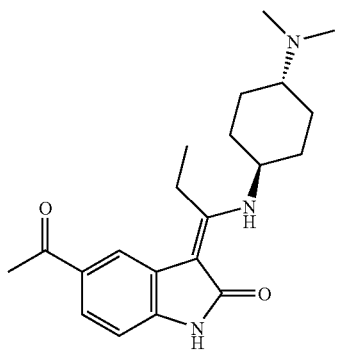

(p) 5-acetyl-3-[1-methyl-piperidin-4-ylamino)-propylidene]-2-indolinone

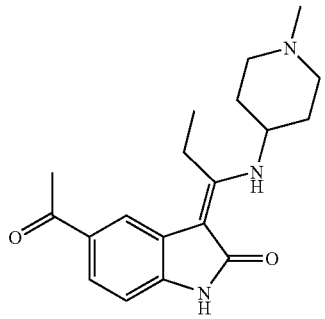

(q) 5-acetyl-3-[4-trifluoromethyl-phenyl-(trans-4-dimethylamino-cyclohexylamino)-methylidene]-2-indolinone

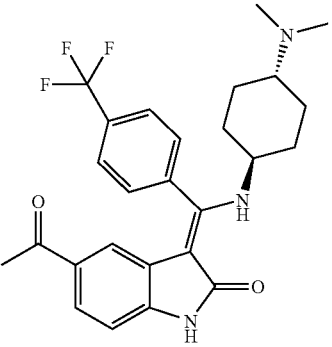

as well as the tautomers, enantiomers, diastereomers, the mixtures thereof and the salts thereof.

6. Physiologically acceptable salts of the compounds according to claim 1 with inorganic or organic acids or bases.

7. Pharmaceutical compositions containing a compound according to claim 6 optionally together with one or more intert carriers and/or diluents.

8. Pharmaceutical compositions containing a compound according to claim 1 optionally together with one or more inert carriers and/or diluents.

9. Process for preparing a pharmaceutical composition according to claim 8, by incorporating said compound in one or more inert carriers and/or diluents by a non-chemical method.

10. A method of treating type I and type II diabetes mellitus, diabetes associated disorders such as diabetic neuropathy and degenerative neurological diseases such as Alzheimer's disease, stroke, neurotraumatic injuries and bipolar disorders, said method comprised of the steps of administering to a patient in need thereof an effective amount of a compound according to claim 1 or a pharmaceutically acceptable salt thereof.

11. Process for preparing the compounds of general formula I according to claim 1 comprised of the steps of
a) reacting a compound of general formula (II)

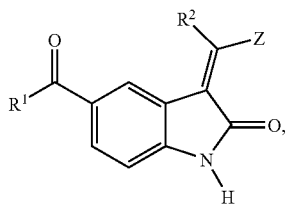

wherein $R^1$ and $R^2$ are defined as mentioned in one of claim 1 and Z denotes a leaving group, with an amine of general formula

$$R^3\text{—}NH_2 \qquad (III),$$

wherein $R^3$ is defined as in claim 1, while any hydroxy, amino or imino groups contained in the groups $R^2$ and/or $R^3$ may temporarily be protected by suitable protective groups, said method further characterized in that:

in order to prepare a compound of formula I which contains an aminocarbonyl group, a compound which contains a carboxy group is reacted with the corresponding amine, in order to prepare a compound of formula I which contains a carbonylamino group, a compound which contains an amino group is reacted with the corresponding acid chloride, in order to prepare a compound of formula I which contains an aminomethyl group, a compound which contains a cyano group is hydrogenated to produce the corresponding aminomethyl derivative, in order to prepare a compound of formula I which contains an amino group, a compound which contains a nitro group is hydrogenated, and/or any protective groups which may be used during the reaction are then cleaved and/or the compounds of general formula I thus obtained are resolved into their enantiomers and/or diastereomers and/or the compounds of general formula I thus obtained are converted into their salts, particularly for pharmaceutical use into the physiologically acceptable salts thereof with inorganic or organic acids or bases.

* * * * *